US010927412B2

(12) United States Patent
Giudice et al.

(10) Patent No.: US 10,927,412 B2
(45) Date of Patent: Feb. 23, 2021

(54) ENDOMETRIOSIS CLASSIFIER

(71) Applicant: The Regents of the University of California, Oakland, CA (US)

(72) Inventors: Linda C. Giudice, Los Altos Hills, CA (US); Juan C. Irwin, El Cerrito, CA (US); John S. Tamaresis, Redwood City, CA (US)

(73) Assignee: The Regents of the University of California, Oakland, CA (US)

( * ) Notice: Subject to any disclaimer, the term of this patent is extended or adjusted under 35 U.S.C. 154(b) by 816 days.

(21) Appl. No.: 15/026,582

(22) PCT Filed: Sep. 30, 2014

(86) PCT No.: PCT/US2014/058338
§ 371 (c)(1),
(2) Date: Mar. 31, 2016

(87) PCT Pub. No.: WO2015/050875
PCT Pub. Date: Apr. 9, 2015

(65) Prior Publication Data
US 2016/0251718 A1     Sep. 1, 2016

Related U.S. Application Data

(60) Provisional application No. 61/885,284, filed on Oct. 1, 2013.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 2005/0202432 | A1 | 9/2005 | Jelinksy et al. |
| 2008/0318237 | A1* | 12/2008 | Giudice ............... C12Q 1/6883 435/6.17 |
| 2010/0310690 | A1 | 12/2010 | Tchernitchin et al. |
| 2012/0065084 | A1 | 3/2012 | Sotiriou et al. |
| 2012/0289418 | A1 | 11/2012 | Willard-Gallo et al. |
| 2013/0022593 | A1 | 1/2013 | Giudice |

FOREIGN PATENT DOCUMENTS

WO    2012031008 A2    3/2012

OTHER PUBLICATIONS

Handbook of Chemistry and Physics, 49th Edition, 1968, Weast (ed.), The Chemical Rubber Co., Cleveland, Ohio, p. A-245.*
PCT/US2014/058338, , "International Search Report and Written Opinion", dated Dec. 19, 2014, 15 pages.

* cited by examiner

*Primary Examiner* — James Martinell
(74) *Attorney, Agent, or Firm* — Kilpatrick Townsend & Stockton LLP

(57) ABSTRACT

The present disclosure provides methods and compositions that are useful for diagnosing the presence or absence of endometriosis and the severity of endometriosis in a subject. The methods and compositions are also useful for distinguishing endometriosis from other uterine or pelvic pathologies in a subject. Also described are sets of genes whose expression levels in a biological sample are diagnostic for endometriosis, and compositions useful for diagnosis, prognosis, and/or treatment of endometriosis.

10 Claims, 3 Drawing Sheets

ENDOMETRIOSIS CLASSIFIER

CROSS-REFERENCES TO RELATED APPLICATIONS

The present application is the U.S. National Stage Entry of PCT/US2014/058338, filed Sep. 30, 2014, and claims priority from and the benefit of U.S. Provisional Application No. 61/885,284, filed Oct. 1, 2013, titled "ENDOMETRIOSIS CLASSIFIER," the entire contents of each of which are incorporated herein by reference for all purposes.

STATEMENT AS TO RIGHTS TO INVENTIONS MADE UNDER FEDERALLY SPONSORED RESEARCH AND DEVELOPMENT

This invention was made with government support under grant NIH/NICHD U54HD055764 awarded by the National Institutes of Health Eunice Kennedy Shriver National Institute of Child Health and Human Development. The government has certain rights in this invention.

REFERENCE TO A "SEQUENCE LISTING," A TABLE, OR A COMPUTER PROGRAM LISTING APPENDIX SUBMITTED AS AN ASCII TEXT FILE

Tables 16, 17, and 18, created on Sep. 23, 2013, machine format IBM-PC, MS-Windows operating system, submitted herewith on six (6) compact discs (CD-R) according to 37 C.F.R. 1.52(e)(1) and 1.77(b)(5), are hereby incorporated by reference in their entirety for all purposes. Compact disc 1 contains Table 16, copy 1, 6,010,697 bytes. Compact disc 2 contains Table 16, copy 2, 6,010,697 bytes. Compact disc 3 contains Table 17, copy 1, 6,051,004 bytes. Compact disc 4 contains Table 17, copy 2, 6,051,004 bytes. Compact disc 5 contains Table 18, copy 1, 6,066,294 bytes. Compact disc 6 contains Table 18, copy 2, 6,066,294 bytes.

BACKGROUND OF THE INVENTION

Endometriosis is a complex disorder associated with pelvic pain and infertility, and is characterized by the implantation of endometrial tissue outside the uterus, primarily on the pelvic peritoneum and ovaries (Giudice L C, Kao L C (2004) The Lancet 364:1789-99). Endometriosis affects 6-10% of women in the general population and 35-50% of women with pain and/or infertility (Eskenazi B, Warner M L (1997) Obstet Gynecol Clin North Am 24:235-58). It is widely accepted that by retrograde menstruation (Sampson J A (1927) Am J Obstet Gynecol 14:442-469), endometrial tissue establishes itself on the peritoneum of women with endometriosis due to heritable and/or acquired defects that confer survival advantage and promote attachment, growth, neoangiogenesis, and invasion into the peritoneum.

The main clinical symptoms of endometriosis are pelvic pain, bleeding and infertility, with the latter proposed to be related to impaired implantation due, in part, to impaired decidualization of endometrial stromal fibroblasts (ESFs). This application provides methods and compositions that are useful for diagnosing endometriosis.

BRIEF SUMMARY OF THE INVENTION

The present application provides methods and compositions for diagnosing the presence, absence and/or severity of endometriosis in a subject. In one aspect, a method for diagnosing endometriosis is described, the method comprising:

determining the expression level of at least one set of genes, the set of genes comprising the genes in Table 7, Table 8, Table 9, Table 10, Table 11, Table 12, Table 13, Table 14, or Table 15, in a tissue sample comprising endometrial cells from a subject;

associating the expression level with the presence and severity of endometriosis; and providing a diagnosis of the presence, absence or severity of endometriosis based on the association.

In some embodiments, the method can be a computer implemented method. For example, in one embodiment, a computer implemented method is provided, the method comprising:

(i) receiving the expression data of at least one set of genes, the set of genes comprising the genes in Table 7, Table 8, Table 9, Table 10, Table 11, Table 12, Table 13, Table 14, and/or Table 15; and (ii) associating the expression data of the at least one set of genes with the presence, absence or severity of endometriosis, thereby diagnosing endometriosis.

In another aspect, a method for detecting the expression of genes in a tissue sample comprising endometrial cells or tissue is described, the method comprising:

detecting the expression level of at least one set of genes, the set of genes comprising the genes in Table 7, Table 8, Table 9, Table 10, Table 11, Table 12, Table 13, Table 14, or Table 15, in a tissue sample comprising endometrial cells from a subject.

In some embodiments of the above aspects, the methods comprise determining or detecting expression of the at least one set of genes by hybridizing RNA isolated from the endometrial tissue sample to a microarray. In some embodiments, the methods comprise determining or detecting expression of the at least one set of genes by amplifying RNA from the tissue samples using PCR. In some embodiments, the methods comprise determining or detecting expression of the at least one set of genes by determining or measuring the expression level of proteins encoded by the at least one set of genes.

In some embodiments, the method further comprises obtaining a sample comprising endometrial cells or tissue. The sample comprising endometrial cells or tissue can be obtained directly from a subject or patient, such as by surgery or biopsy, or can be obtained indirectly from a health care provider, such as a doctor, who performed the surgery or biopsy procedure. In one embodiment, the method comprises identifying a subject in need of treatment for endometriosis or another uterine pathology.

In another aspect, kits that are useful for diagnosing endometriosis are provided. For instance, in some embodiments, the kit comprises a plurality of oligonucleotides that specifically hybridize to mRNA, or a complement thereof, expressed by a set of genes, the set of genes comprising the genes in Table 7, Table 8, Table 9, Table 10, Table 11, Table 12, Table 13, Table 14, or Table 15, or any combination thereof. In some embodiments, the kit comprises a set of oligonucleotides that specifically hybridize to mRNA, or a complement thereof, expressed by the set of genes in Table 7, the set of genes in Table 8, the set of genes in Table 10, the set of genes in Table 11, the set of genes in Table 13, or the set of genes in Table 14. In one embodiment, the kit comprises a set of oligonucleotides that specifically hybridize to mRNA, or a complement thereof, expressed by the set of genes in Table 9 the set of genes in Table 12, or the set of genes in Table 15. In some embodiments, the kit comprises a set of probes for detecting nucleic acids or proteins expressed by a plurality of the genes in Tables 7-15.

In some embodiments, the kit comprises reagents that detect the expression of a protein encoded by or expressed by a plurality of the genes in Table 7, Table 8, Table 9, Table 10, Table 11, Table 12, Table 13, Table 14, or Table 15. In some embodiments, the reagent is an antibody or immunologically active fragment thereof.

In another aspect, a microarray that is useful for detecting the expression of the genes described herein is provided. In some embodiments, the microarray comprises a set of oligonucleotides that specifically hybridize to mRNA expressed by one or more sets of genes, the set of genes comprising the genes in Table 7, Table 8, Table 9, Table 10, Table 11, Table 12 Table 13, Table 14, or Table 15, or any combination thereof.

In another aspect, a computer product for performing one or more steps of the methods described herein is described. In one embodiment, the computer product comprises a non-transitory computer readable medium storing a plurality of instructions for controlling a processor to perform an operation of one or more of the following steps:
(i) receiving the expression data of at least one set of genes, the set of genes comprising the genes in Table 7, Table 8, Table 9, Table 10, Table 11, Table 12, Table 13, Table 14, or Table 15; and
(ii) associating the expression data of the at least one set of genes with the presence, absence or severity of endometriosis.

In some embodiments, a computer system is provided that comprises a computer product for performing one or more steps of the methods described herein. In one embodiment, the computer system comprises a non-transitory computer readable medium storing a plurality of instructions for controlling a processor to perform an operation of one or more of the following steps:
(i) receiving the expression data of at least one set of genes, the set of genes comprising the genes in Table 7, Table 8, Table 9, Table 10, Table 11, Table 12, Table 13, Table 14, and/or Table 15; and
(ii) associating the expression data of the at least one set of genes with the presence, absence or severity of endometriosis; and
one or more processors for executing instructions stored on the computer readable medium.

In some embodiments, the diagnosis of the presence, absence or severity of endometriosis provided is at least 90% accurate, for example at least 91%, 92%, 93%, 94%, 95%, 96%, 97%, 98%, 99% or 100% accurate.

In some aspects, a composition for determining the presence, absence or severity of endometriosis is provided, the composition comprising at least one set of the genes, where a set of genes comprises or consists of the genes in any one of Tables 7-15 (i.e., the genes in each Table comprise or consist of a set of genes). In some embodiments, the composition comprising the set of genes in any of Tables 7-15 is for use in a method of determining or diagnosing the presence, absence or severity of endometriosis as described herein. In some embodiments, the composition is used in an in vitro method for determining the presence, absence or severity of endometriosis. The use can also provide a prognosis regarding the course of disease, or can be used to identify a subject as a candidate for treatment for endometriosis. In some embodiments, the composition is for use in a method for treating endometriosis, wherein the treatment regimen is determined or modified based on the expression levels of at least one of the sets of genes in Table 7, Table 8, Table 9, Table 10, Table 11, Table 12, Table 13, Table 14, or Table 15, in a tissue sample comprising endometrial cells from a subject.

Further embodiments of the invention are described herein.

Definitions

As used herein, the term "associating" refers to classifying a biological sample into a disease class and/or severity class based on gene expression levels in the biological sample. The associating can be performed using a margin tree classification method.

The term "margin tree classification method" refers to an algorithm that can classify data into two or more classes. The method can define a line or plane/hyperplane that separates distinct classes from each other. The minimum distance to this line or plane/hyperplane, among all the data points, is the margin. For classifying more than two classes, a tree-like sequence of binary decisions can be employed. At each binary decision the classification method partitions the classes into two groups with the maximum margin. The classification method can compute the margin between each pair of classes. The method uses the margins to determine the specific tree, presented as a sequence of binary decisions, that best fits the data. In some embodiments, the data are microarray data. The method can also produce a list of probe sets used for each binary decision. For example, the method can produce two lists of probe sets: one for the presence or absence of pathology decision, and another for the type of pathology decision.

The term "marker" refers to a molecule (typically protein, nucleic acid, carbohydrate, and/or lipid) that is expressed in an endometrial cell from a women with endometriosis, expressed on the surface of an endometrial cell from a woman with endometriosis, or secreted by an endometrial cell from a woman with endometriosis in comparison to a cell from a woman who does not have endometriosis, and which is useful for the diagnosis of endometriosis, for providing a prognosis, for predicting the fertility of an individual with endometriosis, and for preferential targeting of a pharmacological agent to the endometrial cell. Oftentimes, such markers are molecules that are overexpressed in an endometrial cell from a woman with endometriosis in comparison to a cell from a woman without endometriosis, for instance, 1-fold overexpression, 2-fold overexpression, 3-, 4-, 5-, 6-, 7-, 8-, 9-, or 10-fold overexpression or more fold-overexpression in comparison to a cell from a woman without endometriosis. Further, a marker can be a molecule that is inappropriately synthesized in the endometrial cell of a woman with endometriosis, for instance, a molecule that contains deletions, additions, or mutations in comparison to the molecule expressed in a cell from a woman without endometriosis. Alternatively, such biomarkers are molecules that are underexpressed in an endometrial cell from a woman with endometriosis in comparison to a cell from a woman without endometriosis, for instance, 1-fold underexpression, 2-fold underexpression, 3-, 4-, 5-, 6-, 7-, 8-, 9-, or 10-fold underexpression, or more fold-overexpression in comparison to a cell from a woman without endometriosis. Further, a marker can be a molecule that is inappropriately synthesized in a cell from a woman with endometriosis, for instance, a molecule that contains deletions, additions or mutations in comparison to the molecule expressed in a cell from a woman without endometriosis.

It will be understood by the skilled artisan that markers may be used in combination with other markers or tests for any of the uses, e.g., prediction, diagnosis, prognosis, or treatment of endometriosis or fertility, disclosed herein.

"Biological sample" includes portions of tissues such as biopsy, surgical and autopsy samples, and preserved, and/or frozen sections taken for histologic or other analytical purposes. Such samples include blood and blood fractions or products (e.g., serum, plasma, platelets, red blood cells, immune cells, stem cells, and the like), sputum, endometrial tissue, the uterine fundus, thyroid tissue, cultured cells, e.g., primary cultures, passaged cells, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; or rabbit.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., endometrial, etc.), the size and type of the tissue, among other factors. Representative biopsy techniques include, but are not limited to, excisional biopsy, incisional biopsy, aspirational biopsy, curettage, needle biopsy, surgical biopsy, and bone marrow biopsy. An "excisional biopsy" refers to the removal of an entire endometrial tissue mass with a small margin of non-endometrial tissue surrounding it. An "incisional biopsy" refers to the removal of a wedge of endometrial tissue. Biopsy techniques are discussed, for example, in Harrison's Principles of Internal Medicine, Kasper, et al., eds., 16th ed., 2005, Chapter 70, and throughout Part V.

The terms "overexpress", "overexpression", "overexpressed", or "up-regulated" interchangeably refer to a protein or nucleic acid (RNA) that is transcribed or translated at a detectably greater level in comparison to a control. The term includes overexpression due to transcription, post transcriptional processing, translation, post-translational processing, cellular localization (e.g., organelle, cytoplasm, nucleus, cell surface), and RNA and protein stability, as compared to a cell from a woman without endometriosis. Overexpression can be detected using conventional techniques for detecting mRNA (i.e., Q-PCR, RT-PCR, PCR, hybridization, sequencing) or proteins (i.e., ELISA, immunohistochemical and other immunoquantitative or immunolocalization techniques; mass spectrometry, gel electrophoresis). In pair-wise comparisons, overexpression can be 10%, 20%, 30%, 40%, 50%, 60%, 70%, 80%, 90% or more in comparison to a control. In certain instances, overexpression is 1-, 2-, 3-, 4-, 5-, 6-, 7-, 8-, 9-, 10-fold, or more higher levels of transcription or translation in comparison to a control.

The terms "underexpress", "underexpression", "underexpressed", or "down-regulated" interchangeably refer to a protein or nucleic acid that is transcribed or translated at a detectably lower level in comparison to a control. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., Q-PCR, RT-PCR, PCR, hybridization, sequencing) or proteins (i.e., ELISA, immunohistochemical and other immunoquantitative or immunolocalization techniques; mass spectrometry, gel electrophoresis). In pair-wise comparisons, underexpression can be 10%, 20%, 30%, 40%, 50%, 60%, 70%, 80%, 90% or less in comparison to a control. In certain instances, underexpression is 1-, 2-, 3-, 4-, 5-, 6-, 7-, 8-, 9-, 10-fold or more lower levels of transcription or translation in comparison to a control.

The term "control," when referring to a traditional pair-wise comparison, refers to a sample from a subject without endometriosis, for example a sample from a healthy subject without endometriosis or other uterine or pelvic conditions, or a sample from a subject having a uterine or pelvic condition or pathology that is not endometriosis. The term control can also refer to a sample from a subject having a different severity of endometriosis. The control can be a reference value that is representative of a population of healthy subjects without endometriosis, or a reference value that is representative of a population of subjects having other uterine conditions or pathologies that are not endometriosis. The control can also be from a sample or reference value that is matched to the same menstrual cycle phase as the test sample (e.g., a sample from a subject with endometriosis).

The term "differentially expressed", "differentially regulated", or "altered expression" refers generally to a protein or nucleic acid that is overexpressed (upregulated) or underexpressed (downregulated) in one sample compared to at least one other sample, generally in a patient with endometriosis, in comparison to a patient without endometriosis.

"Therapeutic treatment" refers to chemotherapy, hormonal therapy, other types of pharmacologic therapy, radiotherapy, immunotherapy, and targeted therapies (e.g., biologic, small molecule, pathway or cell cycle inhibitors).

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the term "diagnosis" refers to distinguishing between having and not having endometriosis. For example, the term can refer to distinguishing between the presence or absence of disease, or between a uterine or pelvic pathology that is not endometriosis versus endometriosis. The term can also refer to distinguishing the severity of endometriosis, e.g., minimal-to-mild versus moderate-to-severe endometriosis. The classifiers described herein can provide a diagnosis that distinguishes between no uterine or pelvic pathology and a uterine or pelvic pathology, and can also provide a diagnosis that distinguishes between a uterine or pelvic pathology that is not endometriosis and endometriosis. As used herein, the term "providing a prognosis" may refer to providing a prediction of the probable course and outcome of endometriosis or for a prediction of the probable outcome of a treatment course for endometriosis, or alternatively for providing a prediction of the probable outcome of a fertility trial or pain management trial in a patient with endometriosis.

The term "menstrual cycle phase-specific" refers to a specific phase of the menstrual cycle, or to a classifier developed using biological samples comprising endometrial tissue or cells from a specific phase of the menstrual cycle. In some embodiments, the term refers to a classifier developed using biological samples comprising endometrial tissue or cells from either the proliferative phase ("PE"), the early secretory phase ("ESE"), or the mid-secretory phase ("MSE") of the menstrual cycle.

The term "menstrual cycle phase-restricted" refers to the proliferative phase (PE) and the early secretory phase (ESE) of the menstrual cycle, or to a classifier developed using biological samples comprising endometrial tissue or cells from both the proliferative phase (PE) and the early secretory phase (ESE) of the menstrual cycle. The term is sometimes abbreviated herein as "PE+ESE" or as "PE.ESE."

The term "menstrual cycle phase-unrestricted" refers to all phases of the menstrual cycle, or to a classifier developed using biological samples comprising endometrial tissue or cells from all phases of the menstrual cycle. In some embodiments, the term refers to a classifier developed using biological samples comprising endometrial tissue or cells from the proliferative phase (PE), the early secretory phase (ESE), and the mid-secretory phase (MSE) of the menstrual cycle. The term is sometimes abbreviated herein as "PE+ESE+MSE" or as "PE.ESE.MSE."

DETAILED DESCRIPTION OF THE INVENTION

Introduction

Figure 1:
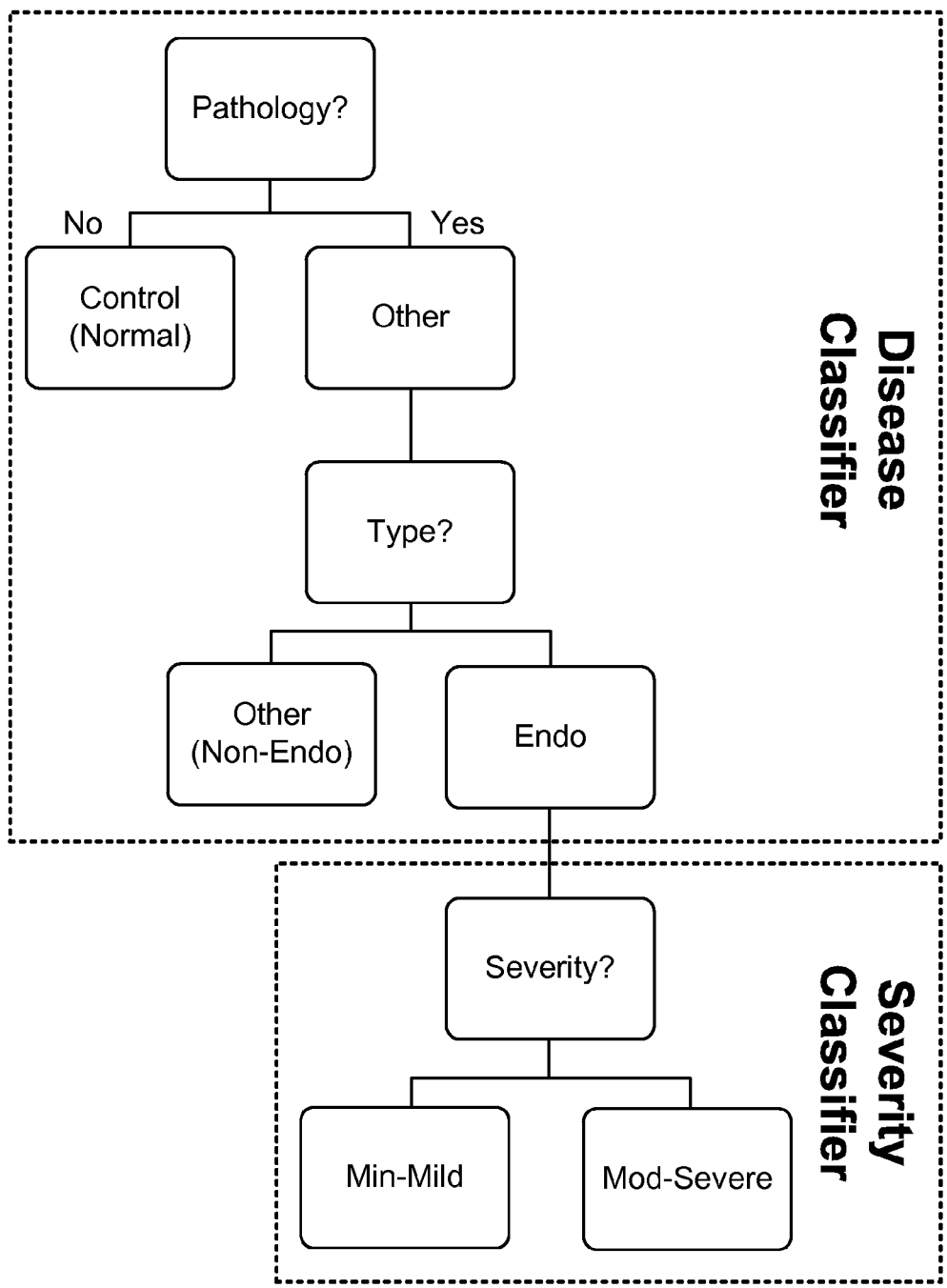
FIG. 1 shows a decision tree for the composite classifiers described herein.

The present disclosure provides methods and compositions for diagnosing endometriosis in a subject. The methods and compositions described herein are useful for determining if a subject suffers from a uterine or pelvic pathology, such as endometriosis, and, if the subject suffers from endometriosis, determining the severity of the endometriosis. The inventors have surprisingly discovered that the presence and severity of endometriosis can be diagnosed at a high level of accuracy (e.g., >90%) by determining the expression levels of defined sets of genes in an endometrial tissue sample. The defined sets of genes comprise a set of genes referred to herein as "core" genes, as well as other, non-core genes. The inventors have further surprisingly discovered that the number of core genes in a set that is diagnostic for endometriosis can be relatively low, for example, less than 100 genes.

The methods described herein associate the gene expression levels of the defined sets of genes with a particular disease class and, if applicable, a severity class of endometriosis. In some embodiments, the methods and compositions described herein assign an endometrial tissue sample from a subject to a disease or no disease category; assign an endometrial tissue sample from the disease category to an endometriosis or non-endometriosis category; and assign an endometrial tissue sample from the endometriosis category to a minimal to mild or moderate to severe category.

In some embodiments, the method comprises determining the expression level of a plurality of genes in a tissue sample from a subject; associating the expression level with the presence and severity of endometriosis; and providing a diagnosis of the presence, absence or severity of endometriosis based on the association. In some embodiments, the method comprises determining the expression level of at least one set of genes in a tissue sample from a subject; associating the expression level with the presence and severity of endometriosis; and providing a diagnosis of the presence, absence or severity of endometriosis based on the association. In some embodiments, the set of genes comprises the core genes in Tables 7, 8, 9, 10, 11, 12, 13, 14 and/or 15. In some embodiments, the tissue sample comprises endometrial cells (e.g., an endometrial biopsy sample).

The method can further comprise determining a disease class and/or severity class based on the association. For example, the method can further comprise determining a disease class selected from the group consisting of: no endometriosis and no uterine/pelvic pathology; no endometriosis but other pathology; and endometriosis, where the disease class is determined by associating the expression level of at least one set of genes comprising the genes in Table 7, Table 8, Table 10, Table 11, Table 13, or Table 14 with the disease class. In some embodiments, the method further comprises classifying the severity of endometriosis into a severity class selected from minimal to mild endometriosis or moderate to severe endometriosis, where the severity of endometriosis is classified by associating the expression level of at least one set of genes comprising the genes in Table 9 Table 12, or Table 15 with the severity class. Thus, the present disclosure further provides diagnostic classifiers that can be used to determine the presence or absence of endometriosis as well as the severity of endometriosis.

The methods and compositions described herein can also be used to provide a diagnosis of endometriosis based on the phase of the menstrual cycle at the time the endometrial tissue sample is obtained from the subject, i.e., proliferative phase, early secretory phase, or mid-secretory phase. In some embodiments, the diagnosis is proliferative (PE) phase-specific. In some embodiments, the diagnosis is early secretory (ESE) phase-specific. In some embodiments, the diagnosis is mid-secretory (MSE) phase-specific. In another aspect, the diagnosis is based on samples from all three menstrual cycle phases, and is therefore menstrual cycle phase-independent (i.e., phase-unrestricted). In some embodiments, the diagnosis is based on samples from both the PE and ESE phases (i.e., phase-restricted). The methods and compositions will now be described.

Methods

In order to provide a diagnosis of the presence, absence and/or severity of endometriosis, the expression level of a plurality of genes in a tissue sample is determined. Thus, in one aspect, the method for diagnosing endometriosis comprises the steps of:

determining the expression level of a plurality of genes in a tissue sample comprising endometrial cells from a subject;

associating the expression level with the presence and severity of endometriosis; and providing a diagnosis of the presence, absence or severity of endometriosis.

In some embodiments, the determining step comprises determining the expression level of a plurality of genes selected from the sets of genes in Tables 7-15. Thus, in one embodiment, the method comprises the steps of:

determining the expression level of a plurality of genes from at least one set of genes in Tables 7-15 in a tissue sample comprising endometrial cells from a subject;

associating the expression level with the presence and severity of endometriosis; and providing a diagnosis of the presence, absence or severity of endometriosis.

In some embodiments, the expression level of one or more sets of genes in a tissue sample is determined. Each set of genes comprises a group or set of common genes, also referred to herein as "core genes." In some embodiments, a set of genes comprises the genes in Table 7, Table 8, Table 9, Table 10, Table 11, Table 12, Table 13, Table 14, or Table 15. Each set of genes can further comprise non-core genes in addition to the core genes. For a defined level of accuracy, the core genes in each set of genes are the same. For example, a set of genes diagnosing the presence or absence of disease (uterine/pelvic conditions/pathologies) in PE phase-restricted tissue samples at 100% accuracy was identified, where the set of genes comprises the core genes in Table 7. In some embodiments, the set of genes used to diagnose the type of disease (endometriosis versus non-endometriosis) in PE phase-restricted tissue samples at 100% accuracy comprises the core genes in Table 8. In some embodiments, the set of genes used to diagnose the severity of endometriosis in PE phase-restricted tissue samples at 100% accuracy comprises the core genes in Table 9. In some embodiments, the set of genes used to diagnose the presence or absence of disease in ESE phase-restricted tissue samples at 100% accuracy comprises the set of genes in Table 10. In some embodiments, the set of genes used to diagnose the type of disease (endometriosis versus non-endometriosis) in ESE phase-restricted tissue samples at 100% accuracy comprise the core genes in Table 11. In some embodiments, the set of genes used to diagnose the severity of endometriosis in ESE phase-restricted tissue samples at 100% accuracy comprise the core genes in Table 12. In some embodiments, the set of genes used to diagnose the presence or absence of disease in MSE phase-restricted tissue samples at 91% accuracy comprises the set of genes in Table 13. In some embodiments, the set of genes used to diagnose the type of disease (endometriosis versus non-endometriosis) in MSE phase-restricted tissue samples at 91% accuracy comprise the core genes in Table 14. In some embodiments, the set of genes used to diagnose the severity of endometriosis in MSE phase-restricted tissue samples at 100% accuracy comprise the core genes in Table 15. Thus, in some embodiments, the tissue sample comprises cells or tissue from the PE phase of the menstrual cycle. In one embodiment, the tissue sample comprises cells or tissue from the ESE phase of the menstrual cycle. In one embodiment, the tissue sample comprises cells or tissue from the MSE phase of the menstrual cycle.

In some embodiments, the method comprises:

determining the expression level of at least one set genes, the set of genes comprising the genes in Tables 7, 8, 9, 10, 11, 12, 13, 14, or 15 in a tissue sample comprising endometrial cells from a subject;

associating the expression level with the presence and severity of endometriosis; and providing a diagnosis of the presence, absence or severity of endometriosis.

In some embodiments, the expression levels of the genes in one or more sets of genes will be up-regulated compared to the expression levels in a control sample. In some embodiments, the expression levels of the genes in one or more sets of genes will be down-regulated compared to the expression levels in a control sample. In some embodiments, the expression levels of some of the genes in a particular set of genes will be up-regulated, while the expression levels of some of the genes in the set of genes will be down-regulated, compared to the expression levels in a control sample. In some embodiments, the expression levels of the genes in one or more sets of genes will be up-regulated in particular phase of the menstrual cycle compared to the expression levels in a phase-matched control sample. In some embodiments, the expression levels of the genes in one or more sets of genes will be down-regulated in particular phase of the menstrual cycle compared to the expression levels in a phase-matched control sample. In some embodiments, the expression levels of one or more genes can be up-regulated in one phase, and down-regulated in another phase, compared to the expression levels in a phase-cycle matched control sample. Exemplary relative expression levels of genes that were used for phase-specific endometriosis classifiers are shown in Tables 16-18 and further described in the Examples.

Traditional pair-wise comparisons are typically based on comparing the expression level of a gene, protein, or other biomarker between a first or test sample (i.e., a sample from a subject with a uterine or pelvic disease, or a sample from a subject with endometriosis) and a second or control sample (i.e., a sample from a subject without a uterine or pelvic disease, including endometriosis, or a subject having a uterine or pelvic disease that is not endometriosis), and determining a statistically significant difference in expression. However, in the classifiers described herein, differences in expression levels for the individual genes in the sets of genes used by classifiers can range from very large to very small, where the latter can be below the threshold typically considered statistically significant or biologically relevant in a conventional pair-wise comparison. Thus, in some embodiments, the difference in expression level of an individual gene in one or more sets of the genes described herein when compared to the expression level of the same gene, protein or biomarker detected in a different biological sample (i.e., the magnitude or absolute value of the change) may not be statistically significant or considered biologically relevant in a pair-wise comparison, but can provide a useful diagnosis when combined with the expression levels of other members of the set of genes used in the classifier. Thus, in some embodiments, the expression levels of an individual gene, protein or biomarker may be less than 10% different than the expression level of the gene, protein or biomarker in a tissue sample from another subject, but still provide a useful and accurate diagnosis of a uterine or pelvic disease and/or endometriosis. Further, in some embodiments of the methods described herein, each tissue sample from a subject (or tissue samples from different subjects) is subjected to the same analysis to determine the presence, absence or severity of endometriosis, such that the methods allow each sample to be analyzed independently of comparison to a reference or control sample.

It will be understood that the sets of genes that are used to diagnose the presence and severity of endometriosis will vary based on the desired level of accuracy. For example, the set of genes that diagnoses the presence or absence of disease in a phase-restricted sample at 95% accuracy can differ from the set of genes giving a diagnosis at 100% accuracy. Accordingly, the core genes present in each set of genes will also differ based on the level of accuracy. It will be further understood that the non-core genes in each set of genes that provide a given level of accuracy can also differ from each other.

In some embodiments, the determining step comprises determining the expression level of the genes in a disease classifier described herein. In one embodiment, the determining step comprises determining the expression level of the genes in a severity classifier described herein. In one embodiment, the determining step comprises determining the expression level of the genes in a composite classifier described herein. In some embodiments, the determining step comprises determining the expression level of the set of genes in Tables 7-15. In some embodiments, the determining step comprises determining the expression level of the set of genes in Tables 16-18. In some embodiments, the determining step comprises determining the expression level of a plurality of genes from one or more of the sets of genes in Tables 7-15 or Tables 16-18. In some embodiments, the determining step comprises detecting or measuring the amount of a gene product that is expressed by the genes of the classifiers described herein. In some embodiments, the gene product that is detected or measured is an RNA that is transcribed by the genes of the classifiers described herein. In some embodiments, the gene product that is detected or measured is a protein or polypeptide that is encoded by the genes of the classifiers described herein.

In some embodiments, the associating step comprises a margin tree classification method. In some embodiments, the margin tree classification method is executable on a computer configured with executable instructions.

In some embodiments, the step of providing a diagnosis of endometriosis comprises providing information on the severity of endometriosis. Thus, in some embodiments, the diagnosis is minimal to mild endometriosis. In one embodiment, the diagnosis is moderate to severe endometriosis. In one embodiment, the diagnosis is provided to a health care provider, such as a nurse or physician. In one embodiment, the diagnosis is provided to the subject or patient (or the guardian of the patient if the patient is a non-human mammal). In some embodiments, the step of providing a diagnosis of endometriosis further comprises providing a course of treatment to a patient diagnosed with endometriosis. In some embodiments, the step of providing a diagnosis of endometriosis involves clinical trial criteria and data interpretation.

In another aspect, the methods provide a prognosis for a subject suffering from endometriosis. In some embodiments, the methods provide a prognosis for choosing a course of treatment in a patient with endometriosis. For example, in one embodiment, the methods are useful for assigning treatment to a patient suffering from endometriosis. By detecting the expression levels of the genes in the composite classifiers described herein, the appropriate treatment can be assigned to the patient. Relevant treatments include, but are not limited to, hormone therapy, chemotherapy, pharmacotherapy, immunotherapy, targeted therapies, and surgical treatment In another aspect, the methods can provide a diagnosis or provide a prognosis for reduced fertility in a patient suffering from endometriosis. For example, the methods of the present invention can be used to assign treatment to a patient with reduced fertility due to endometriosis. Relevant treatments include, but are not limited to, hormone therapy, and surgical treatment.

In another aspect, the methods comprise detecting the expression of genes in a biological sample comprising endometrial cells or tissue, the method comprising detecting the expression level of a plurality of genes in a biological sample comprising endometrial cells from a subject. In some embodiments, the method comprises detecting the expression level of a plurality of genes from at least one set of genes, the set of genes comprising or consisting of the genes in Table 7, Table 8, Table 9, Table 10, Table 11, Table 12, Table 13, Table 14, or Table 15, in a biological sample comprising endometrial cells from a subject. In some embodiments, the method comprises detecting the expression level of all the genes in at least one set of genes, the set of genes comprising or consisting of the genes in Table 7, Table 8, Table 9, Table 10, Table 11, Table 12, Table 13, Table 14, or Table 15, in a biological sample comprising endometrial cells from a subject. In one embodiment, the biological sample comprises cells or tissue from the PE phase of the menstrual cycle. In one embodiment, the biological sample comprises cells or tissue from the ESE phase of the menstrual cycle. In one embodiment, the biological sample comprises cells or tissue from the MSE phase of the menstrual cycle.

In another aspect, the methods are useful for identifying a patient in need of treatment for endometriosis or other uterine pathology. In some embodiments, the methods comprise obtaining a sample comprising endometrial cells or tissue, determining the expression level of at least one set of genes, the set of genes comprising the genes in Table 7, Table 8, Table 9, Table 10, Table 11, Table 12, Table 13, Table 14, or Table 15, in the sample comprising endometrial cells from a subject; and associating the expression level with the presence and severity of endometriosis; thereby identifying a patient in need of treatment for endometriosis or other uterine pathology.

Computer Implemented Methods and Systems

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

Thus, in some embodiments, the present invention provides a computer implemented method for diagnosing endometriosis. In one embodiment, the computer implemented method comprises:

(i) receiving the expression data of at least one set of genes, the set of genes comprising the genes in Table 7, Table 8, Table 9, Table 10, Table 11, Table 12, Table 13, Table 14, and/or Table 15; and (ii) associating the expression data of the at least one set of genes with the presence, absence or severity of endometriosis, thereby diagnosing endometriosis.

In some embodiments, the associating step comprises a margin tree classification method. In some embodiments, the expression data is for some or all of the genes in Tables 7-15. In some embodiments, the method further comprises providing the expression data for the genes to the computer system. Thus, in one embodiment, the method further comprises providing the expression data for some or all of the genes in Tables 7-15 to the computer system.

The computer implemented method can provide the diagnosis to a health care provider or to the patient. In some embodiments, the computer implemented method further comprises providing a course of treatment for a patient diagnosed with endometriosis.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein.

In some embodiments, a system is provided, the system comprising the computer product described above, and one or more processors for executing instructions stored on the computer readable medium.

Figure 4:
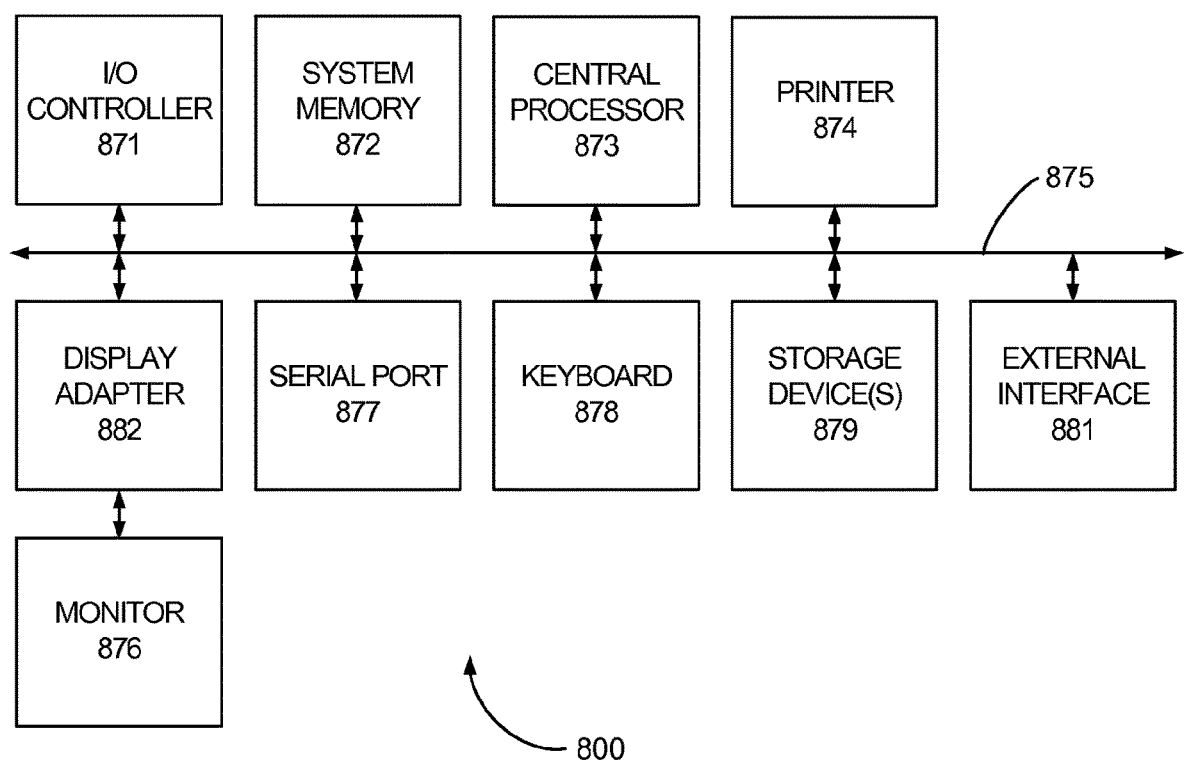
FIG. 4 shows a block diagram of an example computer usable with the system and methods according to embodiments described herein.

FIG. 4 shows a block diagram of an example computer system 800 usable with system and methods according to embodiments of the present invention.

Any of the computer systems mentioned herein may utilize any suitable number of subsystems. Examples of such subsystems are shown in FIG. 4 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 4 are interconnected via a system bus 875. Additional subsystems such as a printer 874, keyboard 878, storage device(s) 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the storage device(s) 879 (e.g., a fixed disk, such as a hard drive or optical disk), as well as the exchange of information between subsystems. The system memory 872 and/or the storage device(s) 879 may embody a computer readable medium. Any of the data mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Biological Samples

In some embodiments, the biological sample is a tissue sample comprising endometrial cells, for example a biopsy comprising endometrial tissue. In some embodiments, the biological sample is a cell preparation comprising endometrial cells. In some embodiments, the biological sample is a cell culture comprising endometrial cells. In one embodiment, the biological sample comprises endometrial cells or endometrial tissue. In some embodiments, the biological sample comprises uterine tissue.

Determining the Expression Level of Genes

Detecting RNA Expression

Methods for detecting the expression of nucleic acids (e.g., mRNA) by the genes described herein are well known in the art. Analysis of nucleic acids can be achieved using routine techniques based on hybridization to a nucleic acid sequence that is complementary to a portion of the gene's coding sequence. For example, nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman® assays, available from, e.g., Applied Biosystems, can be used to detect nucleic acids and variants thereof. In other embodiments, qPCR can be used to detect nucleic acids. Reagents that bind to selected biomarkers can be prepared according to methods known to those of skill in the art or purchased commercially. Applicable PCR amplification techniques are described in Ausubel et al., Short Protocols in Molecular Biology, 5$^{th}$ Edition, Wiley, 2002, and Innis et al., PCR Protocols, Academic Press, 1990. General nucleic acid hybridization methods are described in Anderson, "Nucleic Acid Hybridization," BIOS Scientific Publishers, 1999.

In some embodiments, the expression level of mRNA is determined by hybridization to a nucleic acid microarray.

Microarray methods are generally described in Hardiman, "Microarrays Methods and Applications: Nuts & Bolts," DNA Press, 2003; and Baldi et al., "DNA Microarrays and Gene Expression From Experiments to Data Analysis and Modeling," Cambridge University Press, 2002. In some embodiments, the microarray is an Affymetrix Human Genome microarray. Exemplary conditions for hybridizing mRNA to a microarray include 0.05 μg/μL fragmented cRNA in buffer containing 100 mM 4-Morpholineethanesulfonic acid hydrate, 0.1 mg/mL Herring Sperm DNA, 0.5 mg/mL Acetylated Bovine Serum Albumin, 1 M NaCl, 20 mM EDTA and 0.01% Tween 20, at 45° C. for 16 hours rotating at 60 rpm.

The microarray can comprise a plurality of probe sets, where a probe set is designed to specifically hybridize to one gene in the set of genes. As used herein, a probe set is a collection of two or more probes that are designed to hybridize to a single molecular species, such as a single mRNA. For example, probe set A can comprise two or more probes that specifically hybridize to mRNA expressed by gene A, whereas probe set B can comprise two or more probes that specifically hybridize to mRNA expressed by gene B. Thus, the present disclosure also provides probe sets that can be used to identify products of gene expression in each of the composite classifiers described herein. In some embodiments, the probe sets detect (hybridize to) a transcript from a core gene of a classifier. In some embodiments, the probe sets detect (hybridize to) a transcript from a non-core gene of a classifier. In some embodiments, each probe set is designed to hybridize to different regions of the same transcript. In some embodiments, the probe sets are immobilized on a surface or solid support such as a microarray. In some embodiments, at least 10, 20, 50, 100, 500, 1000, 2000, 5000, 10000, 20000, 30000, 40000, or 50000 probe sets are provided. In one embodiment, at least 54,000 probe sets are provided. Examples of probe sets used to detect expression of the genes described herein are provided in the Examples.

Thus, the instant application provides one or more sets of oligonucleotides that are useful for detecting expression of the genes described herein, including both core and non-core genes. For example, in some embodiments, a set of oligonucleotides is provided that is capable of detecting the expression of each gene in Tables 7-15. In some embodiments, a set of oligonucleotides is provided that is capable of detecting the expression of each gene in Tables 16-18. Each set of oligonucleotides that is capable of detecting the expression of a gene described herein is sometimes referred to as a probe set. In some embodiments, each probe set is designed to specifically hybridize to a single nucleic acid molecule that is expressed by a gene described herein. In some embodiments, each probe set comprises from 10-40 oligonucleotides that are capable of specifically hybridizing, under suitable hybridization conditions, to a nucleic acid expressed by a gene in a classifier, or by a gene in Tables 7-15 or Tables 16-18. Suitable hybridization conditions are well known in the art.

In some embodiments, each probe set comprises 11 probe pairs, where one member of the pair is a perfect match to the complementary target sequence, and the other member of the pair is a mismatch to the complementary target sequence. In some embodiments, the probe sets are Affymetrix® Human Genome U133 probe sets. A probe set can comprise oligonucleotides comprising 12 to 60 contiguous nucleotides that are complementary to a nucleotide sequence, such as an mRNA, that is expressed by a gene in Tables 7-15 or Tables 16-18. In some embodiments, a probe set comprises oligonucleotides comprising 12-60 contiguous nucleotides that are complementary to a cDNA transcribed from an mRNA expressed by a gene in Tables 7-15 or Tables 16-18. In some embodiments, the probe set comprises oligonucleotides comprising 12, 13, 14, 15, 16, 17, 18, 19, 20, 21, 22, 23, 24, 25, 26, 27, 28, 29, 30, 35, 40, 45, 50, 55 or 60 contiguous nucleotides that are complementary to an mRNA (or cDNA transcribed from an mRNA) expressed by a gene in Tables 7-15 or Tables 16-18. In some embodiments, the probe set comprises oligonucleotides having a probe length of 25 contiguous nucleotides. In some embodiments, the instant disclosure provides combinations of probe sets that are capable of detecting the expression of a plurality of genes described herein. In some embodiments, combinations of probe sets comprising 12-60 contiguous nucleotides are provided, where each probe set is complementary to an mRNA or cDNA expressed by at least two or more of the genes in Tables 7-15 or Tables 16-18.

Analysis of nucleic acids and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., Biotechniques, 13:626-633 (1992)), solid-phase sequencing (Zimmerman et al., Methods Mol. Cell Biol., 3:39-42 (1992)), sequencing with mass spectrometry such as matrix-assisted laser desorption/ionization time-of-flight mass spectrometry (MALDI-TOF/MS; Fu et al., Nat. Biotechnol., 16:381-384 (1998)), and sequencing by hybridization. (Chee et al., Science, 274:610-614 (1996); Drmanac et al., Science, 260:1649-1652 (1993); Drmanac et al., Nat. Biotechnol., 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE), pyrosequencing, and next generation sequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Detecting Protein Expression

In some embodiments, the expression level of each gene in a classifier is determined by measuring the amount of protein expressed by each gene in the classifier. In some embodiments, the amount of protein is determined by contacting the protein with an antibody that is specific for the protein of interest. Methods of determining the amount of protein in a sample are well known in the art, as described herein.

Methods for detecting proteins expressed by the genes in the classifier are well known in the art. For example, antibody reagents can be used to detect protein expression levels of the genes of the classifiers in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to proteins can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different markers. Such formats include microarrays and certain capillary devices. See, e.g., Ng et al., J. Cell Mol. Med., 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various genetic markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by endometriosis biomarkers, such as antibodies, may be labeled using an appropriate marker, such as a fluorescent marker.

In some embodiments, the methods detect the expression of secreted proteins that are encoded by the genes in Tables 7-18. Thus, in some embodiments, the biological sample comprises secreted proteins, wherein the sample includes but is not limited to, an endometrial fluid, secretion or lavage, a cervical fluid or lavage, blood, plasma, serum, peritoneal fluid, urine, or saliva.

Kits

In another aspect, the present invention provides compositions, kits and integrated systems for practicing the assays described herein using nucleic acids specific for the polynucleotides or antibodies specific for the polypeptides expressed by the genes described herein. Kits for carrying out the diagnostic assays of the invention typically include a probe that comprises a nucleic acid sequence or an antibody that specifically binds to polynucleotides or polypeptides expressed by genes described herein, and a label for detecting the presence of the probe. In some embodiments, the kits comprise probes that detect expression of one or more of the sets of genes in a classifier described herein. For example, the kits can include probes that detect the expression of genes in a disease classifier, severity classifier, or composite classifier described herein. The kits can include probes that detect expression of at least one of the genes in Tables 7-15, and/or at least one of the genes in Tables 16-18. The kit can include probes that detect nucleic acids expressed by the genes in Tables 7-15 or Tables 16-18, or agents (e.g., antibodies or fragments thereof) that detect proteins expressed by the genes in Tables 7-15 or Tables 16-18. In some embodiments, the kit includes a set of instructions for determining if a tissue sample comprising endometrial cells is from a subject suffering from endometriosis or other uterine or pelvic pathology or has no uterine or pelvic pathology.

Development of an Endometriosis Classifier

The present disclosure provides a classifier for diagnosing endometriosis. The classifier is useful for diagnosing both the presence of endometriosis and the severity of endometriosis with high accuracy. The classifier is also useful for identifying sets of genes whose expression levels can be used for diagnosis of endometriosis.

Overview of Endometriosis Classifier

The diagnostic endometriosis classifier is based on a hierarchy of decisions. As shown in FIG. 1, the diagnostic classifier is a composite of a disease classifier and severity classifier. The composite classifiers are used in the decision tree shown in FIG. 1. The first decision is whether pathology is absent or present. If pathology is absent, then the sample is classified as Normal (No Endometriosis, No Uterine/Pelvic Pathology, also referred to as "NE.NUP"). If pathology is present, then the next decision is about the type of pathology. The sample is classified as either Other (No Endometriosis but other Uterine/Pelvic Condition or Uterine/Pelvic Pathology; also referred to as "NE.UCUP") or Endometriosis ("E"). The presence of pathology and type of pathology decisions are determined using the disease classifier. If the type of pathology is endometriosis, then the third decision is about the severity of endometriosis. The sample is classified as either having minimal-mild endometriosis (E.MinimalMild) or moderate-severe endometriosis (E.ModerateSevere). The severity decision is determined using a binary severity classifier that discriminates between the two classes E.MinimalMild and E.ModerateSevere. The development of diagnostic classifiers for each of these decision steps is described in more detail herein.

Genes of the Classifiers

For each step of the decision tree, a group or set of core genes was identified in each classifier whose expression patterns are diagnostic for a given step in the decision tree. For example, in some embodiments, a family of 2 or more classifiers are provided that are diagnostic for the first step in the decision tree, namely the presence or absence of disease. Classifiers are considered to be in the same family if they are diagnostic for the same step of the decision tree.

A family of classifiers can have the same degree of diagnostic accuracy. In some embodiments, each of the classifiers in a family has the same level of accuracy for a given step of the diagnostic decision tree. In some embodiments, each of the classifiers in the same family contains the same set of core genes. Further, each classifier can contain additional "non-core" genes that may or may not overlap with non-core genes of other classifiers in the same family. In some embodiments, one or more of the classifiers in the same family comprise only the core genes. In some embodiments, one or more of the classifiers in the same family comprise the core genes and other non-core genes.

Likewise, this disclosure provides a family of 2 or more classifiers that are diagnostic for the second step in the decision tree, namely the type of disease (Other Pathology versus Endometriosis). In some embodiments, each of the classifiers in the family contains the same family of core genes. In some embodiments, each of the classifiers in the family has the same level of accuracy for a given step of the diagnostic decision tree. Further, each classifier can contain additional "non-core" genes that may or may not overlap with non-core genes of other classifiers in the same family of classifiers that are diagnostic for the type of disease.

Thus, each classifier comprises a family of core genes that are shared by other classifiers in the family of classifiers diagnostic for the same step of the decision tree (i.e., presence of absence of disease, or Other Pathology versus Endometriosis). It will be understood by those of skill in the art that each classifier has a given level of accuracy for diagnosing endometriosis, and that the core genes and non-core genes will vary based on the level of accuracy desired. Thus, the family of classifiers having 95% accuracy in diagnosing the first step of the decision tree will share the same set of core genes (e.g., core set X), while the set of classifiers having 100% accuracy in diagnosing the first step of the decision tree will share a different set of core genes (e.g., core set Y). The set of core genes X and Y may overlap partially or completely. Likewise, the family of classifiers for a given level of accuracy can have non-core genes that may partially overlap with the non-core genes of other classifiers in the family, and the non-core genes for each family can vary with the level of accuracy achieved or desired.

Disease Classifiers

Disease classifiers were developed that discriminate between three classes: No Endometriosis and No Uterine/Pelvic Pathology or condition ("Control" or NE.NUP); No Endometriosis but other Uterine/Pelvic Condition or Uterine/Pelvic Pathology ("Control Other" or NE.UCUP); and Endometriosis (E). The "other pathology" found in the Control Other group may be pelvic, such as prolapse, or uterine, such as fibroids or adenomyosis.

In order to develop the disease classifiers, a learning set of clinical samples was developed. The learning set comprises tissue samples from patients that were categorized into three groups: No Endometriosis and No Uterine/Pelvic Pathology or condition (NE.NUP); No Endometriosis but other Uterine/Pelvic Condition or Uterine/Pelvic Pathology (NE.UCUP); and Endometriosis (E). The samples were obtained from women at different phases of the menstrual cycle, and were classified into proliferative phase, early secretory phase, or mid-secretory phase.

To develop the diagnostic disease classifiers, gene expression in the biological samples was measured or otherwise detected. In some embodiments, gene expression is detected by determining RNA expression levels in the samples. In one embodiment, gene expression is detected by hybridizing RNA isolated from the samples to a microarray. In some embodiments the microarray data is normalized as described in the Examples. However, gene expression can also be detected using any method known in the art, for example by detecting RNA expression using Northern blots, RT-PCR, or sequencing. In some embodiments, gene expression is detected by determining protein expression in the samples, for example by using antibodies that specifically bind to the target protein(s) present in the biological sample.

Disease Classifiers Based on Menstrual Cycle Phase

In some embodiments, disease classifiers were developed based on the sample's menstrual cycle phase. Thus, in some embodiments, three different varieties of disease classifiers were developed: (i) phase-unrestricted, (ii) phase-restricted, and (iii) phase-specific. The phase-unrestricted classifier was developed with the entire set of samples. The phase-unrestricted classifier uses samples from all phases: proliferative (PE), early secretory (ESE), and mid-secretory (MSE). The phase-restricted classifier was developed with samples from the proliferative (PE) and early secretory (ESE) phases. Thus, the phase-restricted classifier contains samples from both the PE phase and the ESE phase. The phase-specific classifiers were developed with samples from a single phase of the menstrual cycle. Consequently, there are three phase-specific classifiers: PE, ESE, and MSE.

Thus, in some embodiments, the classifier is specific to the proliferative phase of the menstrual cycle. In some embodiments, the classifier is specific to the early secretory phase of the menstrual cycle. In some embodiments, the classifier is specific to the mid secretory phase of the menstrual cycle. In some embodiments, the classifier is independent of cycle phase.

In some embodiments, the three phase-related varieties of disease classifiers produce the decision tree shown in the upper box of FIG. 1. The first decision is whether pathology is absent or present. If pathology is absent, then the sample is classified as Normal (NE.NUP). If pathology is present, then the sample drops to the next level. The second decision is about the type of pathology. The sample is classified as either Other (NE.UCUP) or Endometriosis (E).

The disease classifiers described herein function with high accuracy in diagnosing clinical samples with endometriosis. For example, in some embodiments, phase-restricted classifiers were developed that achieve 100% accuracy in diagnosing endometriosis in samples from combined PE and ESE phases of the menstrual cycle. In some embodiments, phase-specific classifiers were developed that achieve 100% accuracy in diagnosing endometriosis in samples restricted to the PE phase or samples restricted to the ESE phase. In some embodiments, phase-specific classifiers were developed that achieve greater than 90% accuracy in diagnosing endometriosis in samples restricted to the MSE phase. In some embodiments, classifiers capable of diagnosing endometriosis at greater than 90% accuracy were developed using phase-unrestricted samples (i.e., the entire set of samples). Details of the disease classifiers are provided in the Examples.

Further, all three varieties of disease classifier produced the same type of decision tree with similar patterns for the margins between the classes. Thus, the relationships between the classes remain the same whether or not phase is restricted. Therefore, the diagnostic process implied by the decision tree for these three classes is robust with respect to phase. Thus, in some embodiments, endometriosis can be diagnosed by using disease classifiers described herein to first determine whether pathology is absent or present and second to identify the type of pathology (i.e., other uterine/pelvic pathology/condition versus endometriosis).

In one aspect, the present disclosure provides a set of disease classifiers that are diagnostic for endometriosis, wherein each classifier of the set comprises the same set of core genes. In some embodiments, the disease classifier comprises the set of genes in Table 7, the set of genes in Table 8, the set of genes in Table 10, the set of genes in Table 11, the set of genes in Table 13, or the set of genes in Table 14. In some embodiments, the disease classifier comprises expression data for the set of core genes. Thus, in some embodiments, the disease classifier comprises expression data for the set of genes in Table 7, the set of genes in Table 8, the set of genes in Table 10, the set of genes in Table 11, the set of genes in Table 13, or the set of genes in Table 14. In some embodiments, the expression data includes the expression level of a gene in the set of genes. For example, expression data can include the relative expression level of a gene as compared to the level of expression of the gene in a control sample or control group.

Severity Classifiers

Once a sample is classified as from a subject with endometriosis, the present disclosure further provides severity classifiers that discriminate among two classes of endometriosis: Minimal-Mild Endometriosis (E.MinimalMild), and Moderate-Severe Endometriosis (E.ModerateSevere).

Similar to the disease classifiers described above, three phase specific severity classifiers are described herein. The phase-specific severity classifiers were developed using samples from a single phase of the menstrual cycle present in the learning set: either proliferative (PE), early secretory (ESE), or mid-secretory (MSE) phase. Consequently, there are three phase-specific classifiers: PE, ESE, and MSE.

Severity classifiers were developed that function with high accuracy in diagnosing clinical samples with endometriosis. For example, phase-specific severity classifiers were developed that achieve 100% accuracy in diagnosing the severity of endometriosis in the PE phase, the ESE phase, and the MSE phase.

Thus, the present disclosure provides severity classifiers that are diagnostic for minimal-mild endometriosis (E.MinimalMild) and moderate-severe endometriosis (E.ModerateSevere) in samples from the proliferative (PE), early secretory (ESE), and mid-secretory (MSE) phases of the menstrual cycle. Further details of the severity classifiers are provided in the Examples.

Genes of the Severity Classifiers

The present disclosure also provides a set of core genes for each family of severity classifiers whose expression patterns are diagnostic for the phase-specific severity classifiers. In some embodiments, each of the classifiers in the family has the same level of accuracy for diagnosing the severity of endometriosis. In some embodiments, the family of classifiers having the same level of diagnostic accuracy comprises the same set of core genes. Further, each classifier can contain additional "non-core" genes that may or may not overlap with non-core genes of other classifiers in the same family.

Thus, in some embodiments, a family of 2 or more PE phase-specific severity classifiers are provided having 100% accuracy in diagnosing the severity of endometriosis, where each classifier in the family has the same set of core genes. In some embodiments, a family of 2 or more ESE phase-specific severity classifiers are provided having 100% accuracy in diagnosing the severity of endometriosis, where each classifier in the family has the same set of core genes. In some embodiments, a family of 2 or more MSE phasespecific severity classifiers are provided having 100% accuracy in diagnosing the severity of endometriosis, where each classifier in the family has the same set of core genes. In some embodiments, the severity classifier comprises the set of genes in Table 9, the set of genes in Table 12, or the set of genes in Table 15.

Composite Classifiers

In another aspect, the present invention provides composite classifiers that are useful in diagnosing both the presence and severity of endometriosis in a biological sample. The composite classifiers integrate a disease classifier and a severity classifier. Thus, in some embodiments, the composite classifier comprises a disease classifier and a severity classifier. In some embodiments, the composite classifier comprises a disease classifier and a two-class severity classifier.

The disease classifier discriminates among three classes: No Endometriosis and No Pathology (NE.NUP), No Endometriosis but Other Pathology (NE.UCUP), and Endometriosis (E). The disease classifiers were constructed and validated with samples labeled according to this nomenclature. In some embodiments, the endometriosis samples are combined together into one class regardless of severity. If a sample is assigned to the Endometriosis class, then it is passed to a binary severity classifier that discriminates among two classes: Minimal-Mild Endometriosis (E.MinimalMild) and Moderate-Severe Endometriosis (E.ModerateSevere). In some embodiments, the binary severity classifiers are constructed and validated with endometriosis samples explicitly divided into two distinct classes based on severity.

In some embodiments, the composite classifier comprises the set of genes in Table 7, the set of genes in Table 8, the set of genes in Table 9, the set of genes in Table 10, the set of genes in Table 11, the set of genes in Table 12, the set of genes in Table 13, the set of genes in Table 14, or the set of genes in Table 15.

The frequency of occurrence and ranking of importance of each probe set for each phase-specific classifier was also determined. A high frequency of occurrence means that the probe set was present in about 90% or more of the phase-specific classifiers. A low frequency of occurrence means that the probe set was present in about 9% or less of the phase-specific classifiers. This analysis showed that a relatively small number of probe sets occurred in 90% or more of the classifiers, whereas a relatively large number of probe sets occurred in 9% or less of the classifiers. The relatively small number of probe sets that occur with high frequency in the set of classifiers correspond to genes that are diagnostic for endometriosis for each phase-specific classifier. The relatively large number of probe sets that occur with low frequency in the set of classifiers correspond to genes that are most-likely not diagnostic for endometriosis for each phase-specific classifier. The results of the above analysis are provided in the Examples.

Expression of Classifier Genes

The classifiers described herein comprise expression data for the genes in the classifier, including both core and non-core genes. The expression data can comprise measurements of the absolute or relative expression level of the individual genes (core and non-core genes) in each classifier. Thus, in some embodiments, the classifier comprises expression data for each or all of the genes in the classifier, including both core and non-core genes. In some embodiments, the classifier comprises expression data for each of the genes in Tables 7, 8, 9, 10, 11, 12, 13, 14 or 15. In some embodiments, the expression data comprises the expression level for each or all of the genes in the classifier. In some embodiments, the expression data comprises expression levels for each of the genes in Tables 7, 8, 9, 10, 11, 12, 13, 14 or 15.

In some embodiments, the expression level of a gene in a classifier is determined by measuring the amount of RNA transcribed from the gene. In some embodiments, the expression level of a gene in a classifier is determined by hybridizing RNA isolated from a sample to a microarray. In some embodiments, the microarray expression data is normalized such that classifier development occurs within the context of a common basis of normalized intensity values. In some embodiments, the expression level of a gene in a classifier is determined by PCR or RT-PCR.

In some embodiments, the expression level of a gene in a classifier is determined by measuring the amount of protein expressed by the gene In some embodiments, the expression level of a gene in a classifier is determined by measuring the amount of secreted protein expressed by the gene as further described herein.

EXAMPLES

The following examples are offered to illustrate, but not to limit the claims.

Example 1

This example describes the development of classifiers that are useful for diagnosing the presence and severity of endometriosis.

SUMMARY

Endometriosis is a disease wherein endometrium, the tissue lining the uterine cavity, is found outside this normal anatomical location causing inflammation, scarring, pain and infertility. Endometriosis is typically diagnosed at the time of surgery under general anesthesia in the operating room. Herein we describe an exemplary method to diagnose endometriosis by sampling the lining of the uterus, that does not require laparoscopic or open abdominal surgery.

The method was developed utilizing margin tree classification and resampling analyses of global gene expression (transcriptome) data of eutopic endometrium (in its normal uterine location) with a sizeable (n>100) set of meticulously annotated clinical endometrial tissue samples. This methodology led to the discovery of diagnostic classifiers that can determine the presence of endometriosis disease and its severity (stage). Developed classifiers diagnose and stage endometriosis with >90% accuracy, often based on the expression levels of small numbers of genes.

The developed classifiers can detect whether endometriosis or non-endometrial benign uterine/pelvic pathologies (e.g. fibroids, pelvic organ prolapse) are entirely absent or one or more of them are present (e.g. in a patient with pelvic pain), and further discriminate endometriosis from non-endometriosis uterine or pelvic pathologies, as well as determine disease severity in endometriosis. As shown in FIG. 1, the classification algorithm used by the classifiers utilizes three sequential binary decisions that assign: 1. a sample to a disease (i.e., endometriosis or other uterine/pelvic pathology) or no disease category (i.e., no endometriosis and no uterine/pelvic pathology (NE.NUP)); 2. a sample in the disease category further to an endometriosis (E) or other uterine/pelvic pathology (NE.UCUP) category; and 3. a sample in the endometriosis category further to a minimal/mild (E.MinimalMild) or moderate/severe (E.ModerateSevere) category. Each one of these binary decisions or "decision nodes" in the classification process is based on expression levels of distinct sets of genes which are specific for a given node and classifier.

The resampling component of the analysis generates multiple classifiers, each with distinct sets of genes for the three decision nodes, and performing with a defined accuracy. Multiple classifiers produced by resampling of a particular sample set and having the same validation accuracy are herein referred to as a "classifier family". Common genes used for a particular decision node in every single classifier within a family are defined as "core genes" for that particular decision node and classifier family.

We have developed different variants of such classifiers, some diagnosing only samples from a particular phase in the menstrual cycle (i.e. proliferative, early secretory or mid-secretory), and some diagnosing samples from all of these cycle phases. Herein we describe the development of cycle phase-specific and cycle phase-independent diagnostic classifiers for endometriosis, and compile the core genes for the highest accuracy classifier families, corresponding to those diagnosing samples from either the proliferative or early secretory phases of the cycle.

Methods

Tissues Samples and Gene Expression Analysis

Tissues were procured through the NIH SCCPIR Tissue Bank at UCSF following our developed standard operating procedures (SOP) (1). Samples were selected from proliferative, early secretory, and mid-secretory phases of the cycle: without any uterine/pelvic pathology or condition, without endometriosis, minimal-mild endometriosis, and moderate-severe endometriosis. Disease status was verified reviewing all subjects' operative and pathology reports. Cycle phase was assigned by standard histological diagnostic criteria after review by two pathologists, and confirmed by estrogen and progesterone serum levels, clustering in unsupervised principal component analysis of transcriptome data, and cycle phase assignment classifier analysis. Tissue samples were processed under rigorous protocols for RNA isolation, quality assessment, and hybridization to Affymetrix Human Genome U133 Plus 2.0 microarrays at the Gladstone Institute UCSF Genomics Core.

Categories

Samples fall into one of three phases of the menstrual cycle: proliferative, early secretory, or mid-secretory, and one of three disease groups. One group consists of samples from subjects with no endometriosis and no uterine/pelvic pathology (NE.NUP), another group consists of samples from subjects with no endometriosis but other uterine or pelvic pathology (NE.UCUP) such as fibroids, adenomyosis, or pelvic organ prolapse, and the Endometriosis (E) group consists of samples from subjects with the disease. The 144 samples are cross-classified according to cycle phase and group labels in Table 1.

TABLE 1

Cross-classification of samples by phase and group label.

| Group | Proliferative | Early Secretory | Mid Secretory | Row Totals |
|---|---|---|---|---|
| No endometriosis & no uterine/pelvic pathology (NE.NUP) | 20 | 6 | 8 | 34 |
| No endometriosis but uterine/pelvic pathology (NE.UCUP) | 15 | 6 | 14 | 35 |
| Endometriosis (E) | 29 | 18 | 28 | 75 |
| Column Totals | 64 | 30 | 50 | 144 |

For the 75 endometriosis samples, we defined two severity groups: Minimal to Mild (E.Min/Mild) and Moderate to Severe (E.Mod/Severe). Two samples annotated with Undefined severity are only used for disease classifier development (Table 2) and were not used to develop severity classifiers. The 75 samples are cross-classified according to cycle phase and severity labels in Table 2.

TABLE 2

Cross-classification of samples by phase and severity label.

| Severity | Proliferative | Early Secretory | Mid Secretory | Row Totals |
|---|---|---|---|---|
| Minimal to Mild (E.Minimal-Mild) | 11 | 6 | 9 | 26 |
| Moderate to Severe (E.Moderate-Severe) | 17 | 12 | 18 | 47 |
| Undefined | 1 | 0 | 1 | 2 |
| Column Totals | 29 | 18 | 28 | 75 |

Normalization

We performed all data analyses using R and Bioconductor. We simultaneously normalized the microarray data for all 144 samples, which permits all classifier development to occur within the context of a common basis of normalized intensity values. Normalization was conducted using the Bioconductor package GCRMA, appropriate for our data because the Affymetrix HuGene U133 Plus 2.0 microarray has both perfect match and mismatch probes.

The normalization procedure consists of two steps executed with programs in the GCRMA package. First, we compute the probe affinities using the annotation file hgu133plus2cdf provided by Bioconductor for this microarray. The following R code snippet is executed to accomplish this task:

```
Load packages.
     require(affy)
     require(gcrma)
#    Compute affinities once. Save the data and read in for future use.
#    Our microarrays are type HGU133PLUS2.
     affinity.info.hgu133plus2 <- compute.affinities ("hgu133plus2",
verbose=TRUE)
     save(affinity.info.hcm133plus2, file =
"/Volumes/SSD/Classifier/data/affinity.hgu133plus2.Rdata")
```

Second, we normalized the data by setting two options and leaving the rest at default values. The affinity.info option is set to use the probe affinities computed in the first step. The type option is set to fullmodel which uses both the sequence information and mismatch probe model. The following R code snippet is executed to accomplish this task:

```
Load packages.
    require(affy)
    require(gcrma)
#   Use GCRMA for normalization.
    load(file =
    "/Volumes/SSD/Classifier/data/affinity.hgu133plus2.Rdata")
    master.ver07.gcrma <-
    justGCRMA(filenames=master.ver07.df$Filename,
celfile.path='/Volumes/SSD/Microarray_Data/',
phenoData=new("AnnotatedDataFrame", data=master.ver07.df),
affinity.info=affinity.info.hgu133plus2, type='fullmodel')
#   This step is necessary because the colnames attribute of the
ExpressionSet object will use the sample IDs.
    sampleNames(master.ver07.gcrma) <-
    phenoData(master.ver07.gcrma)$Sample
#   Clean up before saving object.
    rm('affinity.info.hgu133plus2')
#   Save GCRMA object.
    save(master.ver07.gcrma, file =
"/Volumes/SSD/Classifier/data/master.ver07.gcrma.Rdata")
```

Classification

The dataset is characterized by extreme asymmetry, having many more variables (54,675 probe sets) than observations (144 samples), and the experimental design presents a multiclass problem with three disease categories for discrimination (NE.NUP, NE.UCUP, E). Therefore, the margin tree classification method of Tibshirani and Hastie (2) was used, which is appropriate for treatment of both these experimental design and dataset features. The problem of classifying more than two classes is resolved into a tree-like sequence of binary decisions. The first binary decision is the presence or absence of pathology wherein the sample is classified as either no pathology or pathology. If pathology is present, the sample passes to the second binary decision (FIG. 1) on the type of pathology wherein the sample is classified as either endometriosis or no endometriosis. A third binary decision is finally added to classify endometriosis samples according to disease severity as either minimal/mild or moderate/severe. The method produces a list of probe sets (i.e. genes) used for each of the three binary decisions: one for the pathology presence/absence decision, one for the pathology type decision, and another for the endometriosis disease stage decision.

Classifier Development

Classifier development was performed using R and Bioconductor. The R package marginTree provides the programs for classifier construction and validation. The R package sampling provides the programs for stratified random sampling. An R script used for actual classifier development is listed in the Appendix section entitled "Sample R Script Illustrating Methodology for Classifier Development".

Figure 2:
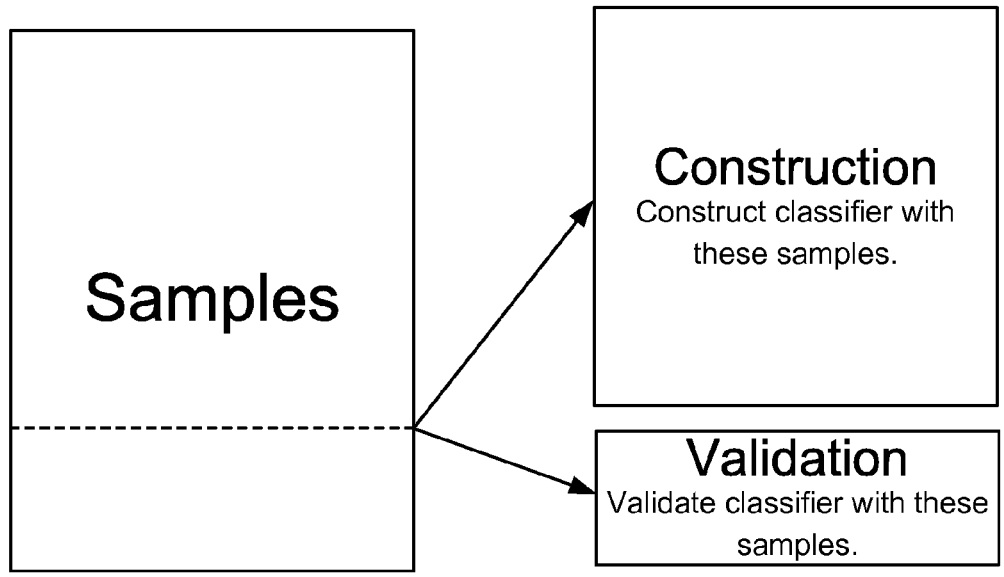
FIG. 2 shows partitioning samples into construction and validation sets.

The sample set is partitioned using stratified random sampling into 80% of samples for construction and the remaining 20% set aside for validation (FIG. 2). The class sizes define the stratification thereby preserving the original proportional representation in both subsets. The construction set is used to build the classifier, and the validation set is used to estimate how well it will perform on new samples to assess the classifier's accuracy.

Figure 3:
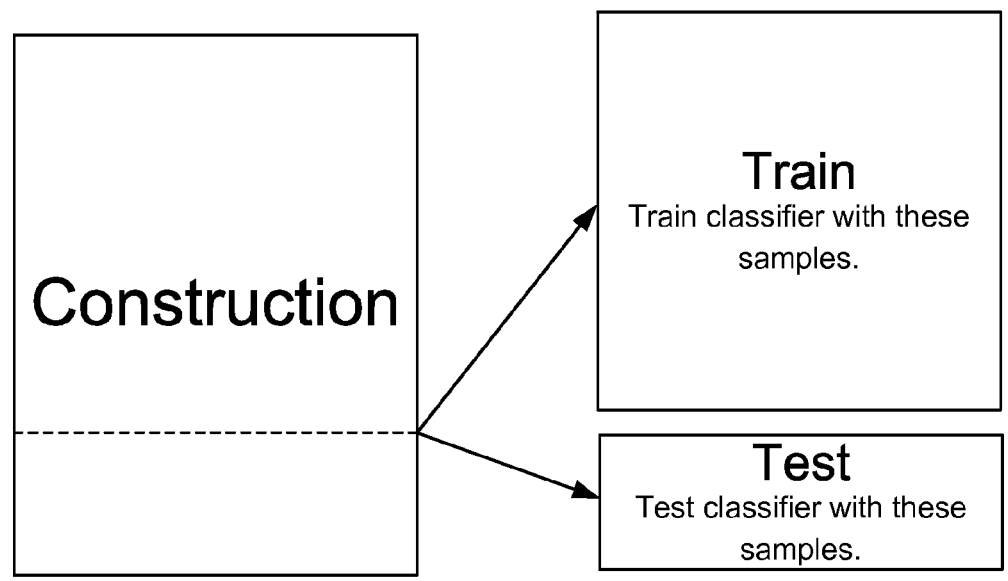
FIG. 3 shows partitioning the construction set into train and test sets.

The construction of the classifier involves building the margin tree, followed by k-fold cross-validation of the margin tree to find the optimal value of the classifier's adjustable parameter. This requires further partitioning of the construction set into k non-overlapping folds (typically k=5 to k=10 folds), each fold preserving the proportional stratification of the original subset. Then k-1 folds are combined into a train set, and the remaining fold is designated as the test set (FIG. 3). The algorithm builds a classifier with the train set and scores its accuracy with the test set. This process is repeated until each fold has been used once as the test set. Upon completion, the optimal value of the margin tree's adjustable parameter is found thereby creating a classifier that best generalizes to new samples. Finally, the validation set (FIG. 2) is used to compute the margin tree's classification accuracy on samples never seen by the classifier during the construction process.

Resampling

The particular composition of the construction and validation subsets upon partitioning of the sample set via random sampling ultimately determines the validation accuracy of the classifier, as well as the composition of the lists of probe sets (i.e. genes) used for each binary decision. If the sample set is partitioned again via random sampling, this will result in different construction and validation subsets which produce a classifier with different validation accuracy, and different gene lists for each binary decision. Thus resampling, i.e. multiple iterations of random partitioning and classifier construction/validation, allows estimating the validation accuracy distribution for the classifiers, and how frequently a gene may be used, as well as its ranking in importance, for a specific binary decision. Multiple classifiers produced by resampling of a particular sample set and having the same validation accuracy are herein referred to as a "classifier family".

Resampling, performed using R, involves setting the number of iterations (250 in this case), and obtaining a series of different prime numbers used as seeds to initialize the random partitioning of samples into construction and validation sets. Ultimately, this resampling process creates 250 classifiers.

Resampling is superimposed upon the classifier development process as shown in the following pseudo-code snippet.

```
FOR iprime in {2, 3, 5, . . . , 1571, 1579, 1583}
    Set seed for pseudo-random number generator (PRNG) equal to
        iprime.
    Use stratified random sampling to partition learning set into
construction and validation subsets.
    Train classifier with construction subset.
    Apply k-fold cross-validation to classifier.
    Score classifier performance with validation subset.
    Save results to output file.
END
```

Diagnostic Classifiers

The strategy developed for optimal efficiency in diagnostic classification is the result of a thorough and systematic investigation of the various analytical alternatives. The end product involves the use of composite classifiers comprising a disease component and a severity component. This allows us to create a robust and complete hierarchy of diagnostic decisions combining the highest accuracy for the various binary decision nodes in the diagnostic tree. This approach results in diagnostic classifier families of high accuracy (e.g., 100%) on validation samples, and comprising large numbers of individual classifiers, which implies robustness. Furthermore, a relatively small number of core genes is used in common by all classifiers within a family for specific binary decision nodes in the diagnostic tree.

Decision Tree

The composite classifiers produce the decision tree shown in FIG. 1. The disease component includes the first two binary decision nodes that segregate the endometriosis samples from the normal and other pathologies. The first decision is whether pathology is absent or present. If pathology is absent the sample is classified as normal (NE.NUP). If pathology is present the sample goes to the next decision level. The second decision determines the type of pathology, the sample classified as either no endometriosis but some other pathology (NE.UCUP) or endometriosis (E). If the type of pathology is endometriosis the severity component assigns the disease stage, and the sample is classified as either Minimal-Mild (E.Min/Mild) or Moderate-Severe Endometriosis (E.Mod/Severe).

Disease Component

Disease classifiers discriminate among three classes: No Endometriosis and No Pathology (NE.NUP), No Endometriosis but Other Pathology (NE.UCUP), and Endometriosis (E). We developed a phase-unrestricted classifier diagnosing all cycle phase categories, a phase-restricted classifier diagnosing samples in both PE and ESE, and three phase-specific classifiers: PE, ESE, and MSE, their respective performances being restricted to only samples of the corresponding cycle phase. The performance of these diagnostic variants of disease classifiers is summarized in Table 3 Table 3. The resampling technique yielded multiple high-accuracy classifiers, the best performing being the PE and ESE phase-specific classifiers that achieved greater than 90% accuracy on validation samples. Altogether a total of 75 of these high accuracy disease classifiers were discovered (Table 3).

TABLE 3

Performance summary of disease classifiers.

| Diagnostic Variant | Cycle Phase | Construction Samples | Validation Samples | Cross-Validation Folds | Classifiers/ Family | Validation Accuracy |
|---|---|---|---|---|---|---|
| Phase-Unrestricted | PE + ESE + MSE | 120 | 28 | 10 | 4 | 93% |
| Phase-Restricted | PE + ESE | 76 | 18 | 10 | 2 | 100% |
| Phase-Specific | PE | 51 | 13 | 10 | 11 | 100% |
|  | ESE | 24 | 6 | 5 | 54 | 100% |
|  | MSE | 39 | 11 | 6 | 4 | 91% |

The characteristics of all discovered individual disease classifiers from all three diagnostic variant families are compiled in Table 4, wherein each discovered classifier is identified by a unique seed number. Listed characteristics for each classifier include the performance accuracy, and the number of probe sets utilized for each one of the two disease classification decisions or "splits": 1) pathology absent or present; 2) pathology present no endometriosis or endometriosis (see FIG. 1). Two individual PE and ESE phase-specific disease classifiers that achieved 100% accuracy using very low (<100) numbers of probe sets for each split were identified (see Table 4).

TABLE 4

Summary of individual disease classifier characteristics.

| Phase | Seed | Accuracy | Decision Pathology Absent or Present No. of Probe Sets Used | Decision Pathology Present Endometriosis or No Endometriosis No. of Probe Sets Used |
|---|---|---|---|---|
| PE.ESE.MSE | 229 | 93% | 8372 | 12704 |
| PE.ESE.MSE | 307 | 93% | 19277 | 29251 |
| PE.ESE.MSE | 479 | 93% | 1579 | 1579 |
| PE.ESE.MSE | 1523 | 93% | 8372 | 12704 |
| PE.ESE | 61 | 100% | 19277 | 23746 |
| PE.ESE | 1447 | 100% | 105 | 845 |
| PE | 2 | 100% | 556 | 685 |
| PE | 79 | 100% | 297 | 685 |
| PE | 173 | 100% | 1282 | 2396 |
| PE | 281 | 100% | 13 | 24 |
| PE | 463 | 100% | 1282 | 3636 |
| PE | 673 | 100% | 241 | 452 |
| PE | 701 | 100% | 845 | 2396 |
| PE | 1021 | 100% | 159 | 452 |
| PE | 1181 | 100% | 159 | 452 |
| PE | 1423 | 100% | 15649 | 15649 |
| PE | 1559 | 100% | 30 | 452 |
| ESE | 3 | 100% | 685 | 685 |
| ESE | 7 | 100% | 685 | 556 |
| ESE | 17 | 100% | 556 | 556 |
| ESE | 19 | 100% | 4479 | 5518 |
| ESE | 71 | 100% | 196 | 241 |
| ESE | 73 | 100% | 12704 | 15649 |
| ESE | 97 | 100% | 8372 | 10313 |
| ESE | 149 | 100% | 685 | 367 |
| ESE | 167 | 100% | 297 | 196 |
| ESE | 179 | 100% | 367 | 241 |
| ESE | 257 | 100% | 297 | 196 |
| ESE | 263 | 100% | 12704 | 15649 |
| ESE | 277 | 100% | 1579 | 1945 |
| ESE | 283 | 100% | 452 | 556 |
| ESE | 389 | 100% | 4479 | 3636 |
| ESE | 419 | 100% | 685 | 685 |
| ESE | 433 | 100% | 5518 | 5518 |
| ESE | 461 | 100% | 367 | 297 |
| ESE | 463 | 100% | 159 | 129 |
| ESE | 509 | 100% | 4479 | 3636 |
| ESE | 563 | 100% | 2396 | 1945 |
| ESE | 593 | 100% | 2952 | 2952 |
| ESE | 631 | 100% | 15649 | 12704 |
| ESE | 653 | 100% | 159 | 297 |
| ESE | 709 | 100% | 241 | 129 |
| ESE | 757 | 100% | 2396 | 2396 |
| ESE | 809 | 100% | 297 | 129 |
| ESE | 827 | 100% | 10313 | 12704 |
| ESE | 857 | 100% | 10313 | 12704 |
| ESE | 881 | 100% | 10313 | 8372 |
| ESE | 887 | 100% | 8372 | 8372 |
| ESE | 907 | 100% | 41822 | 48847 |
| ESE | 937 | 100% | 241 | 297 |
| ESE | 967 | 100% | 3636 | 4479 |
| ESE | 991 | 100% | 685 | 241 |
| ESE | 1031 | 100% | 556 | 452 |
| ESE | 1051 | 100% | 85 | 85 |
| ESE | 1061 | 100% | 6797 | 8372 |
| ESE | 1063 | 100% | 1282 | 1040 |
| ESE | 1091 | 100% | 367 | 241 |
| ESE | 1123 | 100% | 196 | 297 |
| ESE | 1171 | 100% | 12704 | 12704 |
| ESE | 1193 | 100% | 1579 | 1945 |
| ESE | 1213 | 100% | 10313 | 12704 |
| ESE | 1229 | 100% | 452 | 556 |
| ESE | 1277 | 100% | 12704 | 15649 |
| ESE | 1321 | 100% | 241 | 196 |
| ESE | 1367 | 100% | 19277 | 19277 |
| ESE | 1373 | 100% | 1945 | 1945 |
| ESE | 1409 | 100% | 12704 | 10313 |
| ESE | 1423 | 100% | 12704 | 15649 |
| ESE | 1429 | 100% | 297 | 241 |
| ESE | 1471 | 100% | 1945 | 3636 |
| ESE | 1481 | 100% | 3636 | 5518 |

TABLE 4-continued

Summary of individual disease classifier characteristics.

| Phase | Seed | Accuracy | Decision Pathology Absent or Present No. of Probe Sets Used | Decision Pathology Present Endometriosis or No Endometriosis No. of Probe Sets Used |
|---|---|---|---|---|
| MSE | 743 | 91% | 159 | 241 |
| MSE | 1223 | 91% | 845 | 845 |
| MSE | 1367 | 91% | 845 | 1040 |
| MSE | 1499 | 91% | 241 | 452 |

Severity Component

Disease classifiers segregate endometriosis samples into one class regardless of severity. Samples assigned to the Endometriosis class are further analyzed by a binary severity classifier that discriminates among two classes: Minimal-Mild Endometriosis (E.Min/Mild) and Moderate-Severe Endometriosis (E.Mod/Severe). Thus binary severity classifiers are constructed and validated with endometriosis samples explicitly divided into two distinct classes based on severity. We developed binary severity classifiers associated to the >90% accuracy disease classifiers, i.e. PE, ESE, and MSE phase-specific disease classifiers. The performance of these phase-specific severity classifiers is summarized in Table 5. The resampling technique enabled us to discover numerous high-accuracy severity classifiers: 43 PE, 22 ESE, and 44 MSE phase-specific classifiers that achieved 100% accuracy on validation samples (Table 5).

TABLE 5

Performance summary of phase-specific severity classifiers.

| Diagnostic Variant | Cycle Phase | Construction Samples | Validation Samples | Cross-Validation Folds | Classifiers/Family | Validation Accuracy |
|---|---|---|---|---|---|---|
| Phase-Specific | PE | 22 | 6 | 9 | 43 | 100% |
| | ESE | 14 | 4 | 5 | 22 | 100% |
| | MSE | 21 | 6 | 5 | 44 | 100% |

The characteristics of all discovered individual phase-specific severity classifier families are compiled in Table 6, wherein each discovered classifier is identified by a unique seed number. Listed characteristics for each classifier include the performance accuracy, and the number of probe sets utilized to classify endometriosis severity as minimal to mild, or moderate to severe (see FIG. 3). Four of the ESE severity classifiers achieved 100% using very low numbers (<100) of probe sets, while the lowest number utilized by any given PE 100% accuracy severity classifier was 196 probe sets (see Table 6). All of the MSE 100% accuracy severity classifiers discovered utilized more than 1000 probe sets.

TABLE 6

Summary of individual phase-specific severity classifier characteristics.

| Phase | Seed | Accuracy | Decision Endometriosis Minimal-Mild or Moderate-Severe No. of Probe Sets Used |
|---|---|---|---|
| PE | 3 | 100% | 8372 |
| PE | 41 | 100% | 2396 |

TABLE 6-continued

Summary of individual phase-specific severity classifier characteristics.

| Phase | Seed | Accuracy | Decision Endometriosis Minimal-Mild or Moderate-Severe No. of Probe Sets Used |
|---|---|---|---|
| PE | 47 | 100% | 1040 |
| PE | 67 | 100% | 6797 |
| PE | 71 | 100% | 8372 |
| PE | 89 | 100% | 5518 |
| PE | 149 | 100% | 6797 |
| PE | 233 | 100% | 2396 |
| PE | 263 | 100% | 15649 |
| PE | 347 | 100% | 4479 |
| PE | 349 | 100% | 4479 |
| PE | 353 | 100% | 1945 |
| PE | 383 | 100% | 6797 |
| PE | 401 | 100% | 4479 |
| PE | 521 | 100% | 845 |
| PE | 547 | 100% | 6797 |
| PE | 587 | 100% | 2952 |
| PE | 643 | 100% | 19277 |
| PE | 659 | 100% | 6797 |
| PE | 661 | 100% | 5518 |
| PE | 691 | 100% | 556 |
| PE | 757 | 100% | 2952 |
| PE | 787 | 100% | 4479 |
| PE | 857 | 100% | 3636 |
| PE | 907 | 100% | 19277 |
| PE | 947 | 100% | 4479 |
| PE | 983 | 100% | 5518 |
| PE | 1009 | 100% | 845 |
| PE | 1097 | 100% | 2396 |
| PE | 1123 | 100% | 54674 |
| PE | 1153 | 100% | 15649 |
| PE | 1171 | 100% | 1945 |
| PE | 1187 | 100% | 2396 |
| PE | 1193 | 100% | 1282 |
| PE | 1259 | 100% | 5518 |
| PE | 1277 | 100% | 4479 |
| PE | 1381 | 100% | 1282 |
| PE | 1433 | 100% | 1282 |
| PE | 1459 | 100% | 12704 |
| PE | 1481 | 100% | 2952 |
| PE | 1489 | 100% | 2396 |
| PE | 1531 | 100% | 3636 |
| PE | 1567 | 100% | 196 |
| PE | 41 | 100% | 452 |
| ESE | 67 | 100% | 129 |
| ESE | 71 | 100% | 13 |
| ESE | 97 | 100% | 2952 |
| ESE | 101 | 100% | 367 |
| ESE | 157 | 100% | 129 |
| ESE | 181 | 100% | 196 |
| ESE | 271 | 100% | 105 |
| ESE | 293 | 100% | 30 |
| ESE | 331 | 100% | 2952 |
| ESE | 421 | 100% | 452 |
| ESE | 571 | 100% | 196 |
| ESE | 647 | 100% | 129 |
| ESE | 853 | 100% | 367 |
| ESE | 859 | 100% | 367 |
| ESE | 967 | 100% | 13 |
| ESE | 1019 | 100% | 556 |
| ESE | 1171 | 100% | 37 |
| ESE | 1187 | 100% | 1945 |
| ESE | 1259 | 100% | 196 |
| ESE | 1423 | 100% | 105 |
| ESE | 1483 | 100% | 56 |
| MSE | 5 | 100% | 2952 |
| MSE | 7 | 100% | 12704 |
| MSE | 79 | 100% | 2952 |
| MSE | 97 | 100% | 1945 |
| MSE | 101 | 100% | 8372 |
| MSE | 137 | 100% | 1282 |
| MSE | 139 | 100% | 54674 |
| MSE | 149 | 100% | 44385 |

TABLE 6-continued

Summary of individual phase-specific severity classifier characteristics.

| Phase | Seed | Accuracy | Decision Endometriosis Minimal-Mild or Moderate-Severe No. of Probe Sets Used |
|---|---|---|---|
| MSE | 181 | 100% | 8372 |
| MSE | 223 | 100% | 54670 |
| MSE | 257 | 100% | 23746 |
| MSE | 263 | 100% | 2952 |
| MSE | 347 | 100% | 1945 |
| MSE | 389 | 100% | 19277 |
| MSE | 431 | 100% | 4479 |
| MSE | 463 | 100% | 10313 |
| MSE | 467 | 100% | 44385 |
| MSE | 499 | 100% | 4479 |
| MSE | 503 | 100% | 3636 |
| MSE | 619 | 100% | 15649 |
| MSE | 653 | 100% | 5518 |
| MSE | 659 | 100% | 5518 |
| MSE | 683 | 100% | 4479 |
| MSE | 739 | 100% | 44385 |
| MSE | 797 | 100% | 23746 |
| MSE | 881 | 100% | 6797 |
| MSE | 911 | 100% | 6797 |
| MSE | 919 | 100% | 12704 |
| MSE | 937 | 100% | 5518 |
| MSE | 947 | 100% | 19277 |
| MSE | 1019 | 100% | 3636 |
| MSE | 1031 | 100% | 15649 |
| MSE | 1103 | 100% | 1579 |
| MSE | 1153 | 100% | 12704 |
| MSE | 1181 | 100% | 1579 |
| MSE | 1201 | 100% | 10313 |
| MSE | 1297 | 100% | 8372 |
| MSE | 1429 | 100% | 4479 |
| MSE | 1433 | 100% | 12704 |
| MSE | 1439 | 100% | 23746 |
| MSE | 1453 | 100% | 1040 |
| MSE | 1481 | 100% | 54673 |
| MSE | 1487 | 100% | 10313 |
| MSE | 1549 | 100% | 8372 |
| MSE | 1579 | 100% | 3636 |

Core Genes

Each of the binary decisions in the classification process is based on expression levels of distinct sets of genes which are specific for a given binary decision and classifier. The resampling component of the analysis generates multiple classifiers, each with distinct sets of genes for the three binary decisions, and performing at a defined level of accuracy. Classifier families are groups of classifiers produced by resampling of a particular sample set and having the same validation accuracy. Genes used for a particular binary decision in every single classifier within a family are defined as "core genes" for that particular binary decision and classifier family Core genes for the PE, ESE, and MSE phase-specific/>90% accuracy disease and severity classifier families are compiled in Tables 7 through 15.

Phase-Specific PE

Disease Component

TABLE 7

Core genes PE 100% Accuracy Disease Classifier Family: First Binary Decision (NE.NUP vs. E + NE.UCUP).

| Gene. Symbol* | Gene. Title* |
|---|---|
| GenBank: BI547087 | 603190322F1 NIH_MGC_95 *Homo sapiens* cDNA clone IMAGE: 5261717 5-, mRNA sequence |
| GenBank: BG389789 | 602415167F1 NIH_MGC_92 *Homo sapiens* cDNA clone IMAGE: 4523513 5-, mRNA sequence |
| FOSB | FBJ murine osteosarcoma viral oncogene homolog B; GenBank: NM_006732 |
| DIO2 | deiodinase, iodothyronine, type II |
| DDX17 | DEAD (Asp-Glu-Ala-Asp) box polypeptide 17; Genbank Nos: Z97056, AA521056, U59321, AW188131, NM_030881. |
| FOS | FBJ murine osteosarcoma viral oncogene homolog; GenBank: BC004490 |
| MALAT1 | metastasis associated lung adenocarcinoma transcript 1 (non-protein coding) |
| SNTN | sentan, cilia apical structure protein |

*GenBank accession number and definition are provided for non-characterized transcripts.

TABLE 8

Core genes PE 100% Accuracy Disease Classifier Family: Second Binary Decision (NE.UCUP vs. E).

| Gene.Symbol* | Gene.Title* |
|---|---|
| SLC8A1 | solute carrier family 8 (sodium/calcium exchanger), member 1; GenBank: AW452398 |
| LOC728613 | programmed cell death 6 pseudogene |
| LTF | Lactotransferrin; GenBank: NM_002343 |
| HLA-DQA1 | major histocompatibility complex, class II, DQ alpha 1 |
| SLC7A4 | solute carrier family 7 (cationic amino acid transporter, y+ system), member 4; GenBank: NM_004173 |
| PCDH8 | protocadherin 8 |
| CDKN2A | cyclin-dependent kinase inhibitor 2A (melanoma, p16, inhibits CDK4) |
| MUC5B | mucin 5B, oligomeric mucus/gel-forming |
| IQGAP1 | IQ motif containing GTPase activating protein 1 |
| RBM6 | RNA binding motif protein 6 |
| GenBank: AA521056 | aa71e05.s1 NCI_CGAP_GCB1 *Homo sapiens* cDNA clone IMAGE: 826400 3-, mRNA sequence |
| DDX17 | DEAD (Asp-Glu-Ala-Asp) box helicase 17 |
| SCGB3A1 | secretoglobin, family 3A, member 1 |
| GenBank: AW629304 | hi56d01.x1 Soares_NFL_T_GBC_S1 *Homo sapiens* cDNA clone IMAGE: 2976289 3-, mRNA sequence |
| LOC401522 | hypothetical LOC401522 |
| NASP | Nuclear autoantigenic sperm protein (histone-binding) |
| ACTA2 | Actin, alpha 2, smooth muscle, aorta |

*GenBank accession number and definition are provided for non-characterized transcripts.

Severity Component

TABLE 9

Core genes PE 100% Accuracy Severity Classifier Family: E-Min/Mild vs. E-Mod/Severe.

| Gene.Symbol* | Gene.Title* |
|---|---|
| ANLN | anillin, actin binding protein; Genbank: AK023208, NM_018685. |
| LOC142937 | hypothetical protein BC008131 |
| GINS4 | GINS complex subunit 4 (Sld5 homolog) |
| VIM | vimentin |
| LOC100127980 | Hypothetical protein LOC100127980 |

TABLE 9-continued

Core genes PE 100% Accuracy Severity Classifier Family: E-Min/Mild vs. E-Mod/Severe.

| Gene.Symbol* | Gene.Title* |
|---|---|
| GenBank: AI741292 | wg08h02.x1 Soares_NSF_F8_9W_OT_PA_P_S1 *Homo sapiens* cDNA clone IMAGE: 2364531 3-, mRNA sequence |
| GenBank: AL390180 | *Homo sapiens* genomic DNA; cDNA DKFZp761L149 (from clone DKFZp761L149) |
| LOC100505967 | hypothetical LOC100505967 |
| GenBank: AL832142 | *Homo sapiens* mRNA; cDNA DKFZp686A22111 (from clone DKFZp686A22111) |
| GenBank: AK026037 | *Homo sapiens* cDNA: FLJ22384 fis, clone HRC07594 |
| CASP8AP2 | caspase 8 associated protein 2 |
| LTF | lactotransferrin |
| FBN1 | fibrillin 1; Genbank: NM_000138, AW955612. |
| CDH3 | cadherin 3, type 1, P-cadherin (placental) |
| EPHA2 | EPH receptor A2 |
| GSTT1 | glutathione S-transferase theta 1 |
| MAPRE3 | microtubule-associated protein, RP/EB family, member 3 |
| PRKX /// PRKY | protein kinase, X-linked /// protein kinase, Y-linked |
| PRKX | protein kinase, X-linked |
| GSTM4 | glutathione S-transferase mu 4 |
| SLC12A2 | solute carrier family 12 (sodium/potassium/chloride transporters), member 2 |
| GSTM2 | glutathione S-transferase mu 2 (muscle) |
| FOSL1 | FOS-like antigen 1 |
| GSTM1 | glutathione S-transferase mu 1 |
| HSD17B2 | hydroxysteroid (17-beta) dehydrogenase 2 |
| NMT2 | N-myristoyltransferase 2 |
| GABRP | gamma-aminobutyric acid (GABA) A receptor, pi |
| PDZK1 | PDZ domain containing 1 |
| VNN1 | vanin 1 |
| PLCL1 | phospholipase C-like 1 |
| REN | renin |
| CEACAM1 | carcinoembryonic antigen-related cell adhesion molecule 1 (biliary glycoprotein) |
| CRYBB2 /// CRYBB2P1 | crystallin, beta B2 /// crystallin, beta B2 pseudogene 1 |
| SCGB1D2 | secretoglobin, family 1D, member 2 |
| LPHN2 | latrophilin 2 |
| CDKN2A | cyclin-dependent kinase inhibitor 2A (melanoma, p16, inhibits CDK4) |
| SFRP5 | secreted frizzled-related protein 5 |
| D4S234E | DNA segment on chromosome 4 (unique) 234 expressed sequence |
| BMP7 | bone morphogenetic protein 7 |
| MYCN | v-myc myelocytomatosis viral related oncogene, neuroblastoma derived (avian) |
| PTPN11 | protein tyrosine phosphatase, non-receptor type 11 |
| SF1 | splicing factor 1 |
| GZMH | granzyme H (cathepsin G-like 2, protein h-CCPX) |
| FGF18 | fibroblast growth factor 18 |
| PEG10 | paternally expressed 10 |
| SLC7A1 | solute carrier family 7 (cationic amino acid transporter, y+ system), member 1 |
| MUC5B | mucin 5B, oligomeric mucus/gel-forming |
| GenBank: AI345238 | tb81b07.x1 NCI_CGAP_Lu26 *Homo sapiens* cDNA clone IMAGE: 2060725 3-similar to gb: M10119 FERRITIN LIGHT CHAIN (HUMAN);, mRNA sequence |
| CEACAM21 | carcinoembryonic antigen-related cell adhesion molecule 21 |
| GenBank: H92070 | ys84f02.s1 Soares retina N2b4HR *Homo sapiens* cDNA clone IMAGE: 221499 3-similar to contains Alu repetitive element; contains PTR5 repetitive element;, mRNA sequence |
| CALD1 | caldesmon 1 |
| LOC100507804 /// TPSAB1 | tryptase alpha-1-like /// tryptase alpha/beta 1 |
| HYMAI | hydatidiform mole associated and imprinted (non-protein coding) |
| LOC642869 /// SET | SET translocation (myeloid leukemia-associated) pseudogene /// SET nuclear oncogene |
| KIAA1661 | KIAA1661 protein |
| FAM48A | Family with sequence similarity 48, member A |
| BEX1 | brain expressed, X-linked 1 |
| SYBU | syntabulin (syntaxin-interacting) |
| ECEL1 | endothelin converting enzyme-like 1 |
| HELLS | helicase, lymphoid-specific |
| ZBBX | zinc finger, B-box domain containing |
| IQCG | IQ motif containing G |
| KLHL24 | kelch-like 24 (*Drosophila*) |
| LOC389906 | hypothetical LOC389906 |
| LOC100510224 | hypothetical LOC100510224 |
| WHSC1L1 | Wolf-Hirschhorn syndrome candidate 1-like 1 |
| TMEM106B | transmembrane protein 106B |
| GNG12 | guanine nucleotide binding protein (G protein), gamma 12 |
| ENPP3 | ectonucleotide pyrophosphatase/phosphodiesterase 3 |
| FOXP1 | forkhead box P1 |

TABLE 9-continued

Core genes PE 100% Accuracy Severity Classifier Family: E-Min/Mild vs. E-Mod/Severe.

| Gene.Symbol* | Gene.Title* |
| --- | --- |
| PRO2852 | hypothetical protein PRO2852 |
| SECISBP2 | SECIS binding protein 2 |
| MS4A8B | membrane-spanning 4-domains, subfamily A, member 8B |
| MALAT1 | metastasis associated lung adenocarcinoma transcript 1 (non-protein coding) |
| PDK4 | pyruvate dehydrogenase kinase, isozyme 4 |
| SNRPN | small nuclear ribonucleoprotein polypeptide N |
| FAM110C | family with sequence similarity 110, member C |
| LOC100131564 | hypothetical LOC100131564 |
| LOC727820 | hypothetical protein LOC727820 |
| ERAP2 | endoplasmic reticulum aminopeptidase 2 |
| SDCCAG8 | serologically defined colon cancer antigen 8 |
| NKAIN4 | Na+/K+ transporting ATPase interacting 4 |
| GenBank: AA601031 | nk67d10.s1 NCI_CGAP_Sch1 *Homo sapiens* cDNA clone IMAGE: 1018579 3-, mRNA sequence |
| CDC42SE2 | CDC42 small effector 2 |
| EMID2 | EMI domain containing 2 |
| GOLT1A | golgi transport 1A |
| SLC20A1 | solute carrier family 20 (phosphate transporter), member 1 |
| PKHD1L1 | polycystic kidney and hepatic disease 1 (autosomal recessive)-like 1 |
| GenBank: BE858984 | 7g45a06.x1 NCI_CGAP_Pr28 *Homo sapiens* cDNA clone IMAGE: 3309394 3-, mRNA sequence |
| GenBank: AI683621 | tw52g09.x1 NCI_CGAP_Ut1 *Homo sapiens* cDNA clone IMAGE: 2263360 3-, mRNA sequence |
| LOC100506125 | hypothetical LOC100506125 |
| FBXO15 | F-box protein 15 |
| GenBank: AV660825 | AV660825 GLC *Homo sapiens* cDNA clone GLCGLG03 3-, mRNA sequence |
| LOC253039 | hypothetical LOC253039 |
| GenBank: AL157491 | *Homo sapiens* genomic DNA; cDNA DKFZp434K1111 (from clone DKFZp434K1111) |
| GenBank: AF339813 | *Homo sapiens* clone IMAGE: 297403, mRNA sequence |
| SP3 | Sp3 transcription factor |
| GenBank: AU144005 | AU144005 HEMBA1 *Homo sapiens* cDNA clone HEMBA1000622 3-, mRNA sequence |
| GenBank: AF119847 | *Homo sapiens* PRO1550 mRNA, partial cds |
| GenBank: AW297731 | UI-H-BW0-aiy-a-04-0-UI.s1 NCI_CGAP_Sub6 *Homo sapiens* cDNA clone IMAGE: 2730894 3-, mRNA sequence |
| GenBank: BF125564 | 601763318F1 NIH_MGC_20 *Homo sapiens* cDNA clone IMAGE: 4026173 5-, mRNA sequence |
| ILDR1 | immunoglobulin-like domain containing receptor 1 |
| GenBank: AI431345 | ar55f07.x1 Barstead aorta HPLRB6 *Homo sapiens* cDNA clone IMAGE: 2126533 3-, mRNA sequence |
| GenBank: AI732617 | zo89e10.x5 Stratagene ovarian cancer (#937219) *Homo sapiens* cDNA clone IMAGE: 594090 3-, mRNA sequence |
| GenBank: AA228366 | nc39f01.r1 NCI_CGAP_Pr2 *Homo sapiens* cDNA clone IMAGE: 1010521, mRNA sequence |
| UNC5A | unc-5 homolog A (*C. elegans*) |
| GenBank: AW197431 | xm39b03.x1 NCI_CGAP_GC6 *Homo sapiens* cDNA clone IMAGE: 2686541 3-similar to contains element KER repetitive element;, mRNA sequence |
| NAA25 | N(alpha)-acetyltransferase 25, NatB auxiliary subunit |
| GenBank: BE222109 | hu05h12.x1 NCI_CGAP_Lu24 *Homo sapiens* cDNA clone IMAGE: 3165767 3-, mRNA sequence |
| PRKRA | protein kinase, interferon-inducible double stranded RNA dependent activator |
| GenBank: AW205632 | UI-H-BI1-afr-e-09-0-UI.s1 NCI_CGAP_Sub3 *Homo sapiens* cDNA clone IMAGE: 2722673 3-, mRNA sequence |
| RXFP1 | relaxin/insulin-like family peptide receptor 1 |
| GenBank: BF438300 | 7q07e12.x1 NCI_CGAP_Pr28 *Homo sapiens* cDNA clone IMAGE: 3676918 3-, mRNA sequence |
| GenBank: BE295812 | 601176827F1 NIH_MGC_17 *Homo sapiens* cDNA clone IMAGE: 3532039 5-, mRNA sequence |
| FLJ39739 | Hypothetical FLJ39739 |
| GenBank: AW203986 | UI-H-BI1-aeu-f-12-0-UI.s1 NCI_CGAP_Sub3 *Homo sapiens* cDNA clone IMAGE: 2720782 3-, mRNA sequence |
| GenBank: AA908970 | ol10a05.s1 Soares_NFL_T_GBC_S1 *Homo sapiens* cDNA clone IMAGE: 1523024 3-, mRNA sequence |
| TULP4 | Tubby like protein 4 |
| FAM81B | family with sequence similarity 81, member B |
| GenBank: BE349858 | ht05b06.x1 NCI_CGAP_Kid13 *Homo sapiens* cDNA clone IMAGE: 3145811 3-, mRNA sequence |
| GenBank: BF508634 | UI-H-BI4-aop-a-02-0-UI.s1 NCI_CGAP_Sub8 *Homo sapiens* cDNA clone IMAGE: 3085347 3-, mRNA sequence |
| WDR1 | WD repeat domain 1 |

TABLE 9-continued

Core genes PE 100% Accuracy Severity Classifier Family: E-Min/Mild vs. E-Mod/Severe.

| Gene.Symbol* | Gene.Title* |
| --- | --- |
| GenBank: BE467916 | hz75g08.x1 NCI_CGAP_Lu24 *Homo sapiens* cDNA clone IMAGE: 3213854 3-, mRNA sequence |
| C21orf121 | chromosome 21 open reading frame 121 |
| GenBank: R68807 | yi43b01.s1 Soares placenta Nb2HP *Homo sapiens* cDNA clone IMAGE: 141961 3-, mRNA sequence |
| GenBank: AW117264 | xd86f06.x1 Soares_NFL_T_GBC_S1 *Homo sapiens* cDNA clone IMAGE: 2604515 3-, mRNA sequence |
| NUPL1 | nucleoporin like 1 |
| LOC400931 | hypothetical LOC400931 |
| GenBank: AW962458 | EST374531 MAGE resequences, MAGG *Homo sapiens* cDNA, mRNA sequence |
| QKI | Quaking homolog, KH domain RNA binding (mouse) |
| GenBank: AW976631 | EST388740 MAGE resequences, MAGN *Homo sapiens* cDNA, mRNA sequence |
| GenBank: AA608834 | af03h05.s1 Soares_testis_NHT *Homo sapiens* cDNA clone IMAGE: 1030617 3-, mRNA sequence |
| SNRPA1 | Small nuclear ribonucleoprotein polypeptide A' |
| TMF1 | TATA element modulatory factor 1 |
| IREB2 | iron-responsive element binding protein 2 |
| ASXL1 | additional sex combs like 1 (*Drosophila*) |
| GenBank: BF055144 | 7j75e02.x1 Soares_NSF_F8_9W_OT_PA_P_S1 *Homo sapiens* cDNA clone IMAGE: 3392282 3-, mRNA sequence |
| LRPAP1 | low density lipoprotein receptor-related protein associated protein 1 |
| GenBank: N39188 | yv26d08.s1 Soares fetal liver spleen 1NFLS *Homo sapiens* cDNA clone IMAGE: 243855 3-similar to contains Alu repetitive element; contains element MER35 repetitive element;, mRNA sequence |
| GenBank: AI650364 | wa90a01.x1 NCI_CGAP_GC6 *Homo sapiens* cDNA clone IMAGE: 2303400 3-similar to contains Alu repetitive element;, mRNA sequence |
| GenBank: AI467945 | tj84d07.x1 Soares_NSF_F8_9W_OT_PA_P_S1 *Homo sapiens* cDNA clone IMAGE: 2148205 3-, mRNA sequence |
| GenBank: AA682674 | zj20h10.s1 Soares_fetal_liver_spleen_1NFLS_S1 *Homo sapiens* cDNA clone IMAGE: 450883 3-, mRNA sequence |
| RAB18 | RAB18, member RAS oncogene family |
| GJC1 | gap junction protein, gamma 1, 45 kDa |
| CMIP | C-Maf-inducing protein |
| GenBank: AV691872 | AV691872 GKC *Homo sapiens* cDNA clone GKCDSB09 5-, mRNA sequence |
| GenBank: AW972881 | EST384976 MAGE resequences, MAGL *Homo sapiens* cDNA, mRNA sequence |

*GenBank accession number and definition are provided for non-characterized transcripts.

Phase-Specific ESE
Disease Component

TABLE 10

Core genes ESE 100% Accuracy Disease Classifier Family: First Binary Decision (NE.NUP vs. E + NE.UCUP).

| Gene.Symbol* | Gene.Title* |
| --- | --- |
| LYZ | Lysozyme; Genbank: AV711904, U25677. |
| POSTN | periostin, osteoblast specific factor |
| LOC201651 | similar to arylacetamide deacetylase (AADAC) |
| APOD | apolipoprotein D |
| FOSB | FBJ murine osteosarcoma viral oncogene homolog B |
| S100A8 | S100 calcium binding protein A8 |
| HBG1 /// HBG2 | hemoglobin, gamma A /// hemoglobin, gamma G |
| BAI3 | brain-specific angiogenesis inhibitor 3 |
| CST1 | cystatin SN |
| CST4 | cystatin S |
| SF1 | splicing factor 1 |
| CXCL14 | chemokine (C—X—C motif) ligand 14 |
| TAF7L | TAF7-like RNA polymerase II, TATA box binding protein (TBP)-associated factor, 50 kDa |
| CORIN | corin, serine peptidase |
| IL17RB | interleukin 17 receptor B |
| GDAP1 | ganglioside-induced differentiation-associated protein 1 |
| MUC15 | mucin 15, cell surface associated |
| EGR1 | Early growth response 1 |
| LRRC3B | leucine rich repeat containing 3B |
| EPHB1 | EPH receptor B1 |

TABLE 10-continued

Core genes ESE 100% Accuracy Disease Classifier Family: First Binary Decision
(NE.NUP vs. E + NE.UCUP).

| Gene.Symbol* | Gene.Title* |
| --- | --- |
| GenBank: AA151917 | zo02d03.s1 Stratagene colon (#937204) *Homo sapiens* cDNA clone IMAGE: 566501 3-, mRNA sequence |
| GenBank: AL137429 | *Homo sapiens* mRNA; cDNA DKFZp761C0524 (from clone DKFZp761C0524) |
| GenBank: AA569225 | nm30h11.s1 NCI_CGAP_Lip2 *Homo sapiens* cDNA clone IMAGE: 1061733, mRNA sequence |
| PTEN | phosphatase and tensin homolog |
| GenBank: AA523939 | ng24h09.s1 NCI_CGAP_Co3 *Homo sapiens* cDNA clone IMAGE: 935777 3-, mRNA sequence |
| GenBank: AA826176 | od60e07.s1 NCI_CGAP_GCB1 *Homo sapiens* cDNA clone IMAGE: 1372356 3-, mRNA sequence |
| TMEM132B | transmembrane protein 132B |
| NCKAP5 | NCK-associated protein 5 |
| GenBank: BF001514 | 7g89c05.x1 NCI_CGAP_Co16 *Homo sapiens* cDNA clone IMAGE: 3313640 3-, mRNA sequence |
| GenBank: R36546.1 | yh89f11.s1 Soares placenta Nb2HP *Homo sapiens* cDNA clone IMAGE: 136941 3-, mRNA sequence |
| GenBank: T70087.1 | yc17g11.s1 Stratagene lung (#937210) *Homo sapiens* cDNA clone IMAGE: 80996 3-, mRNA sequence |
| NAMPT | Nicotinamide phosphoribosyltransferase |
| GenBank: AW975013 | EST387118 MAGE resequences, MAGN *Homo sapiens* cDNA, mRNA sequence |
| NUS1P3 | nuclear undecaprenyl pyrophosphate synthase 1 homolog (*S. cerevisiae*) pseudogene 3 |

*GenBank accession number and definition are provided for non-characterized transcripts.

TABLE 11

Core genes ESE 100% Accuracy Disease Classifier Family: Second Binary
Decision (NE.UCUP vs. E).

| Gene.Symbol* | Gene.Title* |
| --- | --- |
| CEL /// LOC100508206 | carboxyl ester lipase (bile salt-stimulated lipase) /// bile salt-activated lipase-like |
| GenBank: BQ024490 | UI-1-BB1p-aut-f-08-0-UI.s1 NCI_CGAP_PI6 *Homo sapiens* cDNA clone UI-1-BB1p-aut-f-08-0-UI 3-, mRNA sequence |
| GenBank: BU955063 | AGENCOURT_10609489 NIH_MGC_126 *Homo sapiens* cDNA clone IMAGE: 6726950 5-, mRNA sequence |
| THBS1 | thrombospondin 1; Genbank Nos: BF109732, AW956580, BF084105, AI812030, NM_003246, BF055462, AV726673. |
| HBA1 /// HBA2 | hemoglobin, alpha 1 /// hemoglobin, alpha 2 |
| CD52 | CD52 molecule |
| CFTR | cystic fibrosis transmembrane conductance regulator (ATP-binding cassette sub-family C, member 7) |
| GSTT2 | glutathione S-transferase theta 2 |
| GPR64 | G protein-coupled receptor 64; Genbank: NM_005756. |
| CRISP3 | cysteine-rich secretory protein 3 |
| HBB | hemoglobin, beta |
| SLC9A3R2 | solute carrier family 9 (sodium/hydrogen exchanger), member 3 regulator 2 |
| ART3 | ADP-ribosyltransferase 3 |
| HIST1H2BG | histone cluster 1, H2bg |
| OLFM4 | olfactomedin 4 |
| SOS1 | son of sevenless homolog 1 (*Drosophila*) |
| MUC5B | mucin 5B, oligomeric mucus/gel-forming |
| GAL | galanin prepropeptide |
| IFI44 | interferon-induced protein 44 |
| ODAM | odontogenic, ameloblast asssociated |
| CATSPERB | cation channel, sperm-associated, beta |
| AGTR2 | angiotensin II receptor, type 2 |
| C15orf48 | chromosome 15 open reading frame 48 |
| PPP1R1B | protein phosphatase 1, regulatory (inhibitor) subunit 1B |
| ZG16B | zymogen granule protein 16 homolog B (rat) |
| C20orf54 | chromosome 20 open reading frame 54 |
| GenBank: AA601031 | nk67d10.s1 NCI_CGAP_Sch1 *Homo sapiens* cDNA clone IMAGE: 1018579 3-, mRNA sequence |
| GenBank: AI147867 | qb34a07.x1 Soares_pregnant_uterus_NbHPU *Homo sapiens* cDNA clone IMAGE: 1698132 3-, mRNA sequence |
| GenBank: AW297731 | UI-H-BW0-aiy-a-04-0-UI.s1 NCI_CGAP_Sub6 *Homo sapiens* cDNA clone IMAGE: 2730894 3-, mRNA sequence |
| CCDC58 | coiled-coil domain containing 58 |

TABLE 11-continued

Core genes ESE 100% Accuracy Disease Classifier Family: Second Binary Decision (NE.UCUP vs. E).

| Gene.Symbol* | Gene.Title* |
|---|---|
| GenBank: BF003148 | 7g55h08.x1 NCI_CGAP_Pr28 Homo sapiens cDNA clone IMAGE: 3310431 3-, mRNA sequence |
| GenBank: BF508634 | UI-H-BI4-aop-a-02-0-UI.s1 NCI_CGAP_Sub8 Homo sapiens cDNA clone IMAGE: 3085347 3-, mRNA sequence |
| GenBank: AI672553 | wb32f06.x1 NCI_CGAP_GC6 Homo sapiens cDNA clone IMAGE: 2307395 3-, mRNA sequence |
| GenBank: AA121544 | zk89g09.s1 Soares_pregnant_uterus_NbHPU Homo sapiens cDNA clone IMAGE: 490048 3-similar to contains element PTR5 repetitive element;, mRNA sequence |

*GenBank accession number and definition are provided for non-characterized transcripts.

Severity Component

TABLE 12

Core genes ESE 100% Accuracy Severity Classifier Family: E-Min/Mild vs. E-Mod/Severe.

| Gene.Symbol | Gene.Title |
|---|---|
| IGF2 /// INS-IGF2 | insulin-like growth factor 2 (somatomedin A) /// INS-IGF2 readthrough transcript |
| FOSB | FBJ murine osteosarcoma viral oncogene homolog B |
| ALPP | alkaline phosphatase, placental |
| MSLN | mesothelin |
| CPA3 | carboxypeptidase A3 (mast cell) |
| PROK1 | prokineticin 1; Genbank: AW183087 |
| PHACTR2 | phosphatase and actin regulator 2 |

Phase-Specific MSE

Disease Component

TABLE 13

Core genes MSE 91% Accuracy Disease Classifier Family: First Binary Decision (NE.NUP vs. E + NE.UCUP).

| Gene Symbol | Gene Title |
|---|---|
| JAK1 | Janus kinase 1 |
| PHF21A | PHD finger protein 21A |
| CTNNB1 | catenin (cadherin-associated protein), beta 1, 88 kDa |
| CBX3 | chromobox homolog 3; Genbank: NM_016587 |
| SLC39A6 | solute carrier family 39 (zinc transporter), member 6 |
| CP | ceruloplasmin (ferroxidase) |
| LUZP1 | leucine zipper protein 1 |
| ADAMTS5 | ADAM metallopeptidase with thrombospondin type 1 motif, 5 |
| CLIP1 | CAP-GLY domain containing linker protein 1 |
| SOCS2-AS1 | SOCS2 antisense RNA 1 (non-protein coding) |
| CACNB2 | calcium channel, voltage-dependent, beta 2 subunit |
| NMRK1 | nicotinamide riboside kinase 1 |
| RARA | retinoic acid receptor, alpha |
| MACC1 | metastasis associated in colon cancer 1 |
| ACTR2 | ARP2 actin-related protein 2 homolog (yeast) |
| RERE | arginine-glutamic acid dipeptide (RE) repeats |
| JUNB | jun B proto-oncogene |
| EGR1 | early growth response 1 |
| TBL1X | transducin (beta)-like 1X-linked |
| PKP4 | plakophilin 4 |
| MX1 | myxovirus (influenza virus) resistance 1, interferon-inducible protein p78 (mouse) |
| TACSTD2 | tumor-associated calcium signal transducer 2 |
| SERPINE1 | serpin peptidase inhibitor, clade E (nexin, plasminogen activator inhibitor type 1), member 1 |
| EFNB2 | ephrin-B2 |
| FOSB | FBJ murine osteosarcoma viral oncogene homolog B |
| MMP14 | matrix metallopeptidase 14 (membrane-inserted) |
| PRDM2 | PR domain containing 2, with ZNF domain |
| PSD3 | pleckstrin and Sec7 domain containing 3 |
| DIO2 | deiodinase, iodothyronine, type II |
| AQP3 | aquaporin 3 (Gill blood group) |
| SLC4A4 | solute carrier family 4, sodium bicarbonate cotransporter, member 4 |
| HBA1 /// HBA2 | hemoglobin, alpha 1 /// hemoglobin, alpha 2 |
| POMZP3 /// ZP3 | POM121 and ZP3 fusion /// zona pellucida glycoprotein 3 (sperm receptor); Genbank: NM_012230 |
| EEA1 | early endosome antigen 1 |
| MSLN | mesothelin |

TABLE 13-continued

Core genes MSE 91% Accuracy Disease Classifier Family: First Binary Decision (NE.NUP vs. E + NE.UCUP).

| Gene Symbol | Gene Title |
| --- | --- |
| LYPD3 | LY6/PLAUR domain containing 3 |
| FGB | fibrinogen beta chain |
| ENPP1 | ectonucleotide pyrophosphatase/phosphodiesterase 1 |
| CLEC3B /// EXOSC7 | C-type lectin domain family 3, member B /// exosome component 7 |
| IGFBP1 | insulin-like growth factor binding protein 1 |
| KLK11 | kallikrein-related peptidase 11 |
| PIP5K1B | phosphatidylinositol-4-phosphate 5-kinase, type I, beta |
| MMP10 | matrix metallopeptidase 10 (stromelysin 2) |
| GPR64 | G protein-coupled receptor 64 |
| LEFTY2 | left-right determination factor 2 |
| CST1 | cystatin SN |
| SPINK1 | serine peptidase inhibitor, Kazal type 1 |
| PRLR | prolactin receptor |
| EPYC | epiphycan |
| CYP24A1 | cytochrome P450, family 24, subfamily A, polypeptide 1 |
| TRPC6 | transient receptor potential cation channel, subfamily C, member 6 |
| SOGA1 | suppressor of glucose, autophagy associated 1 |
| CRISP3 | cysteine-rich secretory protein 3 |
| CDC42 | cell division cycle 42 (GTP binding protein, 25 kDa) |
| CADM1 | cell adhesion molecule 1 |
| HBB | hemoglobin, beta |
| FOS | FBJ murine osteosarcoma viral oncogene homolog |
| CHI3L1 | chitinase 3-like 1 (cartilage glycoprotein-39) |
| ABAT | 4-aminobutyrate aminotransferase |
| CTSZ | cathepsin Z |
| UPK1B | uroplakin 1B |
| POMZP3 | POM121 and ZP3 fusion; Genbank: BC000487 |
| IL6ST | interleukin 6 signal transducer (gp130, oncostatin M receptor) |
| NF1 | neurofibromin 1 |
| DHX9 | DEAH (Asp-Glu-Ala-His) box polypeptide 9 |
| EIF1 | eukaryotic translation initiation factor 1 |
| SECISBP2L | SECIS binding protein 2-like |
| MFAP4 | microfibrillar-associated protein 4 |
| SOS1 | son of sevenless homolog 1 (*Drosophila*) |
| MFAP5 | microfibrillar associated protein 5 |
| LRRC15 | leucine rich repeat containing 15 |
| SST | somatostatin |
| ID2 /// ID2B | inhibitor of DNA binding 2, dominant negative helix-loop-helix protein /// inhibitor of DNA binding 2B, dominant negative helix-loop-helix protein (pseudogene) |
| CTBP1 | C-terminal binding protein 1 |
| CYP2C9 | cytochrome P450, family 2, subfamily C, polypeptide 9 |
| HSPA12A | heat shock 70 kDa protein 12A |
| TWISTNB | TWIST neighbor |
| GUSBP3 /// GUSBP9 /// SMA4 /// SMA5 | glucuronidase, beta pseudogene 3 /// glucuronidase, beta pseudogene 9 /// glucuronidase, beta pseudogene /// glucuronidase, beta pseudogene |
| DYRK1B | dual-specificity tyrosine-(Y)-phosphorylation regulated kinase 1B |
| ATP13A3 | ATPase type 13A3 |
| CHODL | chondrolectin |
| ALDH8A1 | aldehyde dehydrogenase 8 family, member A1 |
| TGFB2 | transforming growth factor, beta 2 |
| SETD2 | SET domain containing 2 |
| UGCG | UDP-glucose ceramide glucosyltransferase |
| ABHD2 | abhydrolase domain containing 2 |
| VPS35 | vacuolar protein sorting 35 homolog (*S. cerevisiae*) |
| ZCCHC2 | zinc finger, CCHC domain containing 2 |
| TEX101 | testis expressed 101 |
| NUPL1 | nucleoporin like 1 |
| ANGPTL1 | angiopoietin-like 1 |
| LOC100507645 /// MALAT1 | uncharacterized LOC100507645 /// metastasis associated lung adenocarcinoma transcript 1 (non-protein coding) |
| WASF2 | WAS protein family, member 2 |
| CPEB4 | cytoplasmic polyadenylation element binding protein 4 |
| SLAIN2 | SLAIN motif family, member 2 |
| BTBD7 | BTB (POZ) domain containing 7 |
| EDIL3 | EGF-like repeats and discoidin I-like domains 3 |
| FBXO32 | F-box protein 32 |
| CUX1 | cut-like homeobox 1 |
| ITGB6 | integrin, beta 6 |
| ZNF800 | zinc finger protein 800 |
| C12orf35 | chromosome 12 open reading frame 35 |
| HS3ST3B1 | heparan sulfate (glucosamine) 3-O-sulfotransferase 3B1 |
| LOC100653132 | uncharacterized LOC100653132 |

TABLE 13-continued

Core genes MSE 91% Accuracy Disease Classifier Family: First Binary Decision (NE.NUP vs. E + NE.UCUP).

| Gene Symbol | Gene Title |
| --- | --- |
| MALAT1 | metastasis associated lung adenocarcinoma transcript 1 (non-protein coding) |
| SORCS1 | sortilin-related VPS10 domain containing receptor 1 |
| CAPN8 | calpain 8 |
| IHH | Indian hedgehog |
| DDX17 | DEAD (Asp-Glu-Ala-Asp) box helicase 17 |
| FER | fer (fps/fes related) tyrosine kinase |
| U2AF1 | U2 small nuclear RNA auxiliary factor 1 |
| LOC100287497 /// LOC100287934 | uncharacterized LOC100287497 /// uncharacterized LOC100287934 |
| BOD1L1 | biorientation of chromosomes in cell division 1-like 1 |
| RAB12 | RAB12, member RAS oncogene family |
| GALNTL2 | UDP-N-acetyl-alpha-D-galactosamine:polypeptide N-acetylgalactosaminyltransferase-like 2 |
| LOC100505989 | uncharacterized LOC100505989 |
| LOC100506582 | uncharacterized LOC100506582 |
| CLK4 | CDC-like kinase 4 |
| HECTD1 | HECT domain containing E3 ubiquitin protein ligase 1 |
| ZNF24 | Zinc finger protein 24 |
| PHKB | phosphorylase kinase, beta |
| NIPBL | Nipped-B homolog (*Drosophila*) |
| TMED8 | transmembrane emp24 protein transport domain containing 8 |
| PHACTR2 | phosphatase and actin regulator 2 |

TABLE 14

Core genes MSE 91% Accuracy Disease Classifier Family: Second Binary Decision (NE.UCUP vs. E).

| Gene Symbol | Gene Title |
| --- | --- |
| CDC42SE2 | CDC42 small effector 2; Genbank: NM_020240 |
| CDYL2 | chromodomain protein, Y-like 2 |
| WBSCR27 | Williams Beuren syndrome chromosome region 27 |
| CEL | carboxyl ester lipase (bile salt-stimulated lipase) |
| NT5E | 5'-nucleotidase, ecto (CD73) |
| C1orf210 | chromosome 1 open reading frame 210 |
| ZBED1 | zinc finger, BED-type containing 1 |
| CYP4B1 | cytochrome P450, family 4, subfamily B, polypeptide 1 |
| LINC00476 | long intergenic non-protein coding RNA 476 |
| CP | ceruloplasmin (ferroxidase) |
| LOC201477 | uncharacterized LOC201477 |
| SLC8A1 | solute carrier family 8 (sodium/calcium exchanger), member 1 |
| SYTL3 | synaptotagmin-like 3 |
| DEFB124 | defensin, beta 124 |
| SERPINE1 | serpin peptidase inhibitor, clade E (nexin, plasminogen activator inhibitor type 1), member 1 |
| DACT2 | dapper, antagonist of beta-catenin, homolog 2 (*Xenopus laevis*) |
| BCLAF1 | BCL2-associated transcription factor 1 |
| ATP1B1 | ATPase, Na+/K+ transporting, beta 1 polypeptide |
| LTF | lactotransferrin |
| CPNE3 | copine III |
| ITPR2 | inositol 1,4,5-trisphosphate receptor, type 2 |
| S100A8 | S100 calcium binding protein A8 |
| STMN2 | stathmin-like 2 |
| MYO6 | myosin VI |
| ATXN1 | ataxin 1 |
| HLA-DQA1 | major histocompatibility complex, class II, DQ alpha 1 |
| F13A1 | coagulation factor XIII, A1 polypeptide |
| ABP1 | amiloride binding protein 1 (amine oxidase (copper-containing)) |

TABLE 14-continued

Core genes MSE 91% Accuracy Disease Classifier Family: Second Binary Decision (NE.UCUP vs. E).

| Gene Symbol | Gene Title |
| --- | --- |
| FGFR2 | fibroblast growth factor receptor 2 |
| PLA2G2A | phospholipase A2, group IIA (platelets, synovial fluid) |
| HMOX1 | heme oxygenase (decycling) 1 |
| PRKAR2B | protein kinase, cAMP-dependent, regulatory, type II, beta |
| PCYOX1 | prenylcysteine oxidase 1 |
| PCCA | propionyl CoA carboxylase, alpha polypeptide |
| VCAM1 | vascular cell adhesion molecule 1 |
| HNMT | histamine N-methyltransferase |
| POMZP3 /// ZP3 | POM121 and ZP3 fusion /// zona pellucida glycoprotein 3 (sperm receptor) |
| S100A2 | S100 calcium binding protein A2 |
| FGFR3 | fibroblast growth factor receptor 3 |
| KYNU | kynureninase |
| ACPP | acid phosphatase, prostate |
| MMP1 | matrix metallopeptidase 1 (interstitial collagenase) |
| MAL | mal, T-cell differentiation protein |
| ORM1 | orosomucoid 1; Genbank: NM_000607 |
| ORM1 /// ORM2 | orosomucoid 1 /// orosomucoid 2; Genbank: NM_000607 /// NM_000608. |
| CFTR | cystic fibrosis transmembrane conductance regulator (ATP-binding cassette sub-family C, member 7) |
| PSPH | phosphoserine phosphatase |
| SLC26A2 | solute carrier family 26 (sulfate transporter), member 2 |
| CXCL13 | chemokine (C—X—C motif) ligand 13 |
| TMSB15A /// TMSB15B | thymosin beta 15a /// thymosin beta 15B |
| MST1R | macrophage stimulating 1 receptor (c-met-related tyrosine kinase) |
| PPP1R1A | protein phosphatase 1, regulatory (inhibitor) subunit 1A |
| PCSK5 | proprotein convertase subtilisin/kexin type 5 |
| RASGRP1 | RAS guanyl releasing protein 1 (calcium and DAG-regulated) |
| MMP10 | matrix metallopeptidase 10 (stromelysin 2) |
| BCL2A1 | BCL2-related protein A1 |
| ABLIM3 | actin binding LIM protein family, member 3 |
| CYP3A5 | cytochrome P450, family 3, subfamily A, polypeptide 5 |
| LEFTY2 | left-right determination factor 2 |
| CST1 | cystatin SN |
| SPINK1 | serine peptidase inhibitor, Kazal type 1 |
| GRP | gastrin-releasing peptide |
| SLC1A1 | solute carrier family 1 (neuronal/epithelial high affinity glutamate transporter, system Xag), member 1 |
| CDH16 | cadherin 16, KSP-cadherin |
| GAGE12B /// GAGE12C /// GAGE12D /// GAGE12E /// GAGE12F /// GAGE12G /// GAGE12H /// GAGE12I /// GAGE2A /// GAGE2B /// GAGE2C /// GAGE4 /// GAGE5 /// GAGE6 /// GAGE7 | G antigen 12B /// G antigen 12C /// G antigen 12D /// G antigen 12E /// G antigen 12F /// G antigen 12G /// G antigen 12H /// G antigen 12I /// G antigen 2A /// G antigen 2B /// G antigen 2C /// G antigen 4 /// G antigen 5 /// G antigen 6 /// G antigen 7 |
| HOXC6 | homeobox C6 |
| NFIC | nuclear factor I/C (CCAAT-binding transcription factor) |
| GABRA2 | gamma-aminobutyric acid (GABA) A receptor, alpha 2 |
| CSF2RA | colony stimulating factor 2 receptor, alpha, low-affinity (granulocyte-macrophage) |
| GAGE1 /// GAGE12B /// GAGE12C /// GAGE12D /// GAGE12E /// GAGE12F /// GAGE12G /// GAGE12H /// GAGE12I /// GAGE12J /// GAGE2A /// GAGE2B /// GAGE2C /// GAGE2D /// GAGE2E /// GAGE4 /// GAGE5 /// GAGE6 /// GAGE7 /// GAGE8 | G antigen 1 /// G antigen 12B /// G antigen 12C /// G antigen 12D /// G antigen 12E /// G antigen 12F /// G antigen 12G /// G antigen 12H /// G antigen 12I /// G antigen 12J /// G antigen 2A /// G antigen 2B /// G antigen 2C /// G antigen 2D /// G antigen 2E /// G antigen 4 /// G antigen 5 /// G antigen 6 /// G antigen 7 /// G antigen 8 |
| FAM107A /// LOC100506924 | family with sequence similarity 107, member A /// uncharacterized LOC100506924 |

TABLE 14-continued

Core genes MSE 91% Accuracy Disease Classifier Family: Second Binary Decision (NE.UCUP vs. E).

| Gene Symbol | Gene Title |
| --- | --- |
| GAGE3 | G antigen 3 |
| GAGE1 /// GAGE12C /// GAGE12D /// GAGE12E /// GAGE12F /// GAGE12G /// GAGE12H /// GAGE12I /// GAGE12J /// GAGE2A /// GAGE2B /// GAGE2C /// GAGE2D /// GAGE2E /// GAGE3 /// GAGE4 /// GAGE5 /// GAGE6 /// GAGE7 /// GAGE8 | G antigen 1 /// G antigen 12C /// G antigen 12D /// G antigen 12E /// G antigen 12F /// G antigen 12G /// G antigen 12H /// G antigen 12I /// G antigen 12J /// G antigen 2A /// G antigen 2B /// G antigen 2C /// G antigen 2D /// G antigen 2E /// G antigen 3 /// G antigen 4 /// G antigen 5 /// G antigen 6 /// G antigen 7 /// G antigen 8 |
| GAST | gastrin |
| GAGE1 /// GAGE12C /// GAGE12D /// GAGE12E /// GAGE12F /// GAGE12G /// GAGE12H /// GAGE12I /// GAGE12J /// GAGE2D /// GAGE4 /// GAGE5 /// GAGE6 /// GAGE7 | G antigen 1 /// G antigen 12C /// G antigen 12D /// G antigen 12E /// G antigen 12F /// G antigen 12G /// G antigen 12H /// G antigen 12I /// G antigen 12J /// G antigen 2D /// G antigen 4 /// G antigen 5 /// G antigen 6 /// G antigen 7 |
| GAGE12F /// GAGE12G /// GAGE12I /// GAGE4 /// GAGE5 /// GAGE6 /// GAGE7 | G antigen 12F /// G antigen 12G /// G antigen 12I /// G antigen 4 /// G antigen 5 /// G antigen 6 /// G antigen 7 |
| DMBT1 | deleted in malignant brain tumors 1 |
| WNT4 | wingless-type MMTV integration site family, member 4 |
| TOP1 | topoisomerase (DNA) I |
| HBB | hemoglobin, beta |
| NR2F2 | nuclear receptor subfamily 2, group F, member 2 |
| KLHDC10 | kelch domain containing 10 |
| LAMB3 | laminin, beta 3 |
| HLA-DQB1 | major histocompatibility complex, class II, DQ beta 1 |
| PNMA2 | paraneoplastic Ma antigen 2 |
| ADH1B | alcohol dehydrogenase 1B (class I), beta polypeptide |
| HLA-DRB4 /// LOC100509582 | major histocompatibility complex, class II, DR beta 4 /// HLA class II histocompatibility antigen, DR beta 4 chain-like |
| CRISP2 | cysteine-rich secretory protein 2 |
| MT1G | Metallothionein 1G |
| RORA | RAR-related orphan receptor A |
| CYR61 | cysteine-rich, angiogenic inducer, 61 |
| POMZP3 | POM121 and ZP3 fusion |
| LEPR | leptin receptor |
| KIR3DL1 | killer cell immunoglobulin-like receptor, three domains, long cytoplasmic tail, 1 |
| CXCR4 | chemokine (C—X—C motif) receptor 4 |
| PRRC2C | proline-rich coiled-coil 2C |
| IGFBP3 | insulin-like growth factor binding protein 3 |
| SULF1 | sulfatase 1 |
| MFAP4 | microfibrillar-associated protein 4 |
| OLFM4 | olfactomedin 4 |
| IGHM | immunoglobulin heavy constant mu |
| APOE | Apolipoprotein E |
| HLA-DQB1 /// LOC100293977 | major histocompatibility complex, class II, DQ beta 1 /// HLA class II histocompatibility antigen, DQ beta 1 chain-like |
| LTBP4 | latent transforming growth factor beta binding protein 4 |
| MUC5B | mucin 5B, oligomeric mucus/gel-forming |
| CFH | complement factor H |
| HLA-DQA1 /// LOC100507718 /// LOC100509457 | major histocompatibility complex, class II, DQ alpha 1 /// HLA class II histocompatibility antigen, DQ alpha 1 chain-like /// HLA class II histocompatibility antigen, DQ alpha 1 chain-like |
| EEF1E1 | Eukaryotic translation elongation factor 1 epsilon 1 |
| CTCF | CCCTC-binding factor (zinc finger protein) |
| CYP2C9 | cytochrome P450, family 2, subfamily C, polypeptide 9 |
| ADAMTS2 | ADAM metallopeptidase with thrombospondin type 1 motif, 2 |
| CDC42BPA | CDC42 binding protein kinase alpha (DMPK-like) |
| CFH /// CFHR1 | complement factor H /// complement factor H-related 1 |

TABLE 14-continued

Core genes MSE 91% Accuracy Disease Classifier Family: Second Binary Decision (NE.UCUP vs. E).

| Gene Symbol | Gene Title |
| --- | --- |
| DACT1 | dapper, antagonist of beta-catenin, homolog 1 (Xenopus laevis) |
| FAM118A | family with sequence similarity 118, member A |
| HPCAL4 | hippocalcin like 4 |
| DCAF16 | DDB1 and CUL4 associated factor 16 |
| BCMO1 | beta-carotene 15,15'-monooxygenase 1 |
| SPDEF | SAM pointed domain containing ets transcription factor |
| CATSPERB | catsper channel auxiliary subunit beta |
| LRRC31 | leucine rich repeat containing 31 |
| ST6GALNAC5 | ST6 (alpha-N-acetyl-neuraminyl-2,3-beta-galactosyl-1,3)-N-acetylgalactosaminide alpha-2,6-sialyltransferase 5 |
| COLEC12 | collectin sub-family member 12 |
| HLA-DRB1 /// HLA-DRB3 /// HLA-DRB4 /// HLA-DRB5 /// LOC100507709 /// LOC100507714 /// LOC100509582 | major histocompatibility complex, class II, DR beta 1 /// major histocompatibility complex, class II, DR beta 3 /// major histocompatibility complex, class II, DR beta 4 /// major histocompatibility complex, class II, DR beta 5 /// HLA class II histocompatibility antigen, DRB1-7 beta chain-like /// HLA class II histocompatibility antigen, DRB1-7 beta chain-like /// HLA class II histocompatibility antigen, DR beta 4 chain-like |
| LOC100653010 | uncharacterized LOC100653010 |
| GDF15 | growth differentiation factor 15 |
| SIKE1 | suppressor of IKBKE 1 |
| TFG | TRK-fused gene |
| PTER | phosphotriesterase related |
| COL4A3BP | collagen, type IV, alpha 3 (Goodpasture antigen) binding protein |
| CFC1 /// CFC1B | cripto, FRL-1, cryptic family 1 /// cripto, FRL-1, cryptic family 1B |
| SLC46A2 | solute carrier family 46, member 2 |
| MS4A8B | membrane-spanning 4-domains, subfamily A, member 8B |
| H19 /// MIR675 | H19, imprinted maternally expressed transcript (non-protein coding) /// microRNA 675 |
| LIFR | leukemia inhibitory factor receptor alpha |
| COL12A1 | collagen, type XII, alpha 1 |
| BPIFB1 | BPI fold containing family B, member 1 |
| DNER | delta/notch-like EGF repeat containing |
| MEGF6 | multiple EGF-like-domains 6 |
| CCDC146 | coiled-coil domain containing 146 |
| TAOK1 | TAO kinase 1 |
| ERAP2 | endoplasmic reticulum aminopeptidase 2 |
| LOC100505806 | uncharacterized LOC100505806 |
| NAPSB | napsin B aspartic peptidase pseudogene |
| ZG16B | zymogen granule protein 16 homolog B (rat) |
| IGSF11 | immunoglobulin superfamily, member 11 |
| NFYA | nuclear transcription factor Y, alpha |
| LOC100506029 /// LOC100506051 | uncharacterized LOC100506029 /// uncharacterized LOC100506051 |
| THRB | thyroid hormone receptor, beta |
| CYS1 | cystin 1 |
| MCTP2 | multiple C2 domains, transmembrane 2 |
| NPAS3 | neuronal PAS domain protein 3 |
| C20orf85 | chromosome 20 open reading frame 85 |
| FAM69C | family with sequence similarity 69, member C |
| SCARA5 | scavenger receptor class A, member 5 (putative) |
| FNDC3B | fibronectin type III domain containing 3B |
| PI15 | peptidase inhibitor 15 |
| SCGB3A1 | secretoglobin, family 3A, member 1 |
| KLF9 | Kruppel-like factor 9 |
| GBP1 | guanylate binding protein 1, interferon-inducible |
| MAVS | mitochondrial antiviral signaling protein |
| ANKRD33B | ankyrin repeat domain 33B |
| SNORD3B-1 /// SNORD3B-2 /// SNORD3D | small nucleolar RNA, C/D box 3B-1 /// small nucleolar RNA, C/D box 3B-2 /// small nucleolar RNA, C/D box 3D |

TABLE 14-continued

Core genes MSE 91% Accuracy Disease Classifier Family: Second Binary Decision (NE.UCUP vs. E).

| Gene Symbol | Gene Title |
| --- | --- |
| FAM178A | family with sequence similarity 178, member A |
| THAP6 | THAP domain containing 6 |
| LOC100422737 | uncharacterized LOC100422737 |
| SCARA5 | scavenger receptor class A, member 5 (putative) |
| SUZ12P | Suppressor of zeste 12 homolog pseudogene |
| BCL2L10 | BCL2-like 10 (apoptosis facilitator) |
| RIMKLB | ribosomal modification protein rimK-like family member B |
| PLEKHA2 | pleckstrin homology domain containing, family A (phosphoinositide binding specific) member 2 |
| EIF4E3 | eukaryotic translation initiation factor 4E family member 3 |
| SGPP2 | sphingosine-1-phosphate phosphatase 2 |
| RAB3IP | RAB3A interacting protein (rabin3) |
| DOK7 | docking protein 7 |
| MIB2 | mindbomb E3 ubiquitin protein ligase 2 |
| LOC100653229 | uncharacterized LOC100653229 |
| ITGB8 | integrin, beta 8 |
| WDR38 | WD repeat domain 38 |
| SHISA8 | shisa homolog 8 (*Xenopus laevis*) |

TABLE 15

Core genes MSE 100% Severity Classifier Family: E-Min/Mild vs. E-Mod/Severe.

| Gene Symbol | Gene Title |
| --- | --- |
| HSPA6 | heat shock 70 kDa protein 6 (HSP70B'); Genbank: NM_002155, X51757. |
| THRA | thyroid hormone receptor, alpha |
| GIMAP1 | GTPase, IMAP family member 1 |
| TIRAP | toll-interleukin 1 receptor (TIR) domain containing adaptor protein |
| ACVR1C | activin A receptor, type IC |
| IL12RB1 | interleukin 12 receptor, beta 1 |
| JAK1 | Janus kinase 1 |
| RAD51L3-RFFL /// RFFL | RAD51L3-RFFL readthrough /// ring finger and FYVE-like domain containing E3 ubiquitin protein ligase |
| ZNF417 | zinc finger protein 417 |
| SEC62 | SEC62 homolog (*S. cerevisiae*) |
| SIGLEC10 | sialic acid binding Ig-like lectin 10 |
| KCNG3 | potassium voltage-gated channel, subfamily G, member 3 |
| CD300LF | CD300 molecule-like family member f |
| MOGAT1 | monoacylglycerol O-acyltransferase 1 |
| SLC5A3 | solute carrier family 5 (sodium/myo-inositol cotransporter), member 3 |
| FOXC1 | forkhead box C1 |
| PRF1 | perforin 1 (pore forming protein) |
| WBSCR27 | Williams Beuren syndrome chromosome region 27 |
| ARSB | arylsulfatase B |
| CCDC60 | coiled-coil domain containing 60 |
| COCH | coagulation factor C homolog, cochlin (*Limulus polyphemus*) |
| SLC25A48 | solute carrier family 25, member 48 |
| CELF2 | CUGBP, Elav-like family member 2 |
| DUOXA1 | dual oxidase maturation factor 1 |
| METTL8 | methyltransferase like 8 |
| TACC1 | transforming, acidic coiled-coil containing protein 1 |
| TBC1D16 | TBC1 domain family, member 16 |
| ZBED1 | zinc finger, BED-type containing 1 |
| DOK5 | docking protein 5 |
| FCER1G | Fc fragment of IgE, high affinity I, receptor for; gamma polypeptide |
| ATF3 | activating transcription factor 3 |
| FCHO2 | FCH domain only 2 |
| CCNL1 | cyclin L1 |
| CYP4B1 | cytochrome P450, family 4, subfamily B, polypeptide 1 |

TABLE 15-continued

Core genes MSE 100% Severity Classifier Family: E-Min/Mild vs. E-Mod/Severe.

| Gene Symbol | Gene Title |
| --- | --- |
| CLEC7A | C-type lectin domain family 7, member A |
| TRIB3 | tribbles homolog 3 (*Drosophila*) |
| LOC284454 | uncharacterized LOC284454 |
| CACNA1D | calcium channel, voltage-dependent, L type, alpha 1D subunit |
| DIAPH3-AS1 | DIAPH3 antisense RNA 1 (non-protein coding) |
| LOC100506523 /// ZNF814 | uncharacterized LOC100506523 /// zinc finger protein 814 |
| RPPH1 | ribonuclease P RNA component H1 |
| SERPINB6 | serpin peptidase inhibitor, clade B (ovalbumin), member 6 |
| LEPR | leptin receptor |
| LOC100507250 | uncharacterized LOC100507250 |
| LOC100506258 | uncharacterized LOC100506258 |
| ACSL4 | Acyl-CoA synthetase long-chain family member 4 |
| BIN3 | bridging integrator 3 |
| PTRF | polymerase I and transcript release factor |
| ZKSCAN1 | zinc finger with KRAB and SCAN domains 1 |
| ZNF587 /// ZNF587B | zinc finger protein 587 /// zinc finger protein 587B |
| MIR1204 /// PVT1 | microRNA 1204 /// Pvt1 oncogene (non-protein coding) |
| ZDHHC18 | zinc finger, DHHC-type containing 18 |
| SIRT2 | sirtuin 2 |
| AHNAK2 | AHNAK nucleoprotein 2 |
| C1orf53 | chromosome 1 open reading frame 53 |
| LOC100507645 /// MALAT1 | uncharacterized LOC100507645 /// metastasis associated lung adenocarcinoma transcript 1 (non-protein coding) |
| ZNF321P /// ZNF816 /// ZNF816-ZNF321P | zinc finger protein 321, pseudogene /// zinc finger protein 816 /// ZNF816-ZNF321P readthrough |
| CACNB2 | calcium channel, voltage-dependent, beta 2 subunit |
| LOC642852 | uncharacterized LOC642852 |
| FLJ38717 | FLJ38717 protein |
| SFXN3 | Sideroflexin 3 |
| LOC100506387 | uncharacterized LOC100506387 |
| LOC201477 | uncharacterized LOC201477 |
| SLC8A1 | solute carrier family 8 (sodium/calcium exchanger), member 1 |
| KIAA1908 | uncharacterized LOC114796 |
| SF3B14 | Splicing factor 3B, 14 kDa subunit |
| OR7D2 | olfactory receptor, family 7, subfamily D, member 2 |
| TNRC18 | trinucleotide repeat containing 18 |
| LOC100630923 | LOC100289561-PRKRIP1 readthrough |
| ATF1 | activating transcription factor 1 |
| IKZF1 | IKAROS family zinc finger 1 (Ikaros) |
| PNN | pinin, desmosome associated protein |
| CD74 | CD74 molecule, major histocompatibility complex, class II invariant chain |
| PAAF1 | proteasomal ATPase-associated factor 1 |
| BRE-AS1 | BRE antisense RNA 1 (non-protein coding) |
| LINC00240 | long intergenic non-protein coding RNA 240 |
| ANKRD20A1 /// ANKRD20A11P /// ANKRD20A2 /// ANKRD20A3 /// ANKRD20A4 /// ANKRD20A5P /// ANKRD20A9P /// LOC644339 | ankyrin repeat domain 20 family, member A1 /// ankyrin repeat domain 20 family, member A11, pseudogene /// ankyrin repeat domain 20 family, member A2 /// ankyrin repeat domain 20 family, member A3 /// ankyrin repeat domain 20 family, member A4 /// ankyrin repeat domain 20 family, member A5, pseudogene /// ankyrin repeat domain 20 family, member A9, pseudogene /// ankyrin repeat domain-containing protein 20B-like |
| CATSPERB | catsper channel auxiliary subunit beta |
| SCD | stearoyl-CoA desaturase (delta-9-desaturase) |
| DHCR24 | 24-dehydrocholesterol reductase |
| DUSP1 | dual specificity phosphatase 1 |
| CYR61 | cysteine-rich, angiogenic inducer, 61 |
| NREP | neuronal regeneration related protein homolog (rat) |
| GPX3 | glutathione peroxidase 3 (plasma) |
| MYH11 | myosin, heavy chain 11, smooth muscle |
| ZFP36 | zinc finger protein 36, C3H type, homolog (mouse) |
| INSIG1 | insulin induced gene 1 |
| TNC | tenascin C |
| ACSL3 | acyl-CoA synthetase long-chain family member 3 |
| NIPSNAP1 | nipsnap homolog 1 (*C. elegans*) |
| ENG | endoglin |
| CPD | carboxypeptidase D |
| PPP1R12B | protein phosphatase 1, regulatory subunit 12B |

TABLE 15-continued

Core genes MSE 100% Severity Classifier Family: E-Min/Mild vs. E-Mod/Severe.

| Gene Symbol | Gene Title |
|---|---|
| LTF | lactotransferrin |
| DKK3 | dickkopf 3 homolog (*Xenopus laevis*) |
| AMFR | autocrine motility factor receptor, E3 ubiquitin protein ligase |
| NR4A1 | nuclear receptor subfamily 4, group A, member 1 |
| COL1A2 | collagen, type I, alpha 2 |
| IGF2 /// INS-IGF2 | insulin-like growth factor 2 (somatomedin A) /// INS-IGF2 readthrough |
| KIAA0101 | KIAA0101 |
| DHFR | dihydrofolate reductase |
| NRIP1 | nuclear receptor interacting protein 1 |
| ICAM1 | intercellular adhesion molecule 1 |
| SERTAD2 | SERTA domain containing 2 |
| GPX2 | glutathione peroxidase 2 (gastrointestinal) |
| ANPEP | alanyl (membrane) aminopeptidase |
| ADM | adrenomedullin |
| SOX9 | SRY (sex determining region Y)-box 9 |
| CAPN6 | calpain 6 |
| STMN2 | stathmin-like 2 |
| FH | fumarate hydratase |
| C2 | complement component 2 |
| FBN2 | fibrillin 2 |
| ST3GAL5 | ST3 beta-galactoside alpha-2,3-sialyltransferase 5 |
| TLE1 | transducin-like enhancer of split 1 (E(sp1) homolog, *Drosophila*) |
| ATXN1 | ataxin 1 |
| FCGBP | Fc fragment of IgG binding protein |
| CDH3 | cadherin 3, type 1, P-cadherin (placental) |
| HLA-DQA1 | major histocompatibility complex, class II, DQ alpha 1 |
| PSD3 | pleckstrin and Sec7 domain containing 3 |
| EPN2 | epsin 2 |
| S100A9 | S100 calcium binding protein A9 |
| KLF9 | Kruppel-like factor 9 |
| LOXL1 | lysyl oxidase-like 1 |
| CSF3R | colony stimulating factor 3 receptor (granulocyte) |
| GPRC5B | G protein-coupled receptor, family C, group 5, member B |
| PLA2G2A | phospholipase A2, group IIA (platelets, synovial fluid) |
| BCL2 | B-cell CLL/lymphoma 2 |
| PI3 | peptidase inhibitor 3, skin-derived |
| PDE4B | phosphodiesterase 4B, cAMP-specific |
| MPZL2 | myelin protein zero-like 2 |
| SEMA3C | sema domain, immunoglobulin domain (Ig), short basic domain, secreted, (semaphorin) 3C |
| PCGF2 | polycomb group ring finger 2 |
| GSTT1 | glutathione S-transferase theta 1 |
| TSPAN8 | tetraspanin 8 |
| SCG5 | secretogranin V (7B2 protein) |
| MMP9 | matrix metallopeptidase 9 (gelatinase B, 92 kDa gelatinase, 92 kDa type IV collagenase) |
| HBA1 /// HBA2 | hemoglobin, alpha 1 /// hemoglobin, alpha 2 |
| RFC4 | replication factor C (activator 1) 4, 37 kDa |
| CTAGE5 | CTAGE family, member 5 |
| AGAP1 | ArfGAP with GTPase domain, ankyrin repeat and PH domain 1 |
| PRAME | preferentially expressed antigen in melanoma |
| IL2RG | interleukin 2 receptor, gamma |
| GADD45G | growth arrest and DNA-damage-inducible, gamma |
| GSTM4 | glutathione S-transferase mu 4 |
| ENPP4 | ectonucleotide pyrophosphatase/phosphodiesterase 4 (putative) |
| CD37 | CD37 molecule |
| S100A2 | S100 calcium binding protein A2 |
| SKI | v-ski sarcoma viral oncogene homolog (avian) |
| FARS2 | phenylalanyl-tRNA synthetase 2, mitochondrial |
| PROM1 | prominin 1 |
| AK4 /// LOC100507855 | adenylate kinase 4 /// adenylate kinase isoenzyme 4, mitochondrial-like |
| SLC43A1 | solute carrier family 43, member 1 |
| GSTM2 | glutathione S-transferase mu 2 (muscle) |
| FOLR1 | folate receptor 1 (adult) |
| IFI44L | interferon-induced protein 44-like |
| MMP1 | matrix metallopeptidase 1 (interstitial collagenase) |
| CDC7 | cell division cycle 7 homolog (*S. cerevisiae*) |

TABLE 15-continued

Core genes MSE 100% Severity Classifier Family: E-Min/Mild vs. E-Mod/Severe.

| Gene Symbol | Gene Title |
|---|---|
| TOX | thymocyte selection-associated high mobility group box |
| CXCL10 | chemokine (C—X—C motif) ligand 10 |
| GABRE /// MIR224 /// MIR452 | gamma-aminobutyric acid (GABA) A receptor, epsilon /// microRNA 224 /// microRNA 452 |
| GSTM1 | glutathione S-transferase mu 1 |
| APOC2 /// APOC4 /// APOC4-APOC2 | apolipoprotein C-II /// apolipoprotein C-IV /// APOC4-APOC2 readthrough |
| ABCG1 | ATP-binding cassette, sub-family G (WHITE), member 1 |
| MMP12 | matrix metallopeptidase 12 (macrophage elastase) |
| DKK1 | dickkopf 1 homolog (*Xenopus laevis*) |
| SERPINB2 | serpin peptidase inhibitor, clade B (ovalbumin), member 2 |
| TFF3 | trefoil factor 3 (intestinal) |
| SRD5A1 | steroid-5-alpha-reductase, alpha polypeptide 1 (3-oxo-5 alpha-steroid delta 4-dehydrogenase alpha 1) |
| ABCA8 | ATP-binding cassette, sub-family A (ABC1), member 8 |
| RIMS3 | regulating synaptic membrane exocytosis 3 |
| DUSP2 | dual specificity phosphatase 2 |
| CKM | creatine kinase, muscle |
| FOLR2 | folate receptor 2 (fetal) |
| MLH3 | mutL homolog 3 (*E. coli*) |
| ENPEP | glutamyl aminopeptidase (aminopeptidase A) |
| MSLN | mesothelin |
| LYPD3 | LY6/PLAUR domain containing 3 |
| ASNS | asparagine synthetase (glutamine-hydrolyzing) |
| PSPH | phosphoserine phosphatase |
| AOX1 | aldehyde oxidase 1 |
| SLC26A2 | solute carrier family 26 (sulfate transporter), member 2 |
| CCR1 | chemokine (C-C motif) receptor 1 |
| NEFM | neurofilament, medium polypeptide |
| CCL3 /// CCL3L1 /// CCL3L3 | chemokine (C-C motif) ligand 3 /// chemokine (C-C motif) ligand 3-like 1 /// chemokine (C-C motif) ligand 3-like 3 |
| PTGS1 | prostaglandin-endoperoxide synthase 1 (prostaglandin G/H synthase and cyclooxygenase) |
| ACTC1 | actin, alpha, cardiac muscle 1 |
| ITGB3BP | integrin beta 3 binding protein (beta3-endonexin) |
| AP1S1 | adaptor-related protein complex 1, sigma 1 subunit |
| HCAR3 | hydroxycarboxylic acid receptor 3 |
| SOD3 | superoxide dismutase 3, extracellular |
| LIF | leukemia inhibitory factor |
| IGFBP1 | insulin-like growth factor binding protein 1 |
| TMSB15A /// TMSB15B | thymosin beta 15a /// thymosin beta 15B |
| GGCX | gamma-glutamyl carboxylase |
| CBR3 | carbonyl reductase 3 |
| PRSS2 | protease, serine, 2 (trypsin 2) |
| SLC22A3 | solute carrier family 22 (extraneuronal monoamine transporter), member 3 |
| GSTT2 | glutathione S-transferase theta 2 |
| PRL | prolactin |
| MST1R | macrophage stimulating 1 receptor (c-met-related tyrosine kinase) |
| CD3E | CD3e molecule, epsilon (CD3-TCR complex) |
| KLK11 | kallikrein-related peptidase 11 |
| GZMA | granzyme A (granzyme 1, cytotoxic T-lymphocyte-associated serine esterase 3) |
| GNLY | granulysin |
| AVIL | advillin |
| BPI | bactericidal/permeability-increasing protein |
| HRH1 | histamine receptor H1 |
| NOS3 | nitric oxide synthase 3 (endothelial cell) |
| OLFM1 | olfactomedin 1 |
| C4BPA | complement component 4 binding protein, alpha |
| OASL | 2'-5'-oligoadenylate synthetase-like |
| TPSAB1 | tryptase alpha/beta 1 |
| SYNGR3 | synaptogyrin 3 |
| CBLN1 | cerebellin 1 precursor |
| CD8A | CD8a molecule |
| CYP3A5 | cytochrome P450, family 3, subfamily A, polypeptide 5 |
| WISP2 | WNT1 inducible signaling pathway protein 2 |
| CD2 | CD2 molecule |
| PART1 | prostate androgen-regulated transcript 1 (non-protein coding) |

TABLE 15-continued

Core genes MSE 100% Severity Classifier Family: E-Min/Mild vs. E-Mod/Severe.

| Gene Symbol | Gene Title |
| --- | --- |
| SLC7A4 | solute carrier family 7 (orphan transporter), member 4 |
| GABBR1 /// UBD | gamma-aminobutyric acid (GABA) B receptor, 1 /// ubiquitin D |
| SLC22A4 | solute carrier family 22 (organic cation/ergothioneine transporter), member 4 |
| PLCL1 | phospholipase C-like 1 |
| EPHA1 | EPH receptor A1 |
| HABP2 | hyaluronan binding protein 2 |
| LEFTY2 | left-right determination factor 2 |
| TNFAIP6 | tumor necrosis factor, alpha-induced protein 6 |
| ACADL | acyl-CoA dehydrogenase, long chain |
| PTPRR | protein tyrosine phosphatase, receptor type, R |
| LRRC37A3 | leucine rich repeat containing 37, member A3 |
| MATN3 | matrilin 3 |
| UGT1A1 /// UGT1A10 /// UGT1A3 /// UGT1A4 /// UGT1A5 /// UGT1A6 /// UGT1A7 /// UGT1A8 /// UGT1A9 | UDP glucuronosyltransferase 1 family, polypeptide A1 /// UDP glucuronosyltransferase 1 family, polypeptide A10 /// UDP glucuronosyltransferase 1 family, polypeptide A3 /// UDP glucuronosyltransferase 1 family, polypeptide A4 /// UDP glucuronosyltransferase 1 family, polypeptide A5 /// UDP glucuronosyltransferase 1 family, polypeptide A6 /// UDP glucuronosyltransferase 1 family, polypeptide A7 /// UDP glucuronosyltransferase 1 family, polypeptide A8 /// UDP glucuronosyltransferase 1 family, polypeptide A9 |
| KLK8 | kallikrein-related peptidase 8 |
| CYP4F11 | cytochrome P450, family 4, subfamily F, polypeptide 11 |
| ARHGAP6 | Rho GTPase activating protein 6 |
| IL13RA2 | interleukin 13 receptor, alpha 2 |
| CST1 | cystatin SN |
| MMP17 | matrix metallopeptidase 17 (membrane-inserted) |
| ARHGAP22 | Rho GTPase activating protein 22 |
| FAM155B | family with sequence similarity 155, member B |
| PTHLH | parathyroid hormone-like hormone |
| SPINK2 | serine peptidase inhibitor, Kazal type 2 (acrosin-trypsin inhibitor) |
| GRP | gastrin-releasing peptide |
| CXCL6 | chemokine (C—X—C motif) ligand 6 (granulocyte chemotactic protein 2) |
| COX6A2 | cytochrome c oxidase subunit VIa polypeptide 2 |
| XCL1 | chemokine (C motif) ligand 1 |
| SCGB2A2 | secretoglobin, family 2A, member 2 |
| PF4 | platelet factor 4 |
| B4GALNT1 | beta-1,4-N-acetyl-galactosaminyl transferase 1 |
| S1PR4 | sphingosine-1-phosphate receptor 4 |
| LTC4S | leukotriene C4 synthase |
| ABAT | 4-aminobutyrate aminotransferase |
| AKR1B10 | aldo-keto reductase family 1, member B10 (aldose reductase) |
| LY96 | lymphocyte antigen 96 |
| SLC16A5 | solute carrier family 16, member 5 (monocarboxylic acid transporter 6) |
| ZMYM5 | zinc finger, MYM-type 5 |
| GP2 | glycoprotein 2 (zymogen granule membrane) |
| FAM65B | family with sequence similarity 65, member B |
| CRYBB2 /// CRYBB2P1 | crystallin, beta B2 /// crystallin, beta B2 pseudogene 1 |
| WISP1 | WNT1 inducible signaling pathway protein 1 |
| PAEP | progestagen-associated endometrial protein |
| IL11 | interleukin 11 |
| BGLAP /// PMF1-BGLAP | bone gamma-carboxyglutamate (gla) protein /// PMF1-BGLAP readthrough |
| TNF | tumor necrosis factor |
| TPSB2 | tryptase beta 2 (gene/pseudogene) |
| DIO3 | deiodinase, iodothyronine, type III |
| ALOX12 | arachidonate 12-lipoxygenase |
| CD300C | CD300c molecule |
| CD209 | CD209 molecule |
| KIR3DL1 /// KIR3DL2 /// LOC727787 | killer cell immunoglobulin-like receptor, three domains, long cytoplasmic tail, 1 /// killer cell immunoglobulin-like receptor, three domains, long cytoplasmic tail, 2 /// killer cell immunoglobulin-like receptor, three domains, long cytoplasmic tail, 2-like |

TABLE 15-continued

Core genes MSE 100% Severity Classifier Family: E-Min/Mild vs. E-Mod/Severe.

| Gene Symbol | Gene Title |
| --- | --- |
| KIR3DL2 /// LOC727787 | killer cell immunoglobulin-like receptor, three domains, long cytoplasmic tail, 2 /// killer cell immunoglobulin-like receptor, three domains, long cytoplasmic tail, 2-like |
| DEFB4A /// DEFB4B | defensin, beta 4A /// defensin, beta 4B |
| RAC2 | ras-related C3 botulinum toxin substrate 2 (rho family, small GTP binding protein Rac2) |
| GZMM | granzyme M (lymphocyte met-ase 1) |
| PIR | pirin (iron-binding nuclear protein) |
| BDKRB1 | bradykinin receptor B1 |
| GADD45B | growth arrest and DNA-damage-inducible, beta |
| PSG9 | pregnancy specific beta-1-glycoprotein 9 |
| GAGE1 /// GAGE12C /// GAGE12D /// GAGE12E /// GAGE12F /// GAGE12G /// GAGE12H /// GAGE12I /// GAGE12J /// GAGE2A /// GAGE2B /// GAGE2C /// GAGE2D /// GAGE2E /// GAGE3 /// GAGE4 /// GAGE5 /// GAGE6 /// GAGE7 /// GAGE8 | G antigen 1 /// G antigen 12C /// G antigen 12D /// G antigen 12E /// G antigen 12F /// G antigen 12G /// G antigen 12H /// G antigen 12I /// G antigen 12J /// G antigen 2A /// G antigen 2B /// G antigen 2C /// G antigen 2D /// G antigen 2E /// G antigen 3 /// G antigen 4 /// G antigen 5 /// G antigen 6 /// G antigen 7 /// G antigen 8 |
| FGFR1 | fibroblast growth factor receptor 1 |
| MUC1 | mucin 1, cell surface associated |
| KRT13 | keratin 13 |
| NFAT5 | nuclear factor of activated T-cells 5, tonicity-responsive |
| LINC00597 | long intergenic non-protein coding RNA 597 |
| KIR2DS3 | killer cell immunoglobulin-like receptor, two domains, short cytoplasmic tail, 3 |
| PTGIS | prostaglandin I2 (prostacyclin) synthase |
| GAST | gastrin |
| KIR2DS1 | killer cell immunoglobulin-like receptor, two domains, short cytoplasmic tail, 1 |
| KIR2DS5 | killer cell immunoglobulin-like receptor, two domains, short cytoplasmic tail, 5 |
| DMBT1 | deleted in malignant brain tumors 1 |
| TH | tyrosine hydroxylase |
| ANK1 | ankyrin 1, erythrocytic |
| KIR2DL2 /// KIR2DL4 /// KIR2DL5A /// KIR2DL5B /// KIR3DL3 /// KIR3DS1 /// LOC100287534 | killer cell immunoglobulin-like receptor, two domains, long cytoplasmic tail, 2 /// killer cell immunoglobulin-like receptor, two domains, long cytoplasmic tail, 4 /// killer cell immunoglobulin-like receptor, two domains, long cytoplasmic tail, 5A /// killer cell immunoglobulin-like receptor, two domains, long cytoplasmic tail, 5B /// killer cell immunoglobulin-like receptor three domains long cytoplasmic tail 3 /// killer cell immunoglobulin-like receptor, three domains, short cytoplasmic tail, 1 /// killer cell immunoglobulin-like receptor 2DL4-like |
| RASA4 /// RASA4B /// RASA4CP /// UPK3BL | RAS p21 protein activator 4 /// RAS p21 protein activator 4B /// RAS p21 protein activator 4C, pseudogene /// uroplakin 3B-like |
| WNT4 | wingless-type MMTV integration site family, member 4 |
| AP3D1 | adaptor-related protein complex 3, delta 1 subunit |
| LGALS8 | lectin, galactoside-binding, soluble, 8 |
| UPF1 | UPF1 regulator of nonsense transcripts homolog (yeast) |
| KRT7 | keratin 7 |
| CORO1A | coronin, actin binding protein, 1A |
| UBN1 | ubinuclein 1 |
| HBB | hemoglobin, beta |
| AKR1C3 | aldo-keto reductase family 1, member C3 (3-alpha hydroxysteroid dehydrogenase, type II) |
| FOS | FBJ murine osteosarcoma viral oncogene homolog |
| TFPI2 | tissue factor pathway inhibitor 2 |
| CA2 | carbonic anhydrase II |
| AZGP1 | alpha-2-glycoprotein 1, zinc-binding |
| RGS16 | regulator of G-protein signaling 16 |
| MALL | mal, T-cell differentiation protein-like |
| SCAF11 | SR-related CTD-associated factor 11 |
| DLK1 | delta-like 1 homolog (*Drosophila*) |
| CES1 /// LOC100653057 | carboxylesterase 1 /// liver carboxylesterase 1-like |
| HLA-DRB4 /// LOC100509582 | major histocompatibility complex, class II, DR beta 4 /// HLA class II histocompatibility antigen, DR beta 4 chain-like |

TABLE 15-continued

Core genes MSE 100% Severity Classifier Family: E-Min/Mild vs. E-Mod/Severe.

| Gene Symbol | Gene Title |
| --- | --- |
| NR1D2 | nuclear receptor subfamily 1, group D, member 2 |
| RRM2 | ribonucleotide reductase M2 |
| CXCL2 | chemokine (C—X—C motif) ligand 2 |
| CASP6 | caspase 6, apoptosis-related cysteine peptidase |
| KLK10 | kallikrein-related peptidase 10 |
| TARP | TCR gamma alternate reading frame protein |
| SPP1 | secreted phosphoprotein 1 |
| TNNC1 | troponin C type 1 (slow) |
| TGFB2 | transforming growth factor, beta 2 |
| SLC7A11 | solute carrier family 7 (anionic amino acid transporter light chain, xc-system), member 11 |
| CD247 | CD247 molecule |
| RND1 | Rho family GTPase 1 |
| MAPK13 | mitogen-activated protein kinase 13 |
| UPK1B | uroplakin 1B |
| ARC | activity-regulated cytoskeleton-associated protein |
| CYP4B1 | cytochrome P450, family 4, subfamily B, polypeptide 1 |
| PLA2G4A | phospholipase A2, group IVA (cytosolic, calcium-dependent) |
| GZMB | granzyme B (granzyme 2, cytotoxic T-lymphocyte-associated serine esterase 1) |
| IRX5 | iroquois homeobox 5 |
| DLG5 | discs, large homolog 5 (*Drosophila*) |
| CTAG1A /// CTAG1B | cancer/testis antigen 1A /// cancer/testis antigen 1B |
| CCL23 | chemokine (C-C motif) ligand 23 |
| LAIR1 | leukocyte-associated immunoglobulin-like receptor 1 |
| NRTN | neurturin |
| CLDN14 | claudin 14 |
| SLC43A3 | solute carrier family 43, member 3 |
| NCR3 | natural cytotoxicity triggering receptor 3 |
| POSTN | periostin, osteoblast specific factor |
| KIR2DL1 /// KIR2DL2 /// KIR2DL3 /// KIR2DL4 /// KIR2DL5A /// KIR2DL5B /// KIR3DL3 /// KIR3DS1 /// LOC100287534 //// LOC100653050 | killer cell immunoglobulin-like receptor, two domains, long cytoplasmic tail, 1 /// killer cell immunoglobulin-like receptor, two domains, long cytoplasmic tail, 2 /// killer cell immunoglobulin-like receptor, two domains, long cytoplasmic tail, 3 /// killer cell immunoglobulin-like receptor, two domains, long cytoplasmic tail, 4 /// killer cell immunoglobulin-like receptor, two domains, long cytoplasmic tail, 5A /// killer cell immunoglobulin-like receptor, two domains, long cytoplasmic tail, 5B /// killer cell immunoglobulin-like receptor three domains long cytoplasmic tail 3 /// killer cell immunoglobulin-like receptor, three domains, short cytoplasmic tail, 1 /// killer cell immunoglobulin-like receptor 2DL4-like /// killer cell immunoglobulin-like receptor 2DL2-like |
| AP3D1 | adaptor-related protein complex 3, delta 1 subunit |
| HLA-DRA | major histocompatibility complex, class II, DR alpha |
| HGF | hepatocyte growth factor (hepapoietin A; scatter factor) |
| PSTPIP1 | proline-serine-threonine phosphatase interacting protein 1 |
| KIR2DL4 | killer cell immunoglobulin-like receptor, two domains, long cytoplasmic tail, 4 |
| KIR2DL2 | killer cell immunoglobulin-like receptor, two domains, long cytoplasmic tail, 2 |
| MAPK11 | mitogen-activated protein kinase 11 |
| KIR2DS1 /// KIR2DS2 /// KIR2DS3 /// KIR2DS4 /// KIR2DS5 /// KIR3DL3 | killer cell immunoglobulin-like receptor, two domains, short cytoplasmic tail, 1 /// killer cell immunoglobulin-like receptor, two domains, short cytoplasmic tail, 2 /// killer cell immunoglobulin-like receptor, two domains, short cytoplasmic tail, 3 /// killer cell immunoglobulin-like receptor, two domains, short cytoplasmic tail, 4 /// killer cell immunoglobulin-like receptor, two domains, short cytoplasmic tail, 5 /// killer cell immunoglobulin-like receptor three domains long cytoplasmic tail 3 |
| CEACAM6 | carcinoembryonic antigen-related cell adhesion molecule 6 (non-specific cross reacting antigen) |
| KIR3DL1 | killer cell immunoglobulin-like receptor, three domains, long cytoplasmic tail, 1 |
| PRG2 | proteoglycan 2, bone marrow (natural killer cell activator, eosinophil granule major basic protein) |
| COL4A2 | collagen, type IV, alpha 2 |
| HLA-DPA1 | major histocompatibility complex, class II, DP alpha 1 |

TABLE 15-continued

Core genes MSE 100% Severity Classifier Family: E-Min/Mild vs. E-Mod/Severe.

| Gene Symbol | Gene Title |
| --- | --- |
| WNK1 | WNK lysine deficient protein kinase 1 |
| DAG1 | dystroglycan 1 (dystrophin-associated glycoprotein 1) |
| FNBP4 | formin binding protein 4 |
| PIK3R1 | phosphoinositide-3-kinase, regulatory subunit 1 (alpha) |
| SLC7A1 | solute carrier family 7 (cationic amino acid transporter, y+ system), member 1 |
| CLASP2 | cytoplasmic linker associated protein 2 |
| MYO1D | myosin ID |
| KHNYN | KH and NYN domain containing |
| SEP6 | septin 6 |
| CERS6 | ceramide synthase 6 |
| COL5A1 | collagen, type V, alpha 1 |
| IL1RN | interleukin 1 receptor antagonist |
| RASA4 /// RASA4B /// RASA4CP | RAS p21 protein activator 4 /// RAS p21 protein activator 4B /// RAS p21 protein activator 4C, pseudogene |
| NFATC2IP | nuclear factor of activated T-cells, cytoplasmic, calcineurin-dependent 2 interacting protein |
| PLEKHG3 | pleckstrin homology domain containing, family G (with RhoGef domain) member 3 |
| SUPV3L1 | suppressor of var1, 3-like 1 (*S. cerevisiae*) |
| COL6A1 | collagen, type VI, alpha 1 |
| BBX | bobby sox homolog (*Drosophila*) |
| GATAD1 | GATA zinc finger domain containing 1 |
| CHI3L2 | chitinase 3-like 2 |
| NEK3 | NIMA (never in mitosis gene a)-related kinase 3 |
| TIAM1 | T-cell lymphoma invasion and metastasis 1 |
| PLCB1 | phospholipase C, beta 1 (phosphoinositide-specific) |
| KRT4 | keratin 4 |
| ZNF248 | zinc finger protein 248 |
| TCF25 | transcription factor 25 (basic helix-loop-helix) |
| PAQR3 | progestin and adipoQ receptor family member III |
| MUC5B | mucin 5B, oligomeric mucus/gel-forming |
| RUFY3 | RUN and FYVE domain containing 3 |
| NPTX2 | neuronal pentraxin II |
| TRA2A | transformer 2 alpha homolog (*Drosophila*) |
| ENOSF1 | enolase superfamily member 1 |
| SLC1A1 | solute carrier family 1 (neuronal/epithelial high affinity glutamate transporter, system Xag), member 1 |
| FAM69A | family with sequence similarity 69, member A |
| GLB1L2 | galactosidase, beta 1-like 2 |
| KSR1 | kinase suppressor of ras 1 |
| STARD5 | StAR-related lipid transfer (START) domain containing 5 |
| CLMN | calmin (calponin-like, transmembrane) |
| THSD7A | thrombospondin, type I, domain containing 7A |
| PAX8 | paired box 8 |
| RPGRIP1L | RPGRIP1-like |
| ZAP70 | zeta-chain (TCR) associated protein kinase 70 kDa |
| CCL8 | chemokine (C-C motif) ligand 8 |
| GSN | gelsolin |
| PTPRD | protein tyrosine phosphatase, receptor type, D |
| MBD4 | methyl-CpG binding domain protein 4 |
| CD7 | CD7 molecule |
| MYRIP | myosin VIIA and Rab interacting protein |
| GNAS | GNAS complex locus |
| ABCB9 | ATP-binding cassette, sub-family B (MDR/TAP), member 9 |
| GAL | galanin prepropeptide |
| DKK3 | dickkopf 3 homolog (*Xenopus laevis*) |
| RPL17 /// RPL17-C18ORF32 | ribosomal protein L17 /// RPL17-C18orf32 readthrough |
| MUC5AC | mucin 5AC, oligomeric mucus/gel-forming |
| NOV | nephroblastoma overexpressed |
| JUND | jun D proto-oncogene |
| RASGRP2 | RAS guanyl releasing protein 2 (calcium and DAG-regulated) |
| HSPA12A | heat shock 70 kDa protein 12A |
| CTSW | cathepsin W |
| CDC42BPA | CDC42 binding protein kinase alpha (DMPK-like) |
| KLRB1 | killer cell lectin-like receptor subfamily B, member 1 |
| ADAMTS2 | ADAM metallopeptidase with thrombospondin type 1 motif, 2 |

TABLE 15-continued

Core genes MSE 100% Severity Classifier Family: E-Min/Mild vs. E-Mod/Severe.

| Gene Symbol | Gene Title |
| --- | --- |
| CD7 | CD7 molecule |
| LILRP2 | leukocyte immunoglobulin-like receptor pseudogene 2 |
| XCL1 /// XCL2 | chemokine (C motif) ligand 1 /// chemokine (C motif) ligand 2 |
| MNX1 | motor neuron and pancreas homeobox 1 |
| SEP10 | septin 10 |
| ADD1 | adducin 1 (alpha) |
| HSPB6 | heat shock protein, alpha-crystallin-related, B6 |
| N4BP3 | NEDD4 binding protein 3 |
| MEGF8 | multiple EGF-like-domains 8 |
| CTTN | cortactin |
| SP140L | SP140 nuclear body protein-like |
| ATP2C2 | ATPase, Ca++ transporting, type 2C, member 2 |
| DOK5 | docking protein 5 |
| LOC100170939 | glucuronidase, beta pseudogene |
| CXCL5 | chemokine (C—X—C motif) ligand 5 |
| TM4SF1 | transmembrane 4 L six family member 1 |
| RC3H1 | ring finger and CCCH-type domains 1 |
| SLC35E2 | solute carrier family 35, member E2 |
| KRT86 /// LOC100509764 | keratin 86 /// uncharacterized LOC100509764 |
| PRSS3P2 | protease, serine, 3 pseudogene 2 |
| HLA-DQB2 | major histocompatibility complex, class II, DQ beta 2 |
| CTAG2 | cancer/testis antigen 2 |
| DUOX1 | dual oxidase 1 |
| TARP /// TRGC2 | TCR gamma alternate reading frame protein /// T cell receptor gamma constant 2 |
| PTGDR | prostaglandin D2 receptor (DP) |
| GABRA2 | gamma-aminobutyric acid (GABA) A receptor, alpha 2 |
| TRDV3 | T cell receptor delta variable 3 |
| SMPD1 | sphingomyelin phosphodiesterase 1, acid lysosomal |
| FAS | Fas (TNF receptor superfamily, member 6) |
| LOC100288594 | uncharacterized LOC100288594 |
| TPSAB1 /// TPSB2 | tryptase alpha/beta 1 /// tryptase beta 2 (gene/pseudogene) |
| CCL2 | chemokine (C-C motif) ligand 2 |
| KIR3DL3 | killer cell immunoglobulin-like receptor, three domains, long cytoplasmic tail, 3 |
| FAM48A | family with sequence similarity 48, member A |
| RGS1 | regulator of G-protein signaling 1 |
| YME1L1 | YME1-like 1 (*S. cerevisiae*) |
| C14orf1 | chromosome 14 open reading frame 1 |
| LOC100287387 | Uncharacterized LOC100287387 |
| COL7A1 | collagen, type VII, alpha 1 |
| KLK13 | kallikrein-related peptidase 13 |
| LOC283683 /// LOC646278 | uncharacterized LOC283683 /// programmed cell death 6 interacting protein pseudogene |
| HAL | histidine ammonia-lyase |
| SGSM2 | small G protein signaling modulator 2 |
| TRIM44 | tripartite motif containing 44 |
| RNASET2 | ribonuclease T2 |
| CXCL14 | chemokine (C-X-C motif) ligand 14 |
| NUSAP1 | nucleolar and spindle associated protein 1 |
| CLDN1 | claudin 1 |
| MLPH | melanophilin |
| C1QA | complement component 1, q subcomponent, A chain |
| TYW1 /// TYW1B | tRNA-yW synthesizing protein 1 homolog (*S. cerevisiae*) /// tRNA-yW synthesizing protein 1 homolog B (*S. cerevisiae*) |
| SNX10 | sorting nexin 10 |
| GCFC1 | GC-rich sequence DNA-binding factor 1 |
| LIMD2 | LIM domain containing 2 |
| UPF3B | UPF3 regulator of nonsense transcripts homolog B (yeast) |
| ACP6 | acid phosphatase 6, lysophosphatidic |
| COL5A3 | collagen, type V, alpha 3 |
| SPRR3 | small proline-rich protein 3 |
| ASPN | asporin |
| DACT1 | dapper, antagonist of beta-catenin, homolog 1 (*Xenopus laevis*) |
| HSPA14 | heat shock 70 kDa protein 14 |
| ZNF331 | zinc finger protein 331 |
| ECHDC3 | enoyl CoA hydratase domain containing 3 |
| IFT81 | intraflagellar transport 81 homolog (*Chlamydomonas*) |

TABLE 15-continued

Core genes MSE 100% Severity Classifier Family: E-Min/Mild vs. E-Mod/Severe.

| Gene Symbol | Gene Title |
| --- | --- |
| NKAIN1 | Na+/K+ transporting ATPase interacting 1 |
| RAB3IL1 | RAB3A interacting protein (rabin3)-like 1 |
| ZNF767 | zinc finger family member 767 |
| ZNF606 | zinc finger protein 606 |
| ATP8A2 | ATPase, aminophospholipid transporter, class I, type 8A, member 2 |
| RASAL1 | RAS protein activator like 1 (GAP1 like) |
| ERAP2 | endoplasmic reticulum aminopeptidase 2 |
| DENND1A | DENN/MADD domain containing 1A |
| FZD10 | frizzled family receptor 10 |
| PVRIG | poliovirus receptor related immunoglobulin domain containing |
| FKRP | fukutin related protein |
| C1orf116 | chromosome 1 open reading frame 116 |
| CHODL | chondrolectin |
| FRAT1 | frequently rearranged in advanced T-cell lymphomas |
| MAGIX | MAGI family member, X-linked |
| APBB1IP | amyloid beta (A4) precursor protein-binding, family B, member 1 interacting protein |
| ZNF750 | zinc finger protein 750 |
| EPHX3 | epoxide hydrolase 3 |
| STAP1 | signal transducing adaptor family member 1 |
| CSPP1 | centrosome and spindle pole associated protein 1 |
| FXYD7 | FXYD domain containing ion transport regulator 7 |
| ALDH8A1 | aldehyde dehydrogenase 8 family, member A1 |
| FAM86C1 | family with sequence similarity 86, member C1 |
| GPR97 | G protein-coupled receptor 97 |
| UBASH3A | ubiquitin associated and SH3 domain containing A |
| CHD9 | chromodomain helicase DNA binding protein 9 |
| UIMC1 | ubiquitin interaction motif containing 1 |
| WDR19 | WD repeat domain 19 |
| ST6GALNAC5 | ST6 (alpha-N-acetyl-neuraminyl-2,3-beta-galactosyl-1,3)-N-acetylgalactosaminide alpha-2,6-sialyltransferase 5 |
| CHST8 | carbohydrate (N-acetylgalactosamine 4-0) sulfotransferase 8 |
| DENND1C | DENN/MADD domain containing 1C |
| OTOR | otoraplin |
| BACH2 | BTB and CNC homology 1, basic leucine zipper transcription factor 2 |
| YIPF5 | Yip1 domain family, member 5 |
| TBL1XR1 | transducin (beta)-like 1 X-linked receptor 1 |
| B4GALT5 | UDP-Gal:betaGlcNAc beta 1,4-galactosyltransferase, polypeptide 5 |
| HLA-DRB1 /// HLA-DRB3 /// HLA-DRB4 /// HLA-DRB5 /// LOC100507709 /// LOC100507714 /// LOC100509582 | major histocompatibility complex, class II, DR beta 1 /// major histocompatibility complex, class II, DR beta 3 /// major histocompatibility complex, class II, DR beta 4 /// major histocompatibility complex, class II, DR beta 5 /// HLA class II histocompatibility antigen, DRB1-7 beta chain-like /// HLA class II histocompatibility antigen, DRB1-7 beta chain-like /// HLA class II histocompatibility antigen, DR beta 4 chain-like |
| PARD3 | par-3 partitioning defective 3 homolog (*C. elegans*) |
| BHLHE41 | basic helix-loop-helix family, member e41 |
| GDF15 | growth differentiation factor 15 |
| ZNF83 | zinc finger protein 83 |
| AGMAT | agmatine ureohydrolase (agmatinase) |
| NLRP2 | NLR family, pyrin domain containing 2 |
| PIK3IP1 | phosphoinositide-3-kinase interacting protein 1 |
| UGCG | UDP-glucose ceramide glucosyltransferase |
| ANGEL2 | angel homolog 2 (*Drosophila*) |
| HNRNPA1 | heterogeneous nuclear ribonucleoprotein A1 |
| FLJ42627 | uncharacterized LOC645644 |
| SLCO4C1 | solute carrier organic anion transporter family, member 4C1 |
| FAM63B | family with sequence similarity 63, member B |
| DESI2 | desumoylating isopeptidase 2 |
| EGOT | eosinophil granule ontogeny transcript (non-protein coding) |
| C4orf34 | chromosome 4 open reading frame 34 |
| TUBBP5 | tubulin, beta pseudogene 5 |
| PDCD6 | Programmed cell death 6 |
| APPL1 | adaptor protein, phosphotyrosine interaction, PH domain and leucine zipper containing 1 |

TABLE 15-continued

Core genes MSE 100% Severity Classifier Family: E-Min/Mild vs. E-Mod/Severe.

| Gene Symbol | Gene Title |
|---|---|
| CPPED1 | calcineurin-like phosphoesterase domain containing 1 |
| ZAK | sterile alpha motif and leucine zipper containing kinase AZK |
| MANEA | mannosidase, endo-alpha |
| ANKH | ankylosis, progressive homolog (mouse) |
| TRIM8 | tripartite motif containing 8 |
| CGN | cingulin |
| GJB2 | gap junction protein, beta 2, 26 kDa |
| MS4A7 | membrane-spanning 4-domains, subfamily A, member 7 |
| C21orf56 | chromosome 21 open reading frame 56 |
| GBP3 | guanylate binding protein 3 |
| CRISPLD1 | cysteine-rich secretory protein LCCL domain containing 1 |
| C15orf48 | chromosome 15 open reading frame 48 |
| MGEA5 | meningioma expressed antigen 5 (hyaluronidase) |
| SEMA6B | sema domain, transmembrane domain (TM), and cytoplasmic domain, (semaphorin) 6B |
| MALAT1 | metastasis associated lung adenocarcinoma transcript 1 (non-protein coding) |
| ZMYND12 | zinc finger, MYND-type containing 12 |
| SLC4A11 | solute carrier family 4, sodium borate transporter, member 11 |
| DIO3OS | DIO3 opposite strand/antisense RNA (non-protein coding) |
| TEX101 | testis expressed 101 |
| CISH | cytokine inducible SH2-containing protein |
| CRLS1 | cardiolipin synthase 1 |
| PXMP4 | peroxisomal membrane protein 4, 24 kDa |
| PCDHA1 /// PCDHA10 /// PCDHA11 /// PCDHA12 /// PCDHA13 /// PCDHA2 /// PCDHA3 /// PCDHA4 /// PCDHA5 /// PCDHA6 /// PCDHA7 /// PCDHA8 /// PCDHA9 /// PCDHAC1 /// PCDHAC2 | protocadherin alpha 1 /// protocadherin alpha 10 /// protocadherin alpha 11 /// protocadherin alpha 12 /// protocadherin alpha 13 /// protocadherin alpha 2 /// protocadherin alpha 3 /// protocadherin alpha 4 /// protocadherin alpha 5 /// protocadherin alpha 6 /// protocadherin alpha 7 /// protocadherin alpha 8 /// protocadherin alpha 9 /// protocadherin alpha subfamily C, 1 /// protocadherin alpha subfamily C, 2 |
| MS4A8B | membrane-spanning 4-domains, subfamily A, member 8B |
| BEX2 | brain expressed X-linked 2 |
| TRPM6 | transient receptor potential cation channel, subfamily M, member 6 |
| ARHGAP9 | Rho GTPase activating protein 9 |
| SMEK2 | SMEK homolog 2, suppressor of mek1 (*Dictyostelium*) |
| KREMEN1 | kringle containing transmembrane protein 1 |
| TNFRSF18 | tumor necrosis factor receptor superfamily, member 18 |
| WASF2 | WAS protein family, member 2 |
| SNHG1 /// SNORD22 /// SNORD25 /// SNORD26 /// SNORD27 /// SNORD28 /// SNORD29 /// SNORD31 | small nucleolar RNA host gene 1 (non-protein coding) /// small nucleolar RNA, C/D box 22 /// small nucleolar RNA, C/D box 25 /// small nucleolar RNA, C/D box 26 /// small nucleolar RNA, C/D box 27 /// small nucleolar RNA, C/D box 28 /// small nucleolar RNA, C/D box 29 /// small nucleolar RNA, C/D box 31 |
| GPATCH4 | G patch domain containing 4 |
| H19 /// MIR675 | H19, imprinted maternally expressed transcript (non-protein coding) /// microRNA 675 |
| LOC100506548 /// RPL37 | uncharacterized LOC100506548 /// ribosomal protein L37 |
| GPCPD1 | glycerophosphocholine phosphodiesterase GDE1 homolog (*S. cerevisiae*) |
| SLAIN2 | SLAIN motif family, member 2 |
| PDPR | pyruvate dehydrogenase phosphatase regulatory subunit |
| ASPH | aspartate beta-hydroxylase |
| SPIRE1 | spire homolog 1 (*Drosophila*) |
| ST3GAL1 | ST3 beta-galactoside alpha-2,3-sialyltransferase 1 |
| RABEP1 | rabaptin, RAB GTPase binding effector protein 1 |
| OGFOD1 | 2-oxoglutarate and iron-dependent oxygenase domain containing 1 |
| TMEM18 | transmembrane protein 18 |
| SLC1A2 | solute carrier family 1 (glial high affinity glutamate transporter), member 2 |

TABLE 15-continued

Core genes MSE 100% Severity Classifier Family: E-Min/Mild vs. E-Mod/Severe.

| Gene Symbol | Gene Title |
| --- | --- |
| ZNF295 | zinc finger protein 295 |
| MRPL50 | mitochondrial ribosomal protein L50 |
| SLC45A4 | solute carrier family 45, member 4 |
| PAG1 | phosphoprotein associated with glycosphingolipid microdomains 1 |
| COL12A1 | collagen, type XII, alpha 1 |
| CEP95 | centrosomal protein 95 kDa |
| HNRNPU-AS1 | HNRNPU antisense RNA 1 (non-protein coding) |
| CGNL1 | cingulin-like 1 |
| EIF2C2 | eukaryotic translation initiation factor 2C, 2 |
| PHLDA1 | pleckstrin homology-like domain, family A, member 1 |
| DDHD1 | DDHD domain containing 1 |
| BPIFB1 | BPI fold containing family B, member 1 |
| SYT13 | synaptotagmin XIII |
| ELL2 | elongation factor, RNA polymerase II, 2 |
| ZFP90 | zinc finger protein 90 homolog (mouse) |
| LOC100288152 | uncharacterized LOC100288152 |
| COL8A1 | collagen, type VIII, alpha 1 |
| CLCN5 | chloride channel, voltage-sensitive 5 |
| DNER | delta/notch-like EGF repeat containing |
| SPTBN1 | spectrin, beta, non-erythrocytic 1 |
| ZMAT1 | zinc finger, matrin-type 1 |
| AMMECR1 | Alport syndrome, mental retardation, midface hypoplasia and elliptocytosis chromosomal region gene 1 |
| RMI2 | RMI2, RecQ mediated genome instability 2, homolog (*S. cerevisiae*) |
| TM7SF3 | transmembrane 7 superfamily member 3 |
| NHSL1 | NHS-like 1 |
| HINT3 | histidine triad nucleotide binding protein 3 |
| CD109 | CD109 molecule |
| GTPBP5 | GTP binding protein 5 (putative) |
| ZNF251 | zinc finger protein 251 |
| C8orf42 | chromosome 8 open reading frame 42 |
| ADAMTS9 | ADAM metallopeptidase with thrombospondin type 1 motif, 9 |
| FST | follistatin |
| UNC5B | unc-5 homolog B (*C. elegans*) |
| LRIG3 | leucine-rich repeats and immunoglobulin-like domains 3 |
| SOX8 | SRY (sex determining region Y)-box 8 |
| DEPDC1B | DEP domain containing 1B |
| NOTCH2NL | notch 2 N-terminal like |
| GLT8D2 | glycosyltransferase 8 domain containing 2 |
| INHBA | inhibin, beta A |
| ELOVL7 | ELOVL fatty acid elongase 7 |
| SUSD3 | sushi domain containing 3 |
| KIAA1211 | KIAA1211 |
| POC5 | POC5 centriolar protein homolog (*Chlamydomonas*) |
| CCT6P1 /// CCT6P3 | chaperonin containing TCP1, subunit 6 (zeta) pseudogene 1 /// chaperonin containing TCP1, subunit 6 (zeta) pseudogene 3 |
| VGLL3 | vestigial like 3 (*Drosophila*) |
| FOXQ1 | forkhead box Q1 |
| MGC16121 /// MIR503 | uncharacterized protein MGC16121 /// microRNA 503 |
| GFRA1 | GDNF family receptor alpha 1 |
| TSPAN11 | tetraspanin 11 |
| FBXL16 | F-box and leucine-rich repeat protein 16 |
| TMEM63C | transmembrane protein 63C |
| RBMXL1 | RNA binding motif protein, X-linked-like 1 |
| PDCD5 | programmed cell death 5 |
| C16orf74 | chromosome 16 open reading frame 74 |
| FMNL3 | formin-like 3 |
| LOC154761 | family with sequence similarity 115, member C pseudogene |
| LOC100506234 /// TMEM185A | uncharacterized LOC100506234 /// transmembrane protein 185A |
| FGD4 | FYVE, RhoGEF and PH domain containing 4 |
| ZG16B | zymogen granule protein 16 homolog B (rat) |
| LRCH3 | leucine-rich repeats and calponin homology (CH) domain containing 3 |
| CTXN1 | cortexin 1 |
| CP | ceruloplasmin (ferroxidase) |
| SORCS1 | sortilin-related VPS10 domain containing receptor 1 |
| ZNF252P | zinc finger protein 252, pseudogene |

TABLE 15-continued

Core genes MSE 100% Severity Classifier Family: E-Min/Mild vs. E-Mod/Severe.

| Gene Symbol | Gene Title |
| --- | --- |
| GAS5 /// SNORD44 /// SNORD47 /// SNORD76 /// SNORD77 /// SNORD79 /// SNORD80 /// SNORD81 | growth arrest-specific 5 (non-protein coding) /// small nucleolar RNA, C/D box 44 /// small nucleolar RNA, C/D box 47 /// small nucleolar RNA, C/D box 76 /// small nucleolar RNA, C/D box 77 /// small nucleolar RNA, C/D box 79 /// small nucleolar RNA, C/D box 80 /// small nucleolar RNA, C/D box 81 |
| AGR3 | anterior gradient 3 homolog (*Xenopus laevis*) |
| LOC283788 | FSHD region gene 1 pseudogene |
| CLDN11 | claudin 11 |
| NANOS1 | nanos homolog 1 (*Drosophila*) |
| C1orf162 | chromosome 1 open reading frame 162 |
| DPP6 | dipeptidyl-peptidase 6 |
| ODF2L | outer dense fiber of sperm tails 2-like |
| SNHG9 /// SNORA78 | small nucleolar RNA host gene 9 (non-protein coding) /// small nucleolar RNA, H/ACA box 78 |
| SOX7 | SRY (sex determining region Y)-box 7 |
| FLJ43663 | uncharacterized LOC378805 |
| RAB27B | RAB27B, member RAS oncogene family |
| CD36 | CD36 molecule (thrombospondin receptor) |
| PTGR1 | prostaglandin reductase 1 |
| ATF7 | activating transcription factor 7 |
| DERL3 | derlin 3 |
| CES4A | carboxylesterase 4A |
| DACH1 | dachshund homolog 1 (*Drosophila*) |
| C9orf24 | chromosome 9 open reading frame 24 |
| SARNP | SAP domain containing ribonucleoprotein |
| C17orf100 | chromosome 17 open reading frame 100 |
| PRTG | protogenin |
| PROK1 | prokineticin 1 |
| PRTG | protogenin |
| ATG9B | autophagy related 9B |
| LOC728613 | programmed cell death 6 pseudogene |
| ANKRD28 | ankyrin repeat domain 28 |
| ATG16L2 | autophagy related 16-like 2 (*S. cerevisiae*) |
| RBM26 | RNA binding motif protein 26 |
| IFIT3 | interferon-induced protein with tetratricopeptide repeats 3 |
| FAM46B | family with sequence similarity 46, member B |
| C14orf118 | chromosome 14 open reading frame 118 |
| ZNF502 | zinc finger protein 502 |
| C20orf85 | chromosome 20 open reading frame 85 |
| DISP2 | dispatched homolog 2 (*Drosophila*) |
| FAM132B | family with sequence similarity 132, member B |
| LOC728431 | uncharacterized LOC728431 |
| SMTNL2 | smoothelin-like 2 |
| ZNF207 | zinc finger protein 207 |
| SNAP23 | synaptosomal-associated protein, 23 kDa |
| FAM166B | family with sequence similarity 166, member B |
| PI15 | peptidase inhibitor 15 |
| EWSR1 | Ewing sarcoma breakpoint region 1 |
| RNF213 | ring finger protein 213 |
| CDCA7 | cell division cycle associated 7 |
| PITPNM3 | PITPNM family member 3 |
| LOC220729 /// SDHA /// SDHAP1 /// SDHAP2 | succinate dehydrogenase complex, subunit A, flavoprotein (Fp) pseudogene /// succinate dehydrogenase complex, subunit A, flavoprotein (Fp) /// succinate dehydrogenase complex, subunit A, flavoprotein pseudogene 1 /// succinate dehydrogenase complex, subunit A, flavoprotein pseudogene 2 |
| USP53 | ubiquitin specific peptidase 53 |
| F2RL2 | coagulation factor II (thrombin) receptor-like 2 |
| DDX17 | DEAD (Asp-Glu-Ala-Asp) box helicase 17 |
| LOC100507100 | uncharacterized LOC100507100 |
| C2orf82 | chromosome 2 open reading frame 82 |
| LPAR5 | lysophosphatidic acid receptor 5 |
| BAG5 | BCL2-associated athanogene 5 |
| LOC100507008 | uncharacterized LOC100507008 |
| PKHD1L1 | polycystic kidney and hepatic disease 1 (autosomal recessive)-like 1 |
| MIR210HG | MIR210 host gene (non-protein coding) |
| FAM210A | family with sequence similarity 210, member A |
| LOC100505875 | uncharacterized LOC100505875 |
| ACRBP | acrosin binding protein |
| SPG7 | spastic paraplegia 7 (pure and complicated autosomal recessive) |

TABLE 15-continued

Core genes MSE 100% Severity Classifier Family: E-Min/Mild vs. E-Mod/Severe.

| Gene Symbol | Gene Title |
| --- | --- |
| PALM3 | paralemmin 3 |
| C1orf194 | chromosome 1 open reading frame 194 |
| C1orf192 | chromosome 1 open reading frame 192 |
| MIR30C2 | microRNA 30c-2 |
| IP6K3 | inositol hexakisphosphate kinase 3 |
| WIPF1 | WAS/WASL interacting protein family, member 1 |
| FDPSL2A | MGC44478 |
| GBP1 | guanylate binding protein 1, interferon-inducible |
| GJB6 | gap junction protein, beta 6, 30 kDa |
| EOMES | eomesodermin |
| NOG | noggin |
| FLJ14186 /// LOC441124 /// LOC729021 /// LOC729218 | uncharacterized LOC401149 /// uncharacterized LOC441124 /// uncharacterized LOC729021 /// uncharacterized LOC729218 |
| KRT80 | keratin 80 |
| NCKAP5L | NCK-associated protein 5-like |
| C16orf53 | chromosome 16 open reading frame 53 |
| DCAF17 | DDB1 and CUL4 associated factor 17 |
| IKZF2 | IKAROS family zinc finger 2 (Helios) |
| FILIP1 | filamin A interacting protein 1 |
| BICD1 | bicaudal D homolog 1 (*Drosophila*) |
| ZNF678 | zinc finger protein 678 |
| EPPK1 | epiplakin 1 |
| NKD2 | naked cuticle homolog 2 (*Drosophila*) |
| ULK4 | unc-51-like kinase 4 (*C. elegans*) |
| SLA2 | Src-like-adaptor 2 |
| ZNF880 | zinc finger protein 880 |
| ZNF274 | zinc finger protein 274 |
| COL3A1 | Collagen, type III, alpha 1 |
| TRMT13 | tRNA methyltransferase 13 homolog (*S. cerevisiae*) |
| RALGAPA2 | Ral GTPase activating protein, alpha subunit 2 (catalytic) |
| MEGF10 | multiple EGF-like-domains 10 |
| SP3 | Sp3 transcription factor |
| PROK2 | prokineticin 2 |
| LOXL1-AS1 | LOXL1 antisense RNA 1 (non-protein coding) |
| ANXA1 | Annexin A1 |
| NTNG2 | netrin G2 |
| CCDC114 | coiled-coil domain containing 114 |
| KIAA1609 | KIAA1609 |
| RAB12 | RAB12, member RAS oncogene family |
| KCNK3 | potassium channel, subfamily K, member 3 |
| GNGT2 | guanine nucleotide binding protein (G protein), gamma transducing activity polypeptide 2 |
| GIMAP8 | GTPase, IMAP family member 8 |
| C14orf28 | chromosome 14 open reading frame 28 |
| LOC100507316 | uncharacterized LOC100507316 |
| LRPAP1 | low density lipoprotein receptor-related protein associated protein 1 |
| DLGAP1 | discs, large (*Drosophila*) homolog-associated protein 1 |
| GPAT2 | glycerol-3-phosphate acyltransferase 2, mitochondrial |
| MASP1 | mannan-binding lectin serine peptidase 1 (C4/C2 activating component of Ra-reactive factor) |
| LOC100422737 | uncharacterized LOC100422737 |
| MRTO4 | mRNA turnover 4 homolog (*S. cerevisiae*) |
| SCARA5 | scavenger receptor class A, member 5 (putative) |
| YPEL4 | yippee-like 4 (*Drosophila*) |
| CDK9 | cyclin-dependent kinase 9 |
| KIAA1609 | KIAA1609 |
| CAPSL | calcyphosine-like |
| VPS13B | vacuolar protein sorting 13 homolog B (yeast) |
| RDH5 | retinol dehydrogenase 5 (11-cis/9-cis) |
| FAM3C | family with sequence similarity 3, member C |
| PTPN5 | protein tyrosine phosphatase, non-receptor type 5 (striatum-enriched) |
| TMEM132B | transmembrane protein 132B |
| GPR110 | G protein-coupled receptor 110 |
| BCL2L10 | BCL2-like 10 (apoptosis facilitator) |
| ZNF667 | zinc finger protein 667 |
| GSG1L | GSG1-like |
| CCDC78 | coiled-coil domain containing 78 |
| LHFPL3 | lipoma HMGIC fusion partner-like 3 |
| HOXB-AS3 | HOXB cluster antisense RNA 3 (non-protein coding) |
| HGD | homogentisate 1,2-dioxygenase |

TABLE 15-continued

Core genes MSE 100% Severity Classifier Family: E-Min/Mild vs. E-Mod/Severe.

| Gene Symbol | Gene Title |
| --- | --- |
| SLC6A13 | solute carrier family 6 (neurotransmitter transporter, GABA), member 13 |
| PRKRA | protein kinase, interferon-inducible double stranded RNA dependent activator |
| PCNP | PEST proteolytic signal containing nuclear protein |
| SOX5 | SRY (sex determining region Y)-box 5 |
| PLEKHA2 | pleckstrin homology domain containing, family A (phosphoinositide binding specific) member 2 |
| ARID1B | AT rich interactive domain 1B (SWI1-like) |
| HAP1 | huntingtin-associated protein 1 |
| TMEM136 | transmembrane protein 136 |
| C11orf80 | chromosome 11 open reading frame 80 |
| C1orf168 | chromosome 1 open reading frame 168 |
| MTHFD2L | methylenetetrahydrofolate dehydrogenase (NADP+ dependent) 2-like |
| LOC494150 | prohibitin pseudogene |
| AVPR1A | arginine vasopressin receptor 1A |
| NSUN7 | NOP2/Sun domain family, member 7 |
| DOCK8 | dedicator of cytokinesis 8 |
| MTHFR | methylenetetrahydrofolate reductase (NAD(P)H) |
| ZNF786 | zinc finger protein 786 |
| LOC100505912 | uncharacterized LOC100505912 |
| FBXL20 | F-box and leucine-rich repeat protein 20 |
| PLCXD3 | phosphatidylinositol-specific phospholipase C, X domain containing 3 |
| CEP152 | centrosomal protein 152 kDa |
| RBP1 | retinol binding protein 1, cellular |
| HOXA11-AS | HOXA11 antisense RNA (non-protein coding) |
| ACOXL | acyl-CoA oxidase-like |
| ZFYVE16 | zinc finger, FYVE domain containing 16 |
| HR | hairless homolog (mouse) |
| CCDC15 | coiled-coil domain containing 15 |
| NUPL1 | nucleoporin like 1 |
| SCNN1G | sodium channel, non-voltage-gated 1, gamma subunit |
| C6orf132 | chromosome 6 open reading frame 132 |
| CPM | carboxypeptidase M |
| NFKBID | nuclear factor of kappa light polypeptide gene enhancer in B-cells inhibitor, delta |
| XDH | xanthine dehydrogenase |
| ANKRD33 | ankyrin repeat domain 33 |
| C1QTNF6 | C1q and tumor necrosis factor related protein 6 |
| LOC100505648 | uncharacterized LOC100505648 |
| ZNF420 | zinc finger protein 420 |
| LOC642236 | FSHD region gene 1 pseudogene |
| MAP6D1 | MAP6 domain containing 1 |
| LOC100506303 /// LOC100653149 /// LOC400879 | uncharacterized LOC100506303 /// uncharacterized LOC100653149 /// uncharacterized LOC400879 |
| PIP5KL1 | phosphatidylinositol-4-phosphate 5-kinase-like 1 |
| DCAF8 | DDB1 and CUL4 associated factor 8 |
| CASZ1 | castor zinc finger 1 |
| KANSL1 | KAT8 regulatory NSL complex subunit 1 |
| WDR38 | WD repeat domain 38 |
| ZNF793 | zinc finger protein 793 |
| ZNF300P1 | zinc finger protein 300 pseudogene 1 |
| LOC100505679 | uncharacterized LOC100505679 |
| CYCS | cytochrome c, somatic |
| MTHFSD | methenyltetrahydrofolate synthetase domain containing |
| PHACTR2 | phosphatase and actin regulator 2 |
| SGPP2 | sphingosine-1-phosphate phosphatase 2 |
| CRP | C-reactive protein, pentraxin-related |
| AQP3 | aquaporin 3 (Gill blood group) |
| EPOR | erythropoietin receptor |
| CELSR1 | cadherin, EGF LAG seven-pass G-type receptor 1 (flamingo homolog, *Drosophila*) |
| LZTS1 | leucine zipper, putative tumor suppressor 1 |
| RAB15 | RAB15, member RAS oncogene family |
| ZNF814 | zinc finger protein 814 |
| ZNF718 | Zinc finger protein 718 |
| DUSP5P | dual specificity phosphatase 5 pseudogene |
| MFSD2A | major facilitator superfamily domain containing 2A |
| HINT1 | histidine triad nucleotide binding protein 1 |
| VASH1 | Vasohibin 1 |
| LOC440993 | uncharacterized LOC440993 |
| SLC38A10 | solute carrier family 38, member 10 |

TABLE 15-continued

Core genes MSE 100% Severity Classifier Family: E-Min/Mild vs. E-Mod/Severe.

| Gene Symbol | Gene Title |
| --- | --- |
| RPS16P5 | ribosomal protein S16 pseudogene 5 |
| SNORD8 | small nucleolar RNA, C/D box 8 |
| DEFB124 | defensin, beta 124 |
| LOC100505812 | uncharacterized LOC100505812 |
| TRIM13 | tripartite motif containing 13 |
| GPBP1L1 | GC-rich promoter binding protein 1-like 1 |
| TECR | trans-2,3-enoyl-CoA reductase |
| MLX | MAX-like protein X |
| MPZL3 | myelin protein zero-like 3 |
| LSM4 | LSM4 homolog, U6 small nuclear RNA associated (*S. cerevisiae*) |
| PCBP2 | poly(rC) binding protein 2 |
| MYL6 | myosin, light chain 6, alkali, smooth muscle and non-muscle |
| NENF | Neudesin neurotrophic factor |
| SH3BP2 | SH3-domain binding protein 2 |
| LOC100653010 | uncharacterized LOC100653010 |
| ERV3-2 | endogenous retrovirus group 3, member 2 |
| PRO2852 | uncharacterized protein PRO2852 |
| LMCD1 | LIM and cysteine-rich domains 1 |
| NUDT4 | Nudix (nucleoside diphosphate linked moiety X)-type motif 4 |
| CRIM1 | Cysteine rich transmembrane BMP regulator 1 (chordin-like) |
| SRGAP2P1 | SLIT-ROBO Rho GTPase activating protein 2 pseudogene 1 |
| DCBLD2 | Discoidin, CUB and LCCL domain containing 2 |
| ORAI2 | ORAI calcium release-activated calcium modulator 2 |
| LOC100653336 /// PGM5-AS1 | uncharacterized LOC100653336 /// PGM5 antisense RNA 1 (non-protein coding) |
| RAPH1 | Ras association (RalGDS/AF-6) and pleckstrin homology domains 1 |
| CDAN1 | Congenital dyserythropoietic anemia, type I |
| LOC100506941 | uncharacterized LOC100506941 |
| LOC100506165 | uncharacterized LOC100506165 |
| B2M | Beta-2-microglobulin |
| KRR1 | KRR1, small subunit (SSU) processome component, homolog (yeast) |
| BCAR1 | breast cancer anti-estrogen resistance 1 |
| EBF1 | Early B-cell factor 1 |
| UBE2I | ubiquitin-conjugating enzyme E2I |
| CDC14B | CDC14 cell division cycle 14 homolog B (*S. cerevisiae*) |
| SNORD3B-1 /// SNORD3B-2 /// SNORD3D | small nucleolar RNA, C/D box 3B-1 /// small nucleolar RNA, C/D box 3B-2 /// small nucleolar RNA, C/D box 3D |
| NSD1 | nuclear receptor binding SET domain protein 1 |
| DCAF7 | DDB1 and CUL4 associated factor 7 |
| SUZ12P | Suppressor of zeste 12 homolog pseudogene |
| IFNAR1 | Interferon (alpha, beta and omega) receptor 1 |
| NUP62 | Nucleoporin 62 kDa |
| LOC100134445 | uncharacterized LOC100134445 |
| WWC1 | WW and C2 domain containing 1 |
| IRS1 | insulin receptor substrate 1 |
| LOC100653149 | uncharacterized LOC100653149 |
| RNF144B | Ring finger protein 144B |
| DAPK1-IT1 | DAPK1 intronic transcript 1 (non-protein coding) |
| SLC2A8 | Solute carrier family 2 (facilitated glucose transporter), member 8 |
| LOC441179 | uncharacterized LOC441179 |
| ZFAND6 | Zinc finger, AN1-type domain 6 |
| LOC100507153 | uncharacterized LOC100507153 |
| PSMG4 | Proteasome (prosome, macropain) assembly chaperone 4 |
| NAMPT | Nicotinamide phosphoribosyltransferase |
| ZNF652 | Zinc finger protein 652 |
| RAB18 | RAB18, member RAS oncogene family |
| MUC20 | mucin 20, cell surface associated |

Tables 16-18 provide expression data for representative probe sets that were used in the phase-specific classifiers. Table 16 shows all the probe sets for the phase-specific disease classifiers that distinguish the first node of the decision tree (no pathology (NE.NUP) vs. disease (E+NE.U-CUP), and all the probe sets for the phase-specific disease classifiers that distinguish the second node of the decision tree (NE.UCUP vs E). Table 17 shows all the probe sets for the phase-specific severity classifiers that distinguish the third node of the decision tree (E.MinMild vs E.Mod/Severe). Table 18 shows the expression data and gene names for all the probe sets in Tables 16 and 17.

REFERENCES

1. Sheldon E, Vo K C, McIntire R A, Aghajanova L, Zelenko Z, Irwin J C, Giudice L C. Biobanking human endometrial tissue and blood specimens: standard operating procedure and importance to reproductive biology research and diagnostic development. Fertil Steril. 2011; 95(6):2120-2.
2. Tibshirani, R. and T. Hastie, 2007: Margin Trees for High-dimensional Classification. Journal of Machine Learning Research, volume 8, pages 637-652).

APPENDIX

Sample R Script Illustrating Methodology for Classifier Development

```

#   R Script: classifier.binary.phasespecific.PE.severity.random.trials.R

#   Author: John S. Tamaresis, PhD
#   Created: 23-Mar-2012
#   Updated: 23-Mar-2012

#   Load packages.
    require(affy)
    require(sampling)
    require(marginTree)
#   Source this function to create non-overlapping cross-validation folds.
    source('cross.validation.folds.R')
#   Initializations
    #   Number of random trials
    numRandomTrials = 250
    #   Vector of stratum sizes based on 80%-20% split between construction
    #   and validation sets. The "strata" function in the "sampling" package
    #   chooses the strata in alphabetical order: E.MinimalMild,
E.ModerateSevere.
    strata.sizes.vec <- c(9,13)
    #   Number of cross-validation folds. Ensure that the stratum sizes
    #   equal or exceed this number.
    numCV <- min(c(10,min(strata.sizes.vec)))
    #   Use prime numbers as seeds for random sampling.
    require(randtoolbox)
    seeds.vec <- get.primes(numRandomTrials)
    unloadNamespace('randtoolbox')
    unloadNamespace('rngWELL')
    #   Validation error vector
    val.error.vec <- vector(mode='numeric', length=numRandomTrials)
#   Load normalized expression data.
    load(file='../data/master.ver07.gcrma.Rdata')
#   Create the data set.
    master.ver07.PE.df <- subset(x=master.ver07.df, subset=(Phase=='PE') &
(Severity %in% c('MinimalMild','ModerateSevere')))
    master.ver07.PE.df$Phase <- master.ver07.PE.df$Phase[,drop=TRUE]
    data.df <- transform(master.ver07.PE.df, Class=paste (Disease, Severity,
sep='.'))
    # Reorder the data.
    learningset.df <- data.df[order(data.df$Class),]
    learningset.df$Class <- factor(x=learningset.df$Class,
levels=c('E.MinimalMild','E.ModerateSevere'), ordered=TRUE)
#   Perform the random trials.
    for(indx.seed in 1:numRandomTrials){
        #   Initializations
        folds.lst <- vector(mode='list', length=numCV)
        #   Seed for random sampling.
        set.seed(seeds.vec[indx.seed])
        #   Divide learning set into construction and validation sets.
        construction.strt    <- strata(data=learningset.df, stratanames='Class',
size=strata.sizes.vec, method="srswor")
        construction.df      <- getdata(data=learningset.df, m=construction.strt)
        validation.df        <- subset(x=learningset.df, subset=!(Sample %in %
construction.df$Sample))
        #   Severity classifier for samples independent of phase status
        #   Assign the samples to each fold. Select non-overlapping folds for k-
fold cross-validation
        #   to be consistent with the classification algorithm.
        construction.df <- transform (construction.df,
```

```
CVFold=unlist(lapply(1:nlevels(learningset.df$Class), function(ir)
cross.validation.folds.fcn(numFolds=numCV,
numElements = strata.sizes.vec[ir])))
        #   Store each fold in list.
        for(ifold in 1:numCV){
            folds.lst[[ifold]] <- which(construction.df$CVFold==ifold)
        }
        #   Create classifier using Margin Trees.
        #   Extract desired samples.
        construction.eset <-
t(exprs(master.ver07.gcrma)[,construction.df$Sample])
        #   Train classifier.
        Severity.mrgntr <- marginTree (x=construction.eset,
y=construction.df$Class)
        #   Cross-validate classifier.
        Severity.mrgntrcv <- marginTree.cv(x=construction.eset,
y=construction.df$Class, train.obj=Severity.mrgntr, folds = folds.lst)
        #   Choose the threshold value that minimizes the overall error under
cross-validation.
        threshold.vec <-
Severity.mrgntrcv$threshold[which(Severity.mrgntrcv$error==min(Severity.mrg
ntrcv$error))]
        #   If there are multiple minima, choose the smallest validation error.
        error.vec <- vector(mode='numeric',length=length(threshold.vec))
        for(indx in 1:length(threshold.vec)){
            Severity.mrgntrprdct <- marginTree.predict (train.obj=Severity.mrgntr,
x=t(exprs(master.ver07.gcrma)[,validation.df$Sample]),
threshold=threshold.vec[indx])
            error.vec[indx] <- sum(as.numeric(validation.df$Class !=
factor(x=Severity.mrgntrprdct, levels=levels(validation.df$Class),
ordered=TRUE)))/as.numeric(nrow(validation.df))
        }
        val.error.vec[indx.seed] <- min(error.vec)
        #   Store data from each run.
        binary.lst <- list(Seed=seeds.vec[indx.seed], CVFolds=folds.lst,
Construction=construction.df, Validation=validation.df,
Train=Severity.mrgntr, CVTrain=Severity.mrgntrcv,
CVErrorMin=min(Severity.mrgntrcv$error), ThresholdMin=threshold.vec,
Test=Severity.mrgntrprdct, TestError=error.vec)
        filename.str <-
paste('../data/classifier.binary.phasespecific.PE.severity.random.trials.se
ed', sprintf('%04i', seeds.vec[indx.seed]), 'Rdata', sep='.')
        save(binary.lst, file=filename.str)
    }
    save(list=c('seeds.vec', 'val.error.vec'),
file='../data/classifier.binary.phasespecific.PE.severity.random.trials.Rda
ta')
#   End of R Script
```

It is understood that the examples and embodiments described herein are for illustrative purposes only and that various modifications or changes in light thereof will be suggested to persons skilled in the art and are to be included within the spirit and purview of this application and scope of the appended claims. All publications, DNA and RNA sequences of the genes listed in the Tables herein, sequence accession numbers, patents, and patent applications cited herein are hereby incorporated by reference in their entirety for all purposes.

What is claimed is:

1. A method for diagnosing and treating endometriosis, comprising:
   obtaining a tissue sample comprising endometrial cells from a subject suffering from endometriosis;
   determining the expression level of at least one set of genes, the set of genes comprising (i) 603190322F1 NIH_MGC_95 *Homo sapiens* cDNA clone IMAGE:5261717 5 (GenBank: BI547087), 602415167F1 NIH_MGC_92 *Homo sapiens* cDNA clone IMAGE:4523513 5 (GenBank: BG389789), FBJ murine osteosarcoma viral oncogene homolog B (FOSB) (GenBank: NM 006732), deiodinase, iodothyronine, type II (DI02), DEAD (Asp-Glu-Ala-Asp) box polypeptide 17 (DDX17) (Genbank Nos: Z97056, AA521056, U59321, AW188131, NM 030881), FBJ murine osteosarcoma viral oncogene homolog (FOS) (GenBank: BC004490), metastasis associated lung adenocarcinoma transcript 1 (MALAT1), and sentan, cilia apical structure protein (SNTN); or
(ii) solute carrier family 8 (sodium/calcium exchanger), member 1 (SLC8A1) (GenBank: AW452398), programmed cell death 6 pseudogene (LOC728613), Lactotransferrin (LTF) (GenBank: NM 002343), major histocompatibility complex, class II, DQ alpha 1 (HLA-DQA1), solute carrier family 7 (cationic amino acid transporter, y+system), member 4 (SLC7A4) (GenBank: NM 004173), protocadherin 8 (PCDH8), cyclin-dependent kinase inhibitor 2A (CDKN2A), mucin 5B, oligomeric mucus/gel-forming (MUCSB), IQ motif containing GTPase activating protein 1 (IQGAP1), RNA binding motif protein 6 (RBM6), aa71e05.s1 NCI CGAP GCB1 *Homo sapiens* cDNA clone IMAGE:826400 3-, mRNA sequence (GenBank: AA521056), DDX17, secretoglobin, family 3A, member 1 (SCGB3A1), hi56d01.x1 Soares NFL T GBC S1 *Homo sapiens* cDNA clone IMAGE:2976289 3-, mRNA sequence (GenBank: AW629304), hypothetical LOC401522 (LOC401522), Nuclear autoantigenic sperm protein (histone-binding) (NASP), and Actin, alpha 2, smooth muscle, aorta (ACTA2); or (iii) anillin, actin binding protein (ANLN) (Genbank: AK023208, NM 018685), hypothetical protein BC008131 (LOC142937), GINS complex subunit 4 (GINS4) (S1d5homolog), vimentin (VIM), Hypothetical protein LOC100127980 (LOC100127980), wg08h02.x1 Soares NSF F8 9_W_OT_PA_P_S1 Homo sapiens cDNA clone IMAGE:2364531 3-, mRNA sequence (GenBank: AI741292), Homo sapiens genomic DNA (GenBank: AL390180), hypothetical LOC100505967 (LOC100505967), Homo sapiens mRNA; cDNA DKFZp686A22111 (GenBank: AL832142), Homo sapiens cDNA: F1122384 fis, clone HRC07594 (GenBank: AK026037), caspase 8 associated protein 2 (CASP8AP2), lactotransferrin (LTF), fibrillin 1 (FBN1) Genbank: NM 000138, AW955612, cadherin 3, type 1, P-cadherin (placental) (CDH3), EPH receptor A2 (EPHA2), glutathione S-transferase theta 1 (GSTT1), microtubule-associated protein, RP/EB family, member 3 (MAPRE3), protein kinase, X-linked /// protein kinase, Y-linked (PRKX /// PRKY), protein kinase, X-linked (PRKX), glutathione S-transferase mu 4 (GSTM4), solute carrier family 12 (sodium/potassium/chloride transporters), member 2 (SLC12A2), glutathione S-transferase mu 2 (muscle) (GSTM2), FOS-like antigen 1 (FOSL1), glutathione S-transferase mu 1 (GSTM1), hydroxysteroid (17-beta) dehydrogenase 2 (HSD17B2), N-myristoyltransferase 2 (NMT2), gamma-aminobutyric acid (GABA) A receptor, pi (GABRP), PDZ domain containing 1 (PDZK1), vanin 1 (VNN1), phospholipase C-like 1 (PLCL1), renin (REN), carcinoembryonic antigen-related cell adhesion molecule 1 (biliary glycoprotein) (CEACAM1), crystallin, beta B2 /// crystallin, beta B2 pseudogene 1 (CRYBB2/// CRYBB2P1), secretoglobin, family 1D, member 2 (SCGB1D2), latrophilin 2 (LPHN2), cyclin-dependent kinase inhibitor 2A (melanoma, p16, inhibits CDK4) (CDKN2A), secreted frizzled-related protein 5 (SFRP5), DNA segment on chromosome 4 (unique) 234 expressed sequence (D4S234E), bone morphogenetic protein 7 (BMP7), v-myc myelocytomatosis viral related oncogene, neuroblastoma derived (avian) (MYCN), protein tyrosine phosphatase, non-receptor type 11 (PTPN11), splicing factor 1 (SF1), granzyme H (cathepsin G-like 2, protein h-CCPX) (GZMH), fibroblast growth factor 18 (FGF18), paternally expressed 10 (PEG10), solute carrier family 7 (cationic amino acid transporter, y+system), member 1 (SLC7A1), mucin 5B, oligomeric mucus/gel-forming (MUC5B), tb81b07.x1 NCI CGAP Lu26 Homo sapiens cDNA clone IMAGE:2060725 3- similar to gb:M10119 FERRITIN LIGHT CHAIN (HUMAN); mRNA sequence (GenBank: AI345238), carcinoembryonic antigen-related cell adhesion molecule 21 (CEACAM21), ys84f02.s1Soares retina N2b4 HR Homo sapiens cDNA clone IMAGE:221499 3- similar to contains Alu repetitive element;contains PTR5 repetitive element, mRNA sequence (GenBank: H92070), caldesmon 1 (CALD1), tryptase alpha-1-like /// tryptase alpha/beta 1 (LOC100507804 /// TPSAB1), hydatidiform mole associated and imprinted (non-protein coding) (HYMAI), SET translocation (myeloid leukemia-associated) pseudogene /// SET nuclear oncogene (LOC642869 /// SET), KIAA1661 protein (KIAA1661), Family with sequence similarity 48, member A (FAM48A), brain expressed, X-linked 1 (BEX1), syntabulin (syntaxin-interacting) (SYBU), endothelin converting enzyme-like 1 (ECEL1), helicase, lymphoid-specific (HELLS), zinc finger, B-box domain containing (ZBBX), IQ motif containing G (IQCG), kelch-like 24 (Drosophila) (KLHL24), hypothetical LOC389906 (LOC389906), hypothetical LOC100510224 (LOC100510224), Wolf-Hirschhorn syndrome candidate 1-like 1 (WHSC1L1), transmembrane protein 106B (TMEM106B), guanine nucleotide binding protein (G protein), gamma 12 (GNG12), ectonucleotide pyrophosphatase/phosphodiesterase 3 (ENPP3), forkhead box P1 (FOXP1), hypothetical protein PRO2852 (PRO2852), SECIS binding protein 2 (SECISBP2), membrane-spanning 4-domains, subfamily A, member 8B (MS4A8B), metastasis associated lung adenocarcinoma transcript 1 (non-protein coding) (MALAT1), pyruvate dehydrogenase kinase, isozyme 4 (PDK4), small nuclear ribonucleoprotein polypeptide N (SNRPN), family with sequence similarity 110, member C (FAM110C). hypothetical LOC100131564 (LOC100131564), hypothetical protein LOC727820 (LOC727820), endoplasmic reticulum aminopeptidase 2 (ERAP2), serologically defined colon cancer antigen 8 (SDCCAG8), Na+/K+transporting ATPase interacting 4 (NKAIN4), nk67dZ10.s1NCI CGAP Sch1 Homo sapiens cDNA clone IMAGE:1018579 3-, mRNA sequence (GenBank: AA601031), $CDCl_42$ small effector 2 ($CDCl_4$2SE2), EMI domain containing 2 (EMID2), golgi transport 1A (GOLT1A), solute carrier family 20 (phosphate transporter), member 1 (SLC20A1), polycystic kidney and hepatic disease 1 (autosomal recessive)-like 1 (PKHD1L1), 7g45a06.x1NCI CGAP Pr28 Homo sapiens cDNA clone IMAGE:3309394 3-, mRNA sequence (GenBank: BE858984), tw52g09.x1NCI CGAP Utl Homo sapiens cDNA clone IMAGE:2263360 3-, mRNA sequence (GenBank: AI683621), hypothetical LOC100506125 (LOC100506125), F-box protein 15 (FBXO15), AV660825 GLC Homo sapiens cDNA clone GLCGLGO3 3-, mRNA sequence (GenBank: AV660825), hypothetical LOC253039 (LOC253039), Homo sapiens genomic DNA;

cDNA DKFZp434K1111 (GenBank: AL157491), Homo sapiens clone IMAGE:297403, mRNA sequence (GenBank: AF339813), Sp3 transcription factor (SP3), AU144005 HEMBA1 Homo sapiens cDNA clone HEMBA1000622 3-, mRNA sequence (GenBank: AU144005), Homo sapiens PRO1550 mRNA, partial cds (GenBank: AF119847), UI—H—BWO-aiy-a-04-O-UI.s1 NCI CGAP Sub6 Homo sapiens cDNA clone IMAGE:2730894 3-, mRNA sequence (GenBank: AW297731), 601763318F1 NIH MGC 20 Homo sapiens cDNA clone IMAGE:4026173 5-, mRNA sequence (GenBank: BF125564),immunoglobulin-like domain containing receptor 1 (ILDR1), ar55f07.x1 Barstead aorta HPLRB6 Homo sapiens cDNA clone IMAGE: 2126533 3-, mRNA sequence (GenBank: AI431345), zo89e10.x5 Stratagene ovarian cancer (#937219) Homo sapiens cDNA clone IMAGE:594090 3-, mRNA sequence (GenBank: AI732617), nc39f01.r1 NCI CGAP Pr2 Homo sapiens cDNA clone IMAGE: 1010521, mRNA sequence (GenBank: AA228366), unc-5 homolog A (C. elegans) (UNC5A), xm39b03.x1 NCI CGAP GC6 Homo sapiens cDNA clone IMAGE:2686541 3- similar to contains element KER repetitive element; mRNA sequence (GenBank: AW197431), N(alpha)-acetyltransferase 25, NatB auxiliary subunit (NAA25), hu05h12.xl NCI CGAP Lu24 *Homo sapiens* cDNA clone IMAGE:3165767 3-, mRNA sequence (GenBank: BE222109), protein kinase, interferon-inducible double stranded RNA dependent activator (PRKRA), UI—H—BI1-afr-e-09-O-UI.s1 NCI CGAP Sub3 *Homo sapiens* cDNA clone IMAGE:2722673 3-, mRNA sequence (GenBank: AW205632), relaxin/insulin-like family peptide receptor 1 (RXFP1), 7q07e12.x1 NCI CGAP Pr28 *Homo sapiens* cDNA clone IMAGE:3676918 3-, mRNA sequence (GenBank: BF438300), 601176827F1 NIH MGC 17 *Homo sapiens* cDNA clone IMAGE:3532039 5-, mRNA sequence (GenBank: BE295812), Hypothetical F1139739 (F1139739), UI—H—BI1-aeu-f-12-O-UI.s1 NCI CGAP Sub3 *Homo sapiens* cDNA clone IMAGE:2720782 3-, mRNA sequence (GenBank: AW203986), o110a05.s1 Soares NFL T GBC S1 *Homo sapiens* cDNA clone IMAGE:1523024 3-, mRNA sequence (GenBank: AA908970), Tubby like protein 4 (TULP4), family with sequence similarity 81, member B (FAM81B), ht05b06.xl NCI CGAP Kid13 *Homo sapiens* cDNA clone IMAGE:3145811 3-, mRNA sequence (GenBank: BE349858), UI—H—BI4-aop-a-02-0-UI.s1 NCI CGAP Sub8 *Homo sapiens* cDNA clone IMAGE:3085347 3-, mRNA sequence (GenBank: BF508634), WD repeat domain 1 (WDR1), hz75g08.x1 NCI CGAP Lu24 *Homo sapiens* cDNA clone IMAGE:3213854 3-, mRNA sequence (GenBank: BE467916), chromosome 21 open reading frame 121 (C2lorf121), yi43b01.s1 Soares placenta Nb2HP *Homo sapiens* cDNA clone IMAGE:141961 3-, mRNA sequence (GenBank: R68807), xd86f06.xl Soares NFL T GBC S1 *Homo sapiens* cDNA clone IMAGE: 2604515 3-, mRNA sequence (GenBank: AW117264), nucleoporin like 1 (NUPL1), hypothetical LOC400931 (LOC400931), EST374531 MAGE resequences, MAGG *Homo sapiens* cDNA, mRNA sequence (GenBank: AW962458), Quaking homolog, KH domain RNA binding (mouse) (QKI), EST388740 MAGE resequences, MAGN *Homo sapiens* cDNA, mRNA sequence (GenBank: AW976631), af03h05.s1 Soares testis NHT *Homo sapiens* cDNA clone IMAGE:1030617 3-, mRNA sequence (GenBank: AA608834); Small nuclear ribonucleoprotein polypeptide A' (SNRPA1);

TATA element modulatory factor 1 (TMF1); iron-responsive element binding protein 2 (IREB2); additional sex combs like 1 (*Drosophila*) (ASXL1); 7j75e02.x1 Soares NSF F8 9 W OT PA P S1 *Homo sapiens* cDNA clone IMAGE:3392282 3-, mRNA sequence (GenBank: BF055144); low density lipoprotein receptor-related protein associated protein 1 (LRPAP1); yv26d08.s1 Soares fetal liver spleen 1NFLS *Homo sapiens* cDNA clone IMAGE:243855 3- similar to contains Alu repetitive element;contains element MER35 repetitive element; mRNA sequence (GenBank: N39188); wa90a01.xl NCI CGAP GC6 *Homo sapiens* cDNA clone IMAGE:2303400 3- similar to contains Alu repetitive element; mRNA sequence (GenBank: AI650364); tj84d07.x1 Soares NSF F8 9 W OT PA P S1 *Homo sapiens* cDNA clone IMAGE: 2148205 3-, mRNA sequence (GenBank: AI467945); zj20h10.s1 Soares fetal liver spleen 1NFLS S1 *Homo sapiens* cDNA clone IMAGE:450883 3-, mRNA sequence (GenBank: AA682674); RAB18, member RAS oncogene family (RAB18); gap junction protein, gamma 1, 45 kDa (GJC1); C-Maf-inducing protein (CMIP); AV691872 GKC *Homo sapiens* cDNA clone GKCDSB09 5-, mRNA sequence (GenBank: AV691872);

EST384976 MAGE resequences, MAGL *Homo sapiens* cDNA, mRNA sequence (GenBank:

AW972881); or (iv) Lysozyme (LYZ; Genbank: AV711904, U25677), periostin, osteoblast specific factor (POSTN), similar to arylacetamide deacetylase (AADAC) (LOC201651), apolipoprotein D APOD), FBJ murine osteosarcoma viral oncogene homolog B (FOSB), S100 calcium binding protein A8 (S100A8), hemoglobin, gamma A /// hemoglobin, gamma G (HBG1 /// HBG2), brain-specific angiogenesis inhibitor 3 (BAI3), cystatin SN (CST1), cystatin S (CST4), splicing factor 1 (SF1), chemokine (C—X-C motif) ligand 14 (CXCL14), TAF7-like RNA polymerase II, TATA box binding protein (TBP)-associated factor, 50 kDa (TAF7L), corin, serine peptidase (CORM), interleukin 17 receptor B (IL17RB), ganglioside-induced differentiation-associated protein 1 (GDAP1), mucin 15, cell surface associated (MUC15), Early growth response 1 (EGR1), leucine rich repeat containing 3B (LRRC3B), EPH receptor B1 (EPHB1), zo02d03.s1 Stratagene colon (#937204) *Homo sapiens* cDNA clone IMAGE:566501 3-, mRNA sequence (GenBank: AA151917), *Homo sapiens* mRNA; cDNA DKFZp761C0524 (from clone DKFZp761C0524) (GenBank: AL137429), nm30hl1.s1 NCI CGAP Lip2 *Homo sapiens* cDNA clone IMAGE:1061733, mRNA sequence (GenBank: AA569225), phosphatase and tensin homolog (PTEN), ng24h09.s1 NCI CGAP Co3 *Homo sapiens* cDNA clone IMAGE:935777 3-, mRNA sequence (GenBank: AA523939), od60e07.s1 NCI CGAP GCB1 *Homo sapiens* cDNA clone IMAGE: 1372356 3-, mRNA sequence (GenBank: AA826176), transmembrane protein 132B (TMEM132B), NCK-associated protein 5 (NCKAPS), 7g89c05.xl NCI CGAP Col6 *Homo sapiens* cDNA clone IMAGE: 3313640 3-, mRNA sequence (GenBank: BF001514), yh89f11.s1 Soares placenta Nb2HP *Homo sapiens* cDNA clone IMAGE:136941 3-, mRNA sequence (GenBank: R36546.1), ycl7gll.sl Stratagene lung (#937210) *Homo sapiens* cDNA clone IMAGE:80996 3-, mRNA sequence (GenBank: T70087.1), Nicotinamide phosphoribosyltransferase (NAMPT), EST387118 MAGE resequences, MAGN *Homo sapiens* cDNA, mRNA sequence (GenBank: AW975013), and nuclear undecaprenyl pyrophosphate synthase 1 homolog (*S. cerevisiae*) pseudogene 3 (NUS1P3); or (v) carboxyl ester lipase (bile salt-stimulated lipase) /// bile salt-activated lipase-like (CEL /// LOC100508206), UI-1-BB 1p-aut-f-08-O-UI.s1 NCI CGAP P16 *Homo sapiens* cDNA clone UI-1-BB 1p-aut-f-08-O-UI 3-, mRNA sequence (GenBank: BQ024490), AGENCOURT 10609489 NIH MGC 126 *Homo sapiens* cDNA clone IMAGE:6726950 5-, mRNA sequence (GenBank: BU955063), thrombospondin 1; Genbank Nos: BF109732, AW956580, BF084105, AI812030, NM 003246, BF055462, AV726673. (THBS1), hemoglobin, alpha 1 /// hemoglobin, alpha 2 (HBA1 /// HBA2), CD52 molecule (CD52), cystic fibrosis transmembrane conductance regulator (ATP-binding cassette sub-family C, member 7) (CFTR), glutathione S-transferase theta 2 (GSTT2), G protein-coupled receptor 64; Genbank: NM 005756. (GPR64), cysteine-rich secretory protein 3 (CRISP3), hemoglobin, beta (HBB), solute carrier family 9 (sodium/hydrogen exchanger), member 3 regulator 2 (SLC9A3R2) ADP-ribosyltransferase 3 (ART3), histone cluster 1, H2bg (HIST1H2BG), olfactomedin 4 (OLFM4), son of sevenless homolog 1 (*Drosophila*) (SOS1), mucin 5B, oligomeric mucus/gel-forming (MUCSB), galanin prepropeptide (GAL), interferon-induced protein 44 (IFI44), odontogenic, ameloblast asssociated (ODAM), cation channel, sperm-associated, beta (CATSPERB), angiotensin II receptor, type 2 (AGTR2), chromosome 15 open reading frame 48 (C15orf48), protein phosphatase 1, regulatory (inhibitor) subunit 1B (PPP1R1B), zymogen granule protein 16 homolog B (rat) (ZG16B), chromosome 20 open reading frame 54 (C20orf54), nk67d10.s1 NCI CGAP Sch1 *Homo sapiens* cDNA clone IMAGE:1018579 3-, mRNA sequence (GenBank: AA601031), qb34a07.xl Soares pregnant uterus NbHPU *Homo sapiens* cDNA clone IMAGE:1698132 3-, mRNA sequence (GenBank: AI147867), UI—H—BWO-aiy-a-04-O-UI.s1 NCI CGAP Sub6 *Homo sapiens* cDNA clone IMAGE:2730894 3-, mRNA sequence (GenBank: AW297731), coiled-coil domain containing 58 (CCDC$_1$8), 7g55h08.xl NCI CGAP Pr28 *Homo sapiens* cDNA clone IMAGE:3310431 3-, mRNA sequence (GenBank: BF003148), UI—H—BI4-aop-a-02-O-UI.s1 NCI CGAP Sub8 *Homo sapiens* cDNA clone IMAGE:3085347 3-, mRNA sequence (GenBank: BF508634), wb32f06.xl NCI CGAP GC6 *Homo sapiens* cDNA clone IMAGE:2307395 3-, mRNA sequence (GenBank: AI672553), and zk89g09.s1 Soares pregnant uterus NbHPU *Homo sapiens* cDNA clone IMAGE:490048 3- similar to contains element PTRS repetitive element, mRNA sequence (GenBank: AA121544); or (vi) insulin-like growth factor 2 (somatomedin A) /// INS-IGF2 readthrough transcript (IGF2 /// INS-IGF2), FBJ murine osteosarcoma viral oncogene homolog B (FOSB), alkaline phosphatase, placental (ALPP), mesothelin, (MSLN), carboxypeptidase A3 (mast cell) (CPA3), prokineticin 1; (PROK1, Genbank: AW183087), phosphatase and actin regulator 2 (PHACTR2);

or (vii) Janus kinase 1 (JAK1)), PHD finger protein 21A (PHF21A)), catenin (cadherin-associated protein), beta 1, 88 kDa (CTNNB1)), chromobox homolog 3; Genbank: NM 016587 (CBX3)), solute carrier family 39 (zinc transporter), member 6 (SLC39A6)), ceruloplasmin (ferroxidase) (CP), leucine zipper protein 1 (LUZP1), ADAM metallopeptidase with thrombospondin type 1 motif, 5 (ADAMTS5), CAP-GLY domain containing linker protein 1 (CLIP1), SOCS2 antisense RNA 1 (non-protein coding) (SOCS2-AS1)), calcium channel, voltage-dependent, beta 2 subunit (CACNB2)), nicotinamide riboside kinase 1 (NMRK1)), retinoic acid receptor, alpha (RARA)), metastasis associated in colon cancer 1 (MACC1)), ARP2 actin-related protein 2 homolog (yeast) (ACTR2)), arginine-glutamic acid dipeptide (RE) repeats (RERE)), jun B proto-oncogene (JUNB)), early growth response 1 (EGR1)), transducin (beta)-like 1X-linked (TBL1X)), plakophilin 4 (PKP4)), myxovirus (influenza virus) resistance 1, interferon-inducible protein p78 (mouse) (MX1)), tumor-associated calcium signal transducer 2 (TACSTD2)), serpin peptidase inhibitor, Glade E (nexin, plasminogen activator inhibitor type 1), member 1 (SERPINE1)), ephrin-B2 (EFNB2)), FBJ murine osteosarcoma viral oncogene homolog B (FOSB)), matrix metallopeptidase 14 (membrane-inserted) (MMP14)), PR domain containing 2, with ZNF domain (PRDM2)), pleckstrin and Sec7 domain containing 3 (PSD3)), deiodinase, iodothyronine, type II (DI02)), aquaporin 3 (Gill blood group) (AQP3)), solute carrier family 4, sodium bicarbonate cotransporter, member 4 (SLC4A4)), hemoglobin, alpha 1 /// hemoglobin, alpha 2 (HBA1 /// HBA2)), POM121 and ZP3 fusion /// zona pellucida glycoprotein 3 (sperm receptor); Genbank: NM 012230 (POMZP3 /// ZP3)), early endosome antigen 1 (EEA1)), mesothelin (MSLN)), LY6/PLAUR domain containing 3 (LYPD3)), fibrinogen beta chain (FGB)), ectonucleotide pyrophosphatase/phosphodiesterase 1 (ENPP1)), C-type lectin domain family 3, member B /// exosome component 7 (CLEC3B /// EXOSC7)), insulin-like growth factor binding protein 1 (IGFBP1)), kallikrein-related peptidase 11 (KLK11)), phosphatidylinositol-4-phosphate 5-kinase, type I, beta (PIP5K1B)), matrix metallopeptidase 10 (stromelysin 2) (MMP10)), G protein-coupled receptor 64 (GPR64)), left-right determination factor 2 (LEFTY2)), cystatin SN (CST1)), serine peptidase inhibitor, Kazal type 1 (SPINK1)), prolactin receptor (PRLR)), epiphycan (EPYC)), cytochrome P450, family 24, subfamily A, polypeptide 1), (CYP24A1) transient receptor potential cation channel, subfamily C, member 6 (TRPC6)), suppressor of glucose, autophagy associated 1 (SOGA1)), cysteine-rich secretory protein 3 (CRISP3)), cell division cycle 42 (GTP binding protein, 25 kDa) (CDC1$_4$2)), cell adhesion molecule 1 (CADM1)), hemoglobin, beta (HBB)), FBJ murine osteosarcoma viral oncogene homolog (FOS)), chitinase 3-like 1 (cartilage glycoprotein-39) (CHI3L1)), 4-aminobutyrate aminotransferase (ABAT)), cathepsin Z (CTSZ)), uroplakin 1B (UPK1B)), POM121 and ZP3 fusion; Genbank: BC000487 (POMZP3)), interleukin 6 signal transducer (gp130, oncostatin M receptor) (IL6ST)), neurofibromin 1 (NF1)), DEAH (Asp-Glu-Ala-His) box polypeptide 9 (DHX9)), eukaryotic translation initiation factor 1 (EIF1)), SECIS binding protein 2-like (SECISBP2L)), microfibrillar-associated protein 4 (MFAP4)), son of sevenless homolog 1 (*Drosophila*) (SOS1)), microfibrillar associated protein 5 (MFAP5)), leucine rich repeat containing 15 (LRRC15)), somatostatin (SST)), inhibitor of DNA binding 2, dominant negative helix-loop-helix protein /// inhibitor of DNA binding 2B, dominant negative helix-loop-helix protein (pseudogene) (ID2 /// ID2B)), C-terminal binding protein 1 (CTBP1)), cytochrome P450, family 2, subfamily C, polypeptide 9 (CYP2C9)), heat shock 70 kDa protein 12A (HSPA12A)), TWIST neighbor (TWISTNB)), glucuronidase, beta pseudogene 3 ///glucuronidase, beta pseudogene 9 /// glucuronidase, beta pseudogene /// glucuronidase, beta pseudogene (GUSBP3 /// GUSBP9 /// SMA4 /// SMAS)), dual-specificity tyrosine-(Y)-phosphorylation regulated kinase 1B (DYRK1B)), ATPase type 13A3 (ATP13A3)), Chondrolectin (CHODL)), aldehyde dehydrogenase 8 family, member A1 (ALDH8A1)), transforming growth factor, beta 2 (TGFB2)), SET domain containing 2 (SETD2), UDP-glucose ceramide glucosyltransferase (UGCG), abhydrolase domain containing 2 (ABHD2), vacuolar protein sorting 35 homolog (*S. cerevisiae*) (VPS35), zinc finger, CCHC domain containing 2 (ZCCHC2), testis expressed 101 (TEX101), nucleoporin like 1 (NUPL1), angiopoietin-like 1 (ANGPTL1), uncharacterized LOC100507645 /// metastasis associated lung adenocarcinoma transcript 1 (non-protein coding) (LOC100507645 /// MALAT1), WAS protein family, member 2 (WASF2), cytoplasmic polyadenylation element binding protein 4 (CPEB4), SLAIN motif family, member 2 (SLAIN2), BTB (POZ) domain containing 7 (BTBD7), EGF-like repeats and discoidin I-like domains 3 (EDIL3), F-box protein 32 (FBXO32), cut-like homeobox 1 (CUX1), integrin, beta 6 (ITGB6), zinc finger protein 800 (ZNF800), chromosome 12 open reading frame 35 (C12orf35), heparan sulfate (glucosamine) 3-O-sulfotransferase 3B1 (HS3ST3B1), uncharacterized LOC100653132 (LOC100653132), metastasis associated lung adenocarcinoma transcript 1 (non-protein coding) (MALAT1), sortilin-related VPS10 domain containing receptor 1 (SORCS1), calpain 8 (CAPN8), Indian hedgehog (IHH), DEAD (Asp-Glu-Ala-Asp) box helicase 17 (DDX17), fer (fps/fes related) tyrosine kinase (FER), U2 small nuclear RNA auxiliary factor 1 (U2AF1), uncharacterized LOC100287497 /// uncharacterized LOC100287934 (LOC100287497 /// LOC100287934), biorientation of chromosomes in cell division 1-like 1 (BOD1L1), RAB12, member RAS oncogene family (RAB12), UDP-N-acetyl-alpha-D-galactosamine:polypeptide N-acetylgalactosaminyltransferase-like 2 (GALNTL2), uncharacterized LOC100505989 (LOC100505989), uncharacterized LOC100506582 (LOC100506582), CDC-like kinase 4 (CLK4), HECT domain containing E3 ubiquitin protein ligase 1 (HECTD1), Zinc finger protein 24 (ZNF24), phosphorylase kinase, beta (PHKB), Nipped-B homolog (*Drosophila*) (NIPBL), transmembrane emp24 protein transport domain containing 8 (TMED8), and phosphatase and actin regulator 2 (PHACTR2); or (viii) CDCl$_4$2 small effector 2; Genbank: NM 020240 (CDCl$_4$2SE2), chromodomain protein, Y-like 2 (CDYL2), Williams Beuren syndrome chromosome region 27 (WBSCR27), carboxyl ester lipase (bile salt-stimulated lipase) (CEL), 5'-nucleotidase, ecto (CD73) (NTSE), chromosome 1 open reading frame 210 (C1orf210), zinc finger, BED-type containing 1 (ZBED1), cytochrome P450, family 4, subfamily B, polypeptide 1 (CYP4B1), long intergenic non-protein coding RNA 476 (LINC00476), ceruloplasmin (ferroxidase) (CP), uncharacterized LOC201477 (LOC201477), solute carrier family 8 (sodium/calcium exchanger), member 1 (SLC8A1), synaptotagmin-like 3 (SYTL3), defensin, beta 124 (DEFB124), serpin peptidase inhibitor, Glade E (nexin, plasminogen activator inhibitor type 1), member 1 (SERPINE1), dapper, antagonist of beta-catenin, homolog 2 (*Xenopus laevis*) (DACT2), BCL2-associated transcription factor 1 (BCLAF1), ATPase, Na+/K+transporting, beta 1 polypeptide (ATP1B1), lactotransferrin (LTF), copine III (CPNE3), inositol 1,4,5-trisphosphate receptor, type 2 (ITPR2), S100 calcium binding protein A8 (S100A8), stathmin-like 2 (STMN2), myosin VI (MYO6), ataxin 1 (ATXN1), major histocompatibility complex, class II, DQ alpha 1 (HLA-DQA1), coagulation factor XIII, A1 polypeptide (F13A1), amiloride binding protein 1 (amine oxidase (copper-containing)) (ABP1), fibroblast growth factor receptor 2 (FGFR2), phospholipase A2, group IIA (platelets, synovial fluid) (PLA2G2A), heme oxygenase (decycling) 1 (HMOX1), protein kinase, cAMP-dependent, regulatory, type II, beta (PRKAR2B), prenylcysteine oxidase 1 (PCYOX1), propionyl CoA carboxylase, alpha polypeptide (PCCA), vascular cell adhesion molecule 1 (VCAM1), histamine N-methyltransferase (HNMT), POM121 and ZP3 fusion ///zona pellucida glycoprotein 3 (sperm receptor) (POMZP3 /// ZP3), S100 calcium binding protein A2 (S100A2), fibroblast growth factor receptor 3 (FGFR3), kynureninase (KYNU), acid phosphatase, prostate (ACPP), matrix metallopeptidase 1 (interstitial collagenase) (MMP1), mal, T-cell differentiation protein (MAL), orosomucoid 1; Genbank: NM_000607 (ORM1), orosomucoid 1 /// orosomucoid 2; Genbank: NM_000607 /// NM 000608. (ORM1 /// ORM2), cystic fibrosis transmembrane conductance regulator (ATP-binding cassette sub-family C, member 7) (CFTR), phosphoserine phosphatase (PSPH), solute carrier family 26 (sulfate transporter), member 2 (SLC26A2), chemokine (C—X-C motif) ligand 13 (CXCL13), thymosin beta 15a/// thymosin beta 15B (TMSB15A /// TMSB15B), macrophage stimulating 1 receptor (c-met-related tyrosine kinase) (MST1R), protein phosphatase 1, regulatory (inhibitor) subunit 1A (PPP1R1A), proprotein convertase subtilisin/kexin type 5 (PCSK5), RAS guanyl releasing protein 1 (calcium and DAG-regulated) (RASGRP1), matrix metallopeptidase 10 (stromelysin 2) (MMP10), BCL2-related protein A1 (BCL2A1), actin binding LIM protein family, member 3 (ABLIM3), cytochrome P450, family 3, subfamily A, polypeptide 5 (CYP3A5), left-right determination factor 2 (LEFTY2), cystatin SN (CST1), serine peptidase inhibitor, Kazal type 1 (SPINK1), gastrin-releasing peptide (GRP), solute carrier family 1 (neuronal/epithelial high affinity glutamate transporter, system Xag), member 1 (SLC1A1), cadherin 16, KSP-cadherin (CDH16), G antigen 12B /// G antigen 12C /// G antigen 12D /// G antigen 12E /// G antigen 12F /// G antigen 12G /// G antigen 12H /// G antigen 121 /// G antigen 2A /// G antigen 2B /// G antigen 2C /// G antigen 4/// G antigen 5/// G antigen 6/// G antigen 7(GAGE12B ///GAGE12C /// GAGE12D /// GAGE12E /// GAGE12F /// GAGE12G /// GAGE-12H /// GAGE12I /// GAGE2A /// GAGE2B /// GAGE2C /// GAGE4 /// GAGES /// GAGE6 /// GAGE7), homeobox C6 (HOXC6), nuclear factor I/C (CCAAT-binding transcription factor) (NFIC), gamma-aminobutyric acid (GABA) A receptor, alpha 2 (GABRA2), colony stimulating factor 2 receptor, alpha, low-affinity (granulocyte-macrophage) (CSF2RA), G antigen 1 /// G antigen 12B /// G antigen 12C /// G antigen 12D /// G antigen 12E /// G antigen 12F /// G antigen 12 G /// G antigen 12H /// G antigen 121 /// G antigen 12J /// G antigen 2A /// G antigen 2B /// G antigen 2C /// G antigen 2D /// G antigen 2E /// G antigen 4 /// G antigen 5 /// G antigen 6 /// G antigen 7 ///G antigen 8 (GAGE1 /// GAGE12B /// GAGE12C /// GAGE12D /// GAGE12E /// GAGE12F ///GAGE12G /// GAGE12H /// GAGE12I /// GAGE12J /// GAGE2A /// GAGE2B /// GAGE2C ///GAGE2D /// GAGE2E /// GAGE4 /// GAGES /// GAGE6 /// GAGE7 /// GAGE8), family with sequence similarity 107, member A /// uncharacterized LOC100506924 (FAM107A ///LOC100506924), G antigen 3 (GAGE3), G antigen 1 /// G antigen 12C /// G antigen 12D /// G antigen 12E /// G antigen 12F /// G antigen 12G /// G antigen 12H /// G antigen 12I /// G antigen 12J /// G antigen 2A /// G antigen 2B /// G antigen 2C /// G antigen 2D /// G antigen 2E /// G antigen 3 /// G antigen 4 /// G antigen 5 /// G antigen 6 /// G antigen 7 /// G antigen 8 (GAGE1 ///GAGE12C /// GAGE12D /// GAGE12E /// GAGE12F /// GAGE12G /// GAGE12H /// GAGE12I /// GAGE12J /// GAGE2A /// GAGE2B /// GAGE2C /// GAGE2D /// GAGE2E /// GAGE3 ///GAGE4 ///GAGE5 /// GAGE6 /// GAGE7 /// GAGE8), gastrin (GAST), G antigen 1 /// G antigen 12C /// G antigen 12D /// G antigen 12E /// G antigen 12F /// G antigen 12G /// G antigen 12H /// G antigen 12I /// G antigen 12J /// G antigen 2D /// G antigen 4 /// G antigen 5 /// G antigen 6 /// G antigen 7 (GAGE1 /// GAGE12C /// GAGE12D /// GAGE12E /// GAGE12F ///GAGE12G /// GAGE12H /// GAGE12I /// GAGE12J /// GAGE2D /// GAGE4 /// GAGE5 ///GAGE6 ///GAGE7), G antigen 12F /// G antigen 12G /// G antigen 12I /// G antigen 4 /// G antigen 5 /// G antigen 6 /// G antigen 7 (GAGE12F /// GAGE12G /// GAGE12I /// GAGE4 ///GAGE5 /// GAGE6 /// GAGE7), deleted in malignant brain tumors 1 (DMBT1), wingless-type MMTV integration site family, member 4 (WNT4), topoisomerase (DNA) I (TOP1), hemoglobin, beta (HBB), nuclear receptor subfamily 2, group F, member 2 (NR2F2), kelch domain containing 10 (KLHDC10), laminin, beta 3 (LAMB3), major histocompatibility complex, class II, DQ beta 1 (HLA-DQB1), paraneoplastic Ma antigen 2 (PNMA2), alcohol dehydrogenase 1B (class I), beta polypeptide (ADH1B), major histocompatibility complex, class II, DR beta 4 /// HLA class II histocompatibility antigen, DR beta 4 chain-like (HLA-DRB4 ///LOC100509582), cysteine-rich secretory protein 2 (CRISP2), Metallothionein 1G (MT1G), RAR-related orphan receptor A (RORA), cysteine-rich, angiogenic inducer, 61 (CYR61), POM121 and ZP3 fusion (POMZP3), leptin receptor (LEPR), killer cell immunoglobulin-like receptor, three domains, long cytoplasmic tail, 1 (KIR3DL1), chemokine (C—X-C motif) receptor 4 (CXCR4), proline-rich coiled-coil 2C (PRRC2C), insulin-like growth factor binding protein 3 (IGFBP3), sulfatase 1 (SULF1), microfibrillar-associated protein 4 (MFAP4), olfactomedin 4 (OLFM4), immunoglobulin heavy constant mu (IGHM), Apolipoprotein E (APOE), major histocompatibility complex, class II, DQ beta 1 /// HLA class II histocompatibility antigen, DQ beta 1 chain-like (HLA-DQB1 /// LOC100293977), latent transforming growth factor beta binding protein 4 (LTBP4), mucin 5B, oligomeric mucus/gel-forming (MUC5B), complement factor H (CFH), major histocompatibility complex, class II, DQ alpha 1 /// HLA class II histocompatibility antigen, DQ alpha 1 chain-like /// HLA class II histocompatibility antigen, DQ alpha 1 chain-like (HLA-DQA1 /// LOC100507718 /// LOC100509457), Eukaryotic translation elongation factor 1 epsilon 1 (EEF1E1), CCCTC-binding factor (zinc finger protein) (CTCF), cytochrome P450, family 2, subfamily C, polypeptide 9 (CYP2C9), ADAM metallopeptidase with thrombospondin type 1 motif, 2 (ADAMTS2), CDCl$_4$2 binding protein kinase alpha (DMPK-like) (CDCl$_4$2BPA), complement factor H /// complement factor H-related 1 (CFH ///CFHR1), dapper, antagonist of beta-catenin, homolog 1 (*Xenopus laevis*) (DACT1), family with sequence similarity 118, member A (FAM118A), hippocalcin like 4 (HPCAL4), DDB1 and CUL4 associated factor 16 (DCAF16), beta-carotene 15,15'-monooxygenase 1 (BCMO1), SAM pointed domain containing ets transcription factor (SPDEF), catsper channel auxiliary subunit beta (CATSPERB), leucine rich repeat containing 31 (LRRC31), ST6 (alpha-N-acetyl-neuraminyl-2,3-beta-galactosyl-1,3)-N-acetyl-galactosaminide alpha-2,6-sialyltransferase 5 (ST6GALNAC5), collectin sub-family member 12 (COLEC12), major histocompatibility complex, class II, DR beta 1 /// major histocompatibility complex, class II, DR beta 3 /// major histocompatibility complex, class II, DR beta 4 /// major histocompatibility complex, class II, DR beta 5 /// HLA class II histocompatibility antigen, DRB1-7 beta chain-like /// HLA class II histocompatibility antigen, DRB1-7 beta chain-like /// HLA class II histocompatibility antigen, DR beta 4 chain-like (HLA-DRB1 /// HLA-DRB3 /// HLA-DRB4 /// HLA-DRB5 ///LOC100507709 ///LOC100507714 /// LOC100509582), uncharacterized LOC100653010 (LOC100653010), growth differentiation factor 15 (GDF15), suppressor of IKBKE 1 (SIKE1), TRK-fused gene (TFG), phosphotriesterase related (PTER), collagen, type IV, alpha 3 (Goodpasture antigen) binding protein (COL4A3BP), cripto, FRL-1, cryptic family 1 /// cripto, FRL-1, cryptic family 1B (CFC1 /// CFC1B), solute carrier family 46, member 2 (SLC46A2), membrane-spanning 4-domains, subfamily A, member 8B (MS4A8B), H19, imprinted maternally expressed transcript (non-protein coding) /// microRNA 675 (H19 /// MIR675), leukemia inhibitory factor receptor alpha (LIFR), collagen, type XII, alpha 1 (COL12A1), BPI fold containing family B, member 1 (BPIFB1), delta/notch-like EGF repeat containing (DNER), multiple EGF-like-domains 6 (MEGF6), coiled-coil domain containing 146 (CCDC146), TAO kinase 1 (TAOK1), endoplasmic reticulum aminopeptidase 2 (ERAP2), uncharacterized LOC100505806 (LOC100505806), napsin B aspartic peptidase pseudogene (NAPSB), zymogen granule protein 16 homolog B (rat) (ZG16B), immunoglobulin superfamily, member 11 (IGSF11), nuclear transcription factor Y, alpha (NFYA), uncharacterized LOC100506029 ///uncharacterized LOC100506051 (LOC100506029 /// LOC100506051), thyroid hormone receptor, beta (THRB), cystin 1 (CYS1), multiple C2 domains, transmembrane 2 (MCTP2), neuronal PAS domain protein 3 (NPAS3), chromosome 20 open reading frame 85 (C20orf85), family with sequence similarity 69, member C (FAM69C), scavenger receptor class A, member 5 (putative) (SCARA5), fibronectin type III domain containing 3B (FNDC3B), peptidase inhibitor 15 (PI15), secretoglobin, family 3A, member 1 (SCGB3A 1), Kruppel-like factor 9 (KLF9), guanylate binding protein 1, interferon-inducible (GBP1), mitochondrial antiviral signaling protein (MAVS), ankyrin repeat domain 33B (ANKRD33B), small nucleolar RNA, C/D box 3B-1 /// small nucleolar RNA, C/D box 3B-2 /// small nucleolar RNA, C/D box 3D (SNORD3B-1 /// SNORD3B-2 /// SNORD3D), family with sequence similarity 178, member A (FAM178A), THAP domain containing 6 (THAP6), uncharacterized LOC100422737 (LOC100422737), scavenger receptor class A, member 5 (putative) (SCARA5), Suppressor of zeste 12 homolog pseudogene (SUZ12P), BCL2-like 10 (apoptosis facilitator) (BCL2L10), ribosomal modification protein rimK-like family member B (RIMKLB), pleckstrin homology domain containing, family A (phosphoinositide binding specific) member 2 (PLEKHA2), eukaryotic translation initiation factor 4E family member 3 (EIF4E3), sphingosine-1-phosphate phosphatase 2 (SGPP2), RAB3A interacting protein (rabin3) (RAB3IP), docking protein 7 (DOK7), mindbomb E3 ubiquitin protein ligase 2 (MIB2), uncharacterized LOC100653229 (LOC100653229), integrin, beta 8 (ITGB8), WD repeat domain 38 (WDR38), and shisa homolog 8 (*Xenopus laevis*) (SHISA8); or (ix) heat shock 70 kDa protein 6 (HSP7OB'); Genbank: NM 002155, X51757 (HSPA6), thyroid hormone receptor, alpha (THRA), GTPase, IMAP family member 1 (GIMAP1), toll-interleukin 1 receptor (TIR) domain containing adaptor protein (TIRAP), activin A receptor, type IC (ACVR1C), interleukin 12 receptor, beta 1 (IL12RB1), Janus kinase 1 (JAK1), RAD51L3-RFFL readthrough /// ring finger and FYVE-like domain containing E3 ubiquitin protein ligase (RAD51L3-RFFL /// RFFL), zinc finger protein 417 (ZNF417), SEC62 homolog (*S. cerevisiae*) (SEC62), sialic acid binding Ig-like lectin 10 (SIGLEC10), potassium voltage-gated channel, subfamily G, member 3 (KCNG3), CD300 molecule-like family member f (CD300LF), monoacylglycerol O-acyltransferase 1 (MOGAT1), solute carrier family 5 (sodium/myo-inositol cotransporter), member 3 (SLC5A3), forkhead box C1 (FOXC1), perforin 1 (pore forming protein) (PRF1), Williams Beuren syndrome chromosome region 27 (WBSCR27), arylsulfatase B (ARSB), coiled-coil domain containing 60 ($CCDCl_60$), coagulation factor C homolog, cochlin (Limulus *polyphemus*) (COCH), solute carrier family 25, member 48 (SLC25A48), CUGBP, Elav-like family member 2 (CELF2), dual oxidase maturation factor 1 (DUOXA1), methyltransferase like 8 (METTLE), transforming, acidic coiled-coil containing protein 1 (TACC1), TBC1 domain family, member 16 (TBC1D16), zinc finger, BED-type containing 1 (ZBED1), docking protein 5 (DOKS), Fc fragment of IgE, high affinity I, receptor for; gamma polypeptide (FCER1G), activating transcription factor 3 (ATF3), FCH domain only 2 (FCHO2), cyclin L1 (CCNL1), cytochrome P450, family 4, subfamily B, polypeptide 1 (CYP4B1), C-type lectin domain family 7, member A (CLEC7A), tribbles homolog 3 (*Drosophila*) (TRIB3), uncharacterized LOC284454 (LOC284454), calcium channel, voltage-dependent, L type, alpha 1D subunit (CACNA1D), DIAPH3 antisense RNA 1 (non-protein coding) (DIAPH3-AS1), uncharacterized LOC100506523 /// zinc finger protein 814 (LOC100506523 /// ZNF814), ribonuclease P RNA component H1 (RPPH1), serpin peptidase inhibitor, Glade B (ovalbumin), member 6 (SERPINB6), leptin receptor (LEPR), uncharacterized LOC100507250 (LOC100507250), uncharacterized LOC100506258 (LOC100506258), Acyl-CoA synthetase long-chain family member 4 (ACSL4), bridging integrator 3 (BIN3), polymerase I and transcript release factor (PTRF), zinc finger with KRAB and SCAN domains 1 (ZKSCAN1), zinc finger protein 587 /// zinc finger protein 587B (ZNF587 /// ZNF587B), microRNA 1204 /// Pvtl oncogene (non-protein coding) (MIR-1204 /// PVT1), zinc finger, DHHC-type containing 18 (ZDHHC18), sirtuin 2 (SIRT2), AHNAK nucleoprotein 2 (AHNAK2), chromosome 1 open reading frame 53 (Clorf53), uncharacterized LOC100507645 /// metastasis associated lung adenocarcinoma transcript 1 (non-protein coding) (LOC100507645 /// MALAT1), zinc finger protein 321, pseudogene /// zinc finger protein 816 /// ZNF816-ZNF321P readthrough (ZNF321P /// ZNF816 /// ZNF816-ZNF321P), calcium channel, voltage-dependent, beta 2 subunit (CACNB2), uncharacterized LOC642852 (LOC642852), F1138717 protein (F1138717), Sideroflexin 3 (SFXN3), uncharacterized LOC100506387 (LOC100506387), uncharacterized LOC201477 (LOC201477), solute carrier family 8 (sodium/calcium exchanger), member 1 (SLC8A1), uncharacterized LOC114796 (KIAA1908), Splicing factor 3B, 14 kDa subunit (SF3B14), olfactory receptor, family 7, subfamily D, member 2 (OR7D2), trinucleotide repeat containing 18 (TNRC18), LOC-100289561-PRKRIP1 readthrough (LOC100630923), activating transcription factor 1 (ATF1), IKAROS family zinc finger 1 (Ikaros) (IKZF1), pinin, desmosome associated protein (PNN), CD74 molecule, major histocompatibility complex, class II invariant chain (CD74), proteasomal ATPase-associated factor 1 (PAAF1), BRE antisense RNA 1 (non-protein coding) (BRE-AS1), long intergenic non-protein coding RNA 240 (LINC00240), ankyrin repeat domain 20 family, member A1 /// ankyrin repeat domain 20 family, member All, pseudogene /// ankyrin repeat domain 20 family, member A2 /// ankyrin repeat domain 20 family, member A3 /// ankyrin repeat domain 20 family, member A4 /// ankyrin repeat domain 20 family, member A5, pseudogene /// ankyrin repeat domain 20 family, member A9, pseudogene /// ankyrin repeat domain-containing protein 20B-like (ANKRD20A1 ///AN-KRD20A11P /// ANKRD20A2 /// ANKRD20A3 /// ANKRD20A4 /// ANKRD20A5P ///ANKRD20A9P /// LOC644339), catsper channel auxiliary subunit beta (CATSPERB), stearoyl-CoA desaturase (delta-9-desaturase) (SCD), 24-dehydrocholesterol reductase (DHCR24), dual specificity phosphatase 1 (DUSP1), cysteine-rich, angiogenic inducer, 61 (CYR61), neuronal regeneration related protein homolog (rat) (NREP), glutathione peroxidase 3 (plasma) (GPX3), myosin, heavy chain 11, smooth muscle (MYH11), zinc finger protein 36, C3H type, homolog (mouse) (ZFP36), insulin induced gene 1 (INSIG1), tenascin C (TNC), acyl-CoA synthetase long-chain family member 3 (ACSL3), nipsnap homolog 1 (*C. elegans*) (NIPSNAP1), endoglin (ENG), carboxypeptidase D (CPD), protein phosphatase 1, regulatory subunit 12B (PPP1R12B), lactotransferrin (LTF), dickkopf 3 homolog (*Xenopus laevis*) (DKK3), autocrine motility factor receptor, E3 ubiquitin protein ligase (AMFR), nuclear receptor subfamily 4, group A, member 1 (NR4A1), collagen, type I, alpha 2 (COL1A2), insulin-like growth factor 2 (somatomedin A) ///INS-IGF2 readthrough (IGF2 /// INS-IGF2), KIAA0101 (KIAA0101), dihydrofolate reductase (DHFR), nuclear receptor interacting protein 1 (NRIP1), intercellular adhesion molecule 1 (ICAM1), SERTA domain containing 2 (SERTAD2), glutathione peroxidase 2 (gastrointestinal) (GPX2), alanyl (membrane) aminopeptidase (ANPEP), adrenomedullin (ADM), SRY (sex determining region Y)-box 9 (SOX9), calpain 6 (CAPN6), stathmin-like 2 (STMN2), fumarate hydratase (FH), complement component 2 (C2), fibrillin 2 (FBN2), ST3 beta-galactoside alpha-2,3-sialyltransferase 5 (ST3GAL5), transducin-like enhancer of split 1 (E(spl) homolog, *Drosophila*) (TLE1), ataxin 1 (ATXN1), Fc fragment of IgG binding protein (FCGBP), cadherin 3, type 1, P-cadherin (placental) (CDH3), major histocompatibility complex, class II, DQ alpha 1 (HLA-DQA1), pleckstrin and Sec7 domain containing 3 (PSD3), epsin 2 (EPN2), S100 calcium binding protein A9 (S100A9), Kruppel-like factor 9 (KLF9), lysyl oxidase-like 1 (LOXL1), colony stimulating factor 3 receptor (granulocyte) (CSF3R), G protein-coupled receptor, family C, group 5, member B (GPRC5B), phospholipase A2, group IIA (platelets, synovial fluid) (PLA2G2A), B-cell CLL/lymphoma 2 (BCL2), peptidase inhibitor 3, skin-derived (PI3), phosphodiesterase 4B, cAMP-specific (PDE4B), myelin protein zero-like 2 (MPZL2), sema domain, immunoglobulin domain (Ig), short basic domain, secreted, (semaphorin) 3C (SEMA3C), polycomb group ring finger 2 (PCGF2), glutathione S-transferase theta 1 (GSTT1), tetraspanin 8 (TSPAN8), secretogranin V (7B2 protein) (SCGS), matrix metallopeptidase 9 (gelatinase B, 92 kDa gelatinase, 92 kDa type IV collagenase) (MMP9), hemoglobin, alpha 1 ///hemoglobin, alpha 2 (HBA1 /// HBA2), replication factor C (activator 1) 4, 37 kDa (RFC4), CTAGE family, member 5 (CTAGE5), ArfGAP with GTPase domain, ankyrin repeat and PH domain 1 (AGAP1), preferentially expressed antigen in melanoma (PRAME), interleukin 2 receptor, gamma (IL2RG), growth arrest and DNA-damage-inducible, gamma (GADD45G), glutathione S-transferase mu 4 (GSTM4), ectonucleotide pyrophosphatase/phosphodiesterase 4 (putative) (ENPP4), CD37 molecule (CD37), S100 calcium binding protein A2 (S100A2), v-ski sarcoma viral oncogene homolog (avian) (SKI), phenylalanyl-tRNA synthetase 2, mitochondrial (FARS2), prominin 1 (PROM1), adenylate kinase 4 /// adenylate kinase isoenzyme 4, mitochondrial-like (AK4 /// LOC100507855), solute carrier family 43, member 1 (SLC43A1), glutathione S-transferase mu 2 (muscle) (GSTM2), folate receptor 1 (adult) (FOLR1), interferon-induced protein 44-like (IFI44L), matrix metallopeptidase 1 (interstitial collagenase) (MMP1), cell division cycle 7 homolog (*S. cerevisiae*) (CDCl$_7$), thymocyte selection-associated high mobility group box (TOX), chemokine (C—X-C motif) ligand 10 (CXCL10), gamma-aminobutyric acid (GABA) A receptor, epsilon /// microRNA 224 /// microRNA 452 (GABRE ///MIR224 ///MIR452), glutathione S-transferase mu 1 (GSTM1), apolipoprotein C-II ///apolipoprotein C-IV /// APOC4-APOC2 readthrough (APOC2 /// APOC4 /// APOC4-APOC2), ATP-binding cassette, sub-family G (WHITE), member 1 (ABCG1), matrix metallopeptidase 12 (macrophage elastase) (MMP12), dickkopf 1 homolog (*Xenopus laevis*) (DKK1), serpin peptidase inhibitor, Glade B (ovalbumin), member 2 (SERPINB2), trefoil factor 3 (intestinal) (TFF3), steroid-5-alpha-reductase, alpha polypeptide 1 (3-oxo-5 alpha-steroid delta 4-dehydrogenase alpha 1) (SRD5A1), ATP-binding cassette, subfamily A (ABC1), member 8 (ABCA8), regulating synaptic membrane exocytosis 3 (RIMS3), dual specificity phosphatase 2 (DUSP2), creatine kinase, muscle (CKM), folate receptor 2 (fetal) (FOLR2), mutL homolog 3 (*E. coli*) (MLH3), glutamyl aminopeptidase (aminopeptidase A) (ENPEP), mesothelin (MSLN), LY6/PLAUR domain containing 3 (LYPD3), asparagine synthetase (glutamine-hydrolyzing) (ASNS), phosphoserine phosphatase (PSPH), aldehyde oxidase 1 (AOX1), solute carrier family 26 (sulfate transporter), member 2 (SLC26A2), chemokine (C-C motif) receptor 1 (CCR1), neurofilament, medium polypeptide (NEFM), chemokine (C-C motif) ligand 3 /// chemokine (C-C motif) ligand 3-like 1 /// chemokine (C-C motif) ligand 3-like 3 (CCL3 /// CCL3L1 ///CCL3L3), prostaglandin-endoperoxide synthase 1 (prostaglandin G/H synthase and cyclooxygenase) (PTGS1), actin, alpha, cardiac muscle 1 (ACTC1), integrin beta 3 binding protein (beta3-endonexin) (ITGB3BP), adaptor-related protein complex 1, sigma 1 subunit (ANSI), hydroxycarboxylic acid receptor 3 (HCAR3), superoxide dismutase 3, extracellular (SOD3), leukemia inhibitory factor (LIF), insulin-like growth factor binding protein 1 (IGFBP1), thymosin beta 15a /// thymosin beta 15B (TMSB15A /// TMSB15B), gamma-glutamyl carboxylase (GGCX), carbonyl reductase 3 (CBR3), protease, serine, 2 (trypsin 2) (PRSS2), solute carrier family 22 (extraneuronal monoamine transporter), member 3 (SLC22A3), glutathione S-transferase theta 2 (GSTT2), prolactin (PRL), macrophage stimulating 1 receptor (c-met-related tyrosine kinase) (MST1R), CD3e molecule, epsilon (CD3-TCR complex) (CD3E), kallikrein-related peptidase 11 (KLK11), granzyme A (granzyme 1, cytotoxic T-lymphocyte-associated serine esterase 3) (GZMA), granulysin (GNLY), advillin (AVIL), bactericidal/permeability-increasing protein (BPI), histamine receptor H1 (HRH1), nitric oxide synthase 3 (endothelial cell) (NOS3), olfactomedin 1 (OLFM1), complement component 4 binding protein, alpha (C4BPA), 2'-5'-oligoadenylate synthetase-like (OASL), tryptase alpha/beta 1 (TPSAB1), synaptogyrin 3 (SYNGR3), cerebellin 1 precursor (CBLN1), CD8a molecule (CD8A), cytochrome P450, family 3, subfamily A, polypeptide 5 (CYP3A5), WNT1 inducible signaling pathway protein 2 (WISP2), CD2 molecule (CD2), prostate androgen-regulated transcript 1 (non-protein coding) (PART1), solute carrier family 7 (orphan transporter), member 4 (SLC7A4), gamma-aminobutyric acid (GABA) B receptor, 1 /// ubiquitin D (GABBR1 /// UBD), solute carrier family 22 (organic cation/ergothioneine transporter), member 4 (SLC22A4), phospholipase C-like 1 (PLCL1), EPH receptor A1 (EPHA1), hyaluronan binding protein 2 (HABP2), left-right determination factor 2 (LEFTY2), tumor necrosis factor, alpha-induced protein 6 (TNFAIP6), acyl-CoA dehydrogenase, long chain (ACADL), protein tyrosine phosphatase, receptor type, R (PTPRR), leucine rich repeat containing 37, member A3 (LRRC37A3), matrilin 3 (MATN3), UDP glucuronosyltransferase 1 family, polypeptide A1 ///UDP glucuronosyltransferase 1 family, polypeptide A10 /// UDP glucuronosyltransferase 1 family, polypeptide A3 /// UDP glucuronosyltransferase 1 family, polypeptide A4 /// UDP glucuronosyltransferase 1 family, polypeptide A5 /// UDP glucuronosyltransferase 1 family, polypeptide A6 /// UDP glucuronosyltransferase 1 family, polypeptide A7 /// UDP glucuronosyltransferase 1 family, polypeptide A8 /// UDP glucuronosyltransferase 1 family, polypeptide A9 (UGT 1 A1 /// UGT 1 A10 /// UGT1A3 /// UGT1A4 /// UGT1A5 /// UGT-1A6 ///UGT1A7 ///UGT1A8 /// UGT1A9), kallikrein-related peptidase 8 (KLK8), cytochrome P450, family 4, subfamily F, polypeptide 11 (CYP4F11), Rho GTPase activating protein 6 (ARHGAP6), interleukin 13 receptor, alpha 2 (IL13RA2), cystatin SN (CST1), matrix metallopeptidase 17 (membrane-inserted)

(MMP17), Rho GTPase activating protein 22 (ARHGAP22), family with sequence similarity 155, member B (FAM155B), parathyroid hormone-like hormone (PTHLH), serine peptidase inhibitor, Kazal type 2 (acrosin-trypsin inhibitor) (SPINK2), gastrin-releasing peptide (GRP), chemokine (C—X-C motif) ligand 6 (granulocyte chemotactic protein 2) (CXCL6), cytochrome c oxidase subunit VIa polypeptide 2 (COX6A2), chemokine (C motif) ligand 1 (XCL1), secretoglobin, family 2A, member 2 (SCGB2A2), platelet factor 4 (PF4), beta-1,4-N-acetyl-galactosaminyl transferase 1 (B4GALNT1), sphingosine-1-phosphate receptor 4 (S1PR4), leukotriene C4 synthase (LTC4S), 4-aminobutyrate aminotransferase (ABAT), aldo-keto reductase family 1, member B10 (aldose reductase) (AKR1B10), lymphocyte antigen 96 (LY96), solute carrier family 16, member 5 (monocarboxylic acid transporter 6) (SLC16A5), zinc finger, MYM-type 5 (ZMYM5), glycoprotein 2 (zymogen granule membrane) (GP2), family with sequence similarity 65, member B (FAM65B), crystallin, beta B2 /// crystallin, beta B2 pseudogene 1 (CRYBB2 /// CRYBB2P1), WNT1 inducible signaling pathway protein 1 (WISP1), progestagen-associated endometrial protein (PAEP), interleukin 11 (IL11), bone gamma-carboxyglutamate (gla) protein /// PMF1-BGLAP readthrough (BGLAP /// PMF1-BGLAP), tumor necrosis factor (TNF), tryptase beta 2 (gene/pseudogene) (TPSB2), deiodinase, iodothyronine, type III (DIO3), arachidonate 12-lipoxygenase (ALOX12), CD300c molecule (CD300C), CD209 molecule (CD209), killer cell immunoglobulin-like receptor, three domains, long cytoplasmic tail, 1 /// killer cell immunoglobulin-like receptor, three domains, long cytoplasmic tail, 2 /// killer cell immunoglobulin-like receptor, three domains, long cytoplasmic tail, 2-like (KIR3DL1 ///KIR3DL2 ///LOC727787), killer cell immunoglobulin-like receptor, three domains, long cytoplasmic tail, 2 /// killer cell immunoglobulin-like receptor, three domains, long cytoplasmic tail, 2-like (KIR3DL2 /// LOC727787), defensin, beta 4A /// defensin, beta 4B (DEFB4A ///DEFB4B), ras-related C3 botulinum toxin substrate 2 (rho family, small GTP binding protein Rac2) (RAC2), granzyme M (lymphocyte met-ase 1) (GZMM), pirin (iron-binding nuclear protein) (PIR), bradykinin receptor B1 (BDKRB1), growth arrest and DNA-damage-inducible, beta (GADD45B), pregnancy specific beta-1-glycoprotein 9 (PSG9), G antigen 1 /// G antigen 12C /// G antigen 12D /// G antigen 12E /// G antigen 12F /// G antigen 12G /// G antigen 12H ///G antigen 12I /// G antigen 12J /// G antigen 2A /// G antigen 2B /// G antigen 2C /// G antigen 2D /// G antigen 2E /// G antigen 3 /// G antigen 4 /// G antigen 5 /// G antigen 6 /// G antigen 7 ///G antigen 8 (GAGE1 /// GAGE12C /// GAGE12D /// GAGE12E /// GAGE12F /// GAGE12G ///GAGE12H /// GAGE12I /// GAGE12J /// GAGE2A /// GAGE2B /// GAGE2C /// GAGE2D ///GAGE2E /// GAGE3 /// GAGE4 /// GAGE5 /// GAGE6 /// GAGE7 /// GAGE8), fibroblast growth factor receptor 1 (FGFR1), mucin 1, cell surface associated (MUC1), keratin 13 (KRT13), nuclear factor of activated T-cells 5, tonicity-responsive (NFAT5), long intergenic non-protein coding RNA 597 (LINC00597), killer cell immunoglobulin-like receptor, two domains, short cytoplasmic tail, 3 (KIR2DS3), prostaglandin I2 (prostacyclin) synthase (PTGIS), gastrin (GAST), killer cell immunoglobulin-like receptor, two domains, short cytoplasmic tail, 1 (KIR2DS1), killer cell immunoglobulin-like receptor, two domains, short cytoplasmic tail, 5 (KIR2DS5), deleted in malignant brain tumors 1 (DMBT1), tyrosine hydroxylase (TH), ankyrin 1, erythrocytic (ANK1), killer cell immunoglobulin-like receptor, two domains, long cytoplasmic tail, 2 /// killer cell immunoglobulin-like receptor, two domains, long cytoplasmic tail, 4 /// killer cell immunoglobulin-like receptor, two domains, long cytoplasmic tail, 5A /// killer cell immunoglobulin-like receptor, two domains, long cytoplasmic tail, 5B /// killer cell immunoglobulin-like receptor three domains long cytoplasmic tail 3 /// killer cell immunoglobulin-like receptor, three domains, short cytoplasmic tail, 1 /// killer cell immunoglobulin-like receptor 2DL4-like (KIR2DL2 /// KIR2DL4 /// KIR2DL5A /// KIR2DL5B /// KIR3DL3 /// KIR3DS1 /// LOC100287534), RAS p21 protein activator 4 /// RAS p21 protein activator 4B /// RAS p21 protein activator 4C, pseudogene /// uroplakin 3B-like (RASA4 ///RASA4B /// RASA4CP /// UPK3BL), wingless-type MMTV integration site family, member 4 (WNT4), adaptor-related protein complex 3, delta 1 subunit (AP3D1), lectin, galactoside-binding, soluble, 8 (LGALS8), UPF1 regulator of nonsense transcripts homolog (yeast) (UPF1), keratin 7 (KRT7), coronin, actin binding protein, 1A (CORO1A), ubinuclein 1 (UBN1), hemoglobin, beta (HBB), aldo-keto reductase family 1, member C3 (3-alpha hydroxysteroid dehydrogenase, type II) (AKR1C3), FBJ murine osteosarcoma viral oncogene homolog (FOS), tissue factor pathway inhibitor 2 (TFPI2), carbonic anhydrase II (CA2), alpha-2-glycoprotein 1, zinc-binding (AZGP1), regulator of G-protein signaling 16 (RGS16), mal, T-cell differentiation protein-like (MALL), SR-related CTD-associated factor 11 (SCAF11), delta-like 1 homolog (*Drosophila*) (DLK1), carboxylesterase 1 /// liver carboxylesterase 1-like (CES1 ///LOC100653057), major histocompatibility complex, class II, DR beta 4 /// HLA class II histocompatibility antigen, DR beta 4 chain-like (HLA-DRB4 /// LOC100509582), nuclear receptor subfamily 1, group D, member 2 (NR1D2), ribonucleotide reductase M2 (RRM2), chemokine (C—X-C motif) ligand 2 (CXCL2), caspase 6, apoptosis-related cysteine peptidase (CASP6), kallikrein-related peptidase 10 (KLK10), TCR gamma alternate reading frame protein (TARP), secreted phosphoprotein 1 (SPP1), troponin C type 1 (slow) (TNNC1), transforming growth factor, beta 2 (TGFB2), solute carrier family 7 (anionic amino acid transporter light chain, xc- system), member 11 (SLC7A11), CD247 molecule (CD247), Rho family GTPase 1 (RND1), mitogen-activated protein kinase 13 (MAPK13), uroplakin 1B (UPK1B), activity-regulated cytoskeleton-associated protein (ARC), cytochrome P450, family 4, subfamily B, polypeptide 1 (CYP4B1), phospholipase A2, group IVA (cytosolic, calcium-dependent) (PLA2G4A), granzyme B (granzyme 2, cytotoxic T-lymphocyte-associated serine esterase 1) (GZMB), iroquois homeobox 5 (IRX5), discs, large homolog 5 (*Drosophila*) (DLG5), cancer/testis antigen 1A /// cancer/testis antigen 1B (CTAG1A /// CTAG1B), chemokine (C-C motif) ligand 23 (CCL23), leukocyte-associated immunoglobulin-like receptor 1 (LAIR1), neurturin (NRTN), claudin 14 (CLDN14), solute carrier family 43, member 3 (SLC43A3), natural cytotoxicity triggering receptor 3 (NCR3), periostin, osteoblast specific factor (POSTN), killer cell immunoglobulin-like receptor, two domains, long cytoplasmic tail, 1 /// killer cell immunoglobulin-like receptor, two domains, long cytoplasmic tail, 2 /// killer cell immunoglobulin-like receptor, two domains, long cytoplasmic tail, 3 /// killer cell immunoglobulin-like receptor, two domains, long cytoplasmic tail, 4 /// killer cell immunoglobulin-like receptor, two domains, long cytoplasmic tail, 5A /// killer cell immunoglobulin-like receptor, two domains, long cytoplasmic tail, 5B /// killer cell immunoglobulin-like receptor three domains long cytoplasmic tail 3 /// killer cell immunoglobulin-like receptor, three domains, short cytoplasmic tail, 1 /// killer cell immunoglobulin-like receptor 2DL4-like /// killer cell immunoglobulin-like receptor 2DL2-like (KIR2DL1 /// KIR2DL2 /// KIR2DL3 /// KIR2DL4 /// KIR2DL5A /// KIR2DL5B /// KIR3DL3 ///KIR3DS1 /// LOC100287534 /// LOC100653050), adaptor-related protein complex 3, delta 1 subunit (AP3D1), major histocompatibility complex, class II, DR alpha (HLA-DRA), hepatocyte growth factor (hepapoietin A; scatter factor) (HGF), proline-serine-threonine phosphatase interacting protein 1 (PSTPIP1), killer cell immunoglobulin-like receptor, two domains, long cytoplasmic tail, 4 (KIR2DL4), killer cell immunoglobulin-like receptor, two domains, long cytoplasmic tail, 2 (KIR2DL2), mitogen-activated protein kinase 11 (MAPK11), killer cell immunoglobulin-like receptor, two domains, short cytoplasmic tail, 1 /// killer cell immunoglobulin-like receptor, two domains, short cytoplasmic tail, 2 /// killer cell immunoglobulin-like receptor, two domains, short cytoplasmic tail, 3 /// killer cell immunoglobulin-like receptor, two domains, short cytoplasmic tail, 4 /// killer cell immunoglobulin-like receptor, two domains, short cytoplasmic tail, 5 /// killer cell immunoglobulin-like receptor three domains long cytoplasmic tail 3 (KIR2DS1 /// KIR2DS2 ///KIR2DS3 ///KIR2DS4 /// KIR2DS5 /// KIR3DL3), carcinoembryonic antigen-related cell adhesion molecule 6 (non-specific cross reacting antigen) (CEACAM6), killer cell immunoglobulin-like receptor, three domains, long cytoplasmic tail, 1 (KIR3DL1), proteoglycan 2, bone marrow (natural killer cell activator, eosinophil granule major basic protein) (PRG2), collagen, type IV, alpha 2 (COL4A2), major histocompatibility complex, class II, DP alpha 1 (HLA-DPA1), WNK lysine deficient protein kinase 1 (WNK1), dystroglycan 1 (dystrophin-associated glycoprotein 1) (DAG1), formin binding protein 4 (FNBP4), phosphoinositide-3-kinase, regulatory subunit 1 (alpha) (PIK3R1), solute carrier family 7 (cationic amino acid transporter, y+system), member 1 (SLC7A1), cytoplasmic linker associated protein 2 (CLASP2), myosin ID (MYO1D), KH and NYN domain containing (KHNYN), septin 6 (SEP6), ceramide synthase 6 (CERS6), collagen, type V, alpha 1 (COL5A1), interleukin 1 receptor antagonist (IL1RN), RAS p21 protein activator 4 /// RAS p21 protein activator 4B ///RAS p21 protein activator 4C, pseudogene (RASA4 /// RASA4B /// RASA4CP), nuclear factor of activated T-cells, cytoplasmic, calcineurin-dependent 2 interacting protein (NFATC2IP), pleckstrin homology domain containing, family G (with RhoGef domain) member 3 (PLEKHG3), suppressor of var1, 3-like 1 (*S. cerevisiae*) (SUPV3L1), collagen, type VI, alpha 1 (COL6A1), bobby sox homolog (*Drosophila*) (BBX), GATA zinc finger domain containing 1 (GATAD1), chitinase 3-like 2 (CHI3L2), NIMA (never in mitosis gene a)-related kinase 3 (NEK3), T-cell lymphoma invasion and metastasis 1 (TIAM1), phospholipase C, beta 1 (phosphoinositide-specific) (PLCB1), keratin 4 (KRT4), zinc finger protein 248 (ZNF248), transcription factor 25 (basic helix-loop-helix) (TCF25), progestin and adipoQ receptor family member III (PAQR3), mucin 5B, oligomeric mucus/gel-forming (MUC5B), RUN and FYVE domain containing 3 (RUFY3), neuronal pentraxin II (NPTX2), transformer 2 alpha homolog (*Drosophila*) (TRA2A), enolase superfamily member 1 (ENOSF1), solute carrier family 1 (neuronal/epithelial high affinity glutamate transporter, system Xag), member 1 (SLC1A1), family with sequence similarity 69, member A (FAM69A), galactosidase, beta 1-like 2 (GLB1L2), kinase suppressor of ras 1 (KSR1), StAR-related lipid transfer (START) domain containing 5 (STARD5), calmin (calponin-like, transmembrane) (CLMN), thrombospondin, type I, domain containing 7A (THSD7A), paired box 8 (PAX8), RPGRIP1-like (RPGRIP1L), zeta-chain (TCR) associated protein kinase 70 kDa (ZAP70), chemokine (C-C motif) ligand 8 (CCL8), gelsolin (GSN), protein tyrosine phosphatase, receptor type, D (PTPRD), methyl-CpG binding domain protein 4 (MBD4), CD7 molecule (CD7), myosin VIIA and Rab interacting protein (MYRIP), GNAS complex locus (GNAS), ATP-binding cassette, sub-family B (MDR/TAP), member 9 (ABCB9), galanin prepropeptide (GAL), dickkopf 3 homolog (*Xenopus laevis*) (DKK3), ribosomal protein L17 /// RPL17-C18orf32 readthrough (RPL17 /// RPL17-C18ORF32), mucin 5AC, oligomeric mucus/gel-forming (MUC5AC), nephroblastoma overexpressed (NOV), jun D proto-oncogene (JUND), RAS guanyl releasing protein 2 (calcium and DAG-regulated) (RASGRP2), heat shock 70 kDa protein 12A (HSPA12A), cathepsin W (CTSW), $CDCl_2$2 binding protein kinase alpha (DMPK-like) ($CDCl_4$2BPA), killer cell lectin-like receptor subfamily B, member 1 (KLRB1), ADAM metallopeptidase with thrombospondin type 1 motif, 2 (ADAMTS2), CD7 molecule (CD7), leukocyte immunoglobulin-like receptor pseudogene 2 (LILRP2), chemokine (C motif) ligand 1 /// chemokine (C motif) ligand 2 (XCL1 ///XCL2), motor neuron and pancreas homeobox 1 (MNX1), septin 10 (SEP10), adducin 1 (alpha) (ADD1), heat shock protein, alpha-crystallin-related, B6 (HSPB6), NEDD4 binding protein 3 (N4BP3), multiple EGF-like-domains 8 (MEGF8), cortactin (CTTN), SP140 nuclear body protein-like (SP140L), ATPase, Ca++transporting, type 2C, member 2 (ATP2C2), docking protein 5 (DOK5), glucuronidase, beta pseudogene (LOC100170939), chemokine (C—X-C motif) ligand 5 (CXCL5), transmembrane 4 L six family member 1 (TM4SF1), ring finger and CCCH-type domains 1 (RC3H1), solute carrier family 35, member E2 (SLC35E2), keratin 86 ///uncharacterized LOC100509764 (KRT86 /// LOC100509764), protease, serine, 3 pseudogene 2 (PRSS3P2), major histocompatibility complex, class II, DQ beta 2 (HLA-DQB2), cancer/testis antigen 2 (CTAG2), dual oxidase 1 (DUOX1), TCR gamma alternate reading frame protein /// T cell receptor gamma constant 2 (TARP /// TRGC2), prostaglandin D2 receptor (DP) (PTGDR), gamma-aminobutyric acid (GABA) A receptor, alpha 2 (GABRA2), T cell receptor delta variable 3 (TRDV3), sphingomyelin phosphodiesterase 1, acid lysosomal (SMPD1), Fas (TNF receptor superfamily, member 6) (FAS), uncharacterized LOC100288594

(LOC100288594), tryptase alpha/beta 1 /// tryptase beta 2 (gene/pseudogene) (TPSAB1 /// TPSB2), chemokine (C-C motif) ligand 2 (CCL2), killer cell immunoglobulin-like receptor, three domains, long cytoplasmic tail, 3 (KIR3DL3), family with sequence similarity 48, member A (FAM48A), regulator of G-protein signaling 1 (RGS1), YME1-like 1 (*S. cerevisiae*) (YME1L1), chromosome 14 open reading frame 1 (C14orf1), Uncharacterized LOC100287387 (LOC100287387), collagen, type VII, alpha 1 (COL7A1), kallikrein-related peptidase 13 (KLK13), uncharacterized LOC283683 /// programmed cell death 6 interacting protein pseudogene (LOC283683 /// LOC646278), histidine ammonia-lyase (HAL), small G protein signaling modulator 2 (SGSM2), tripartite motif containing 44 (TRIM44), ribonuclease T2 (RNASET2), chemokine (C—X-C motif) ligand 14 (CXCL14), nucleolar and spindle associated protein 1 (NUSAP1), claudin 1 (CLDN1), melanophilin (MLPH), complement component 1, q subcomponent, A chain (C1QA), tRNA-yW synthesizing protein 1 homolog (*S. cerevisiae*) ///tRNA-yW synthesizing protein 1 homolog B (*S. cerevisiae*) (TYW1 /// TYW1B), sorting nexin 10 (SNX10), GC-rich sequence DNA-binding factor 1 (GCFC1), LIM domain containing 2 (LIMD2), UPF3 regulator of nonsense transcripts homolog B (yeast) (UPF3B), acid phosphatase 6, lysophosphatidic (ACP6), collagen, type V, alpha 3 (COL5A3), small proline-rich protein 3 (SPRR3), asporin (ASPN), dapper, antagonist of beta-catenin, homolog 1 (*Xenopus laevis*) (DACT1), heat shock 70 kDa protein 14 (HSPA14), zinc finger protein 331 (ZNF331), enoyl CoA hydratase domain containing 3 (ECHDC3), intraflagellar transport 81 homolog (*Chlamydomonas*) (IFT81), Na+/K+transporting ATPase interacting 1 (NKAIN1), RAB3A interacting protein (rabin3)-like 1 (RAB3IL1), zinc finger family member 767 (ZNF767), zinc finger protein 606 (ZNF606), ATPase, aminophospholipid transporter, class I, type 8A, member 2 (ATP8A2), RAS protein activator like 1 (GAP1 like) (RASAL1), endoplasmic reticulum aminopeptidase 2 (ERAP2), DENN/MADD domain containing 1A (DENND1A), frizzled family receptor 10 (FZD10), poliovirus receptor related immunoglobulin domain containing (PVRIG), fukutin related protein (FKRP), chromosome 1 open reading frame 116 (C1orf116), chondrolectin (CHODL), frequently rearranged in advanced T-cell lymphomas (FRAT1), MAGI family member, X-linked (MAGIX), amyloid beta (A4) precursor protein-binding, family B, member 1 interacting protein (APBB11P), zinc finger protein 750 (ZNF750), epoxide hydrolase 3 (EPHX3), signal transducing adaptor family member 1 (STAP1), centrosome and spindle pole associated protein 1 (CSPP1), FXYD domain containing ion transport regulator 7 (FXYD7), aldehyde dehydrogenase 8 family, member A1 (ALDH8A1), family with sequence similarity 86, member C1 (FAM86C1), G protein-coupled receptor 97 (GPR97), ubiquitin associated and SH3 domain containing A (UBASH3A), chromodomain helicase DNA binding protein 9 (CHD9), ubiquitin interaction motif containing 1 (UIMC1), WD repeat domain 19 (WDR19), ST6 (alpha-N-acetyl-neuraminyl-2,3-beta-galactosyl-1,3)-N-acetylgalactosaminide alpha-2,6-sialyltransferase 5 (ST6GALNAC5), carbohydrate (N-acetylgalactosamine 4-0) sulfotransferase 8 (CHST8), DENN/MADD domain containing 1C (DENND1C), otoraplin (OTOR), BTB and CNC homology 1, basic leucine zipper transcription factor 2 (BACH2), Yip1 domain family, member 5 (YIPF5), transducin (beta)-like 1 X-linked receptor 1 (TBL1XR1), UDP-Gal:betaGlcNAc beta 1,4- galactosyltransferase, polypeptide 5 (B4GALT5), major histocompatibility complex, class II, DR beta 1 /// major histocompatibility complex, class II, DR beta 3 /// major histocompatibility complex, class II, DR beta 4 /// major histocompatibility complex, class II, DR beta 5 /// HLA class II histocompatibility antigen, DRB1-7 beta chain-like /// HLA class II histocompatibility antigen, DRB1-7 beta chain-like /// HLA class II histocompatibility antigen, DR beta 4 chain-like (HLA-DRB1 /// HLA-DRB3 /// HLA-DRB4 ///HLA-DRBS /// LOC100507709 /// LOC100507714 /// LOC100509582), par-3 partitioning defective 3 homolog (*C. elegans*) (PARD3), basic helix-loop-helix family, member e41 (BHLHE41), growth differentiation factor 15 (GDF15), zinc finger protein 83 (ZNF83), agmatine ureohydrolase (agmatinase) (AGMAT), NLR family, pyrin domain containing 2 (NLRP2), phosphoinositide-3-kinase interacting protein 1 (PIK3IP1), UDP-glucose ceramide glucosyltransferase (UGCG), angel homolog 2 (*Drosophila*) (ANGEL2), heterogeneous nuclear ribonucleoprotein A1 (HNRNPA1), uncharacterized LOC645644 (FLJ42627), solute carrier organic anion transporter family, member 4C1 (SLCO4C1), family with sequence similarity 63, member B (FAM63B), desumoylating isopeptidase 2 (DESI2), eosinophil granule ontogeny transcript (non-protein coding) (EGOT), chromosome 4 open reading frame 34 (C4orf34), tubulin, beta pseudogene 5 (TUBBPS), Programmed cell death 6 (PDCD6), adaptor protein, phosphotyrosine interaction, PH domain and leucine zipper containing 1 (APPL1), calcineurin-like phosphoesterase domain containing 1 (CPPED1), sterile alpha motif and leucine zipper containing kinase AZK (ZAK), mannosidase, endo-alpha (MANEA), ankylosis, progressive homolog (mouse) (ANKH), tripartite motif containing 8 (TRIMS), cingulin (CGN), gap junction protein, beta 2, 26 kDa (GJB2), membrane-spanning 4-domains, subfamily A, member 7 (MS4A7), chromosome 21 open reading frame 56 (C2lorf56), guanylate binding protein 3 (GBP3), cysteine-rich secretory protein LCCL domain containing 1 (CRISPLD1), chromosome 15 open reading frame 48 (C15orf48), meningioma expressed antigen 5 (hyaluronidase) (MGEA5), sema domain, transmembrane domain (TM), and cytoplasmic domain, (semaphorin) 6B (SEMA6B), metastasis associated lung adenocarcinoma transcript 1 (non-protein coding) (MALAT1), zinc finger, MYND-type containing 12 (ZMYND12), solute carrier family 4, sodium borate transporter, member 11 (SLC4A11), DI03 opposite strand/antisense RNA (non-protein coding) (DIO3OS), testis expressed 101 (TEX101), cytokine inducible SH2-containing protein (CISH), cardiolipin synthase 1 (CRLS1), peroxisomal membrane protein 4, 24 kDa (PXMP4), protocadherin alpha 1 /// protocadherin alpha 10 /// protocadherin alpha 11 ///protocadherin alpha 12 /// protocadherin alpha 13 /// protocadherin alpha 2 /// protocadherin alpha 3 /// protocadherin alpha 4 /// protocadherin alpha 5 /// protocadherin alpha 6 ///protocadherin alpha 7 /// protocadherin alpha 8 /// protocadherin alpha 9 /// protocadherin alpha subfamily C, 1

/// protocadherin alpha subfamily C, 2 (PCDHA 1 /// PCDHA10 /// PCDHA 11 ///PCDHA12 ///PCDHA13 /// PCDHA2 /// PCDHA3 /// PCDHA4 /// PCDHAS /// PCDHA6 ///PCDHA7 ///PCDHA8 /// PCDHA9 /// PCDHAC1 /// PCDHAC2), membrane-spanning 4-domains, subfamily A, member 8B (MS4A8B), brain expressed X-linked 2 (BEX2), transient receptor potential cation channel, subfamily M, member 6 (TRPM6), Rho GTPase activating protein 9 (ARHGAP9), SMEK homolog 2, suppressor of mekl (Dictyostelium) (SMEK2), kringle containing transmembrane protein 1 (KREMEN1), tumor necrosis factor receptor superfamily, member 18 (TNFRSF18), WAS protein family, member 2 (WASF2), small nucleolar RNA host gene 1 (non-protein coding) /// small nucleolar RNA, C/D box 22 /// small nucleolar RNA, C/D box 25 /// small nucleolar RNA, C/D box 26 /// small nucleolar RNA, C/D box 27 /// small nucleolar RNA, C/D box 28 /// small nucleolar RNA, C/D box 29 /// small nucleolar RNA, C/D box 31 (SNHG1 /// SNORD22 /// SNORD25 /// SNORD26 /// SNORD27 ///SNORD28 /// SNORD29 /// SNORD31), G patch domain containing 4 (GPATCH4), H19, imprinted maternally expressed transcript (non-protein coding) /// microRNA 675 (H19 ///MIR675), uncharacterized LOC100506548 /// ribosomal protein L37 (LOC100506548 ///RPL37), glycerophosphocholine phosphodiesterase GDE1 homolog (*S. cerevisiae*) (GPCPD1), SLAIN motif family, member 2 (SLAIN2), pyruvate dehydrogenase phosphatase regulatory subunit (PDPR), aspartate beta-hydroxylase (ASPH), spire homolog 1 (*Drosophila*) (SPIRE1), ST3 beta-galactoside alpha-2,3-sialyltransferase 1 (ST3GAL1), rabaptin, RAB GTPase binding effector protein 1 (RABEP1), 2-oxoglutarate and iron-dependent oxygenase domain containing 1 (OGFOD1), transmembrane protein 18 (TMEM18), solute carrier family 1 (glial high affinity glutamate transporter), member 2 (SLC1A2), zinc finger protein 295 (ZNF295), mitochondrial ribosomal protein L50 (MRPL50), solute carrier family 45, member 4 (SLC45A4), phosphoprotein associated with glycosphingolipid microdomains 1 (PAG1), collagen, type XII, alpha 1 (COL12A1), centrosomal protein 95 kDa (CEP95), HNRNPU antisense RNA 1 (non-protein coding) (HNRNPU-AS1), cingulin-like 1 (CGNL1), eukaryotic translation initiation factor 2C, 2 (EIF2C2), pleckstrin homology-like domain, family A, member 1 (PHLDA1), DDHD domain containing 1 (DDHD1), BPI fold containing family B, member 1 (BPIFB1), synaptotagmin XIII (SYT13), elongation factor, RNA polymerase II, 2 (ELL2), zinc finger protein 90 homolog (mouse) (ZFP90), uncharacterized LOC100288152 (LOC100288152), collagen, type VIII, alpha 1 (COL8A1), chloride channel, voltage-sensitive 5 (CLCNS), delta/notch-like EGF repeat containing (DNER), spectrin, beta, non-erythrocytic 1 (SPTBN1), zinc finger, matrin-type 1 (ZMAT1), Alport syndrome, mental retardation, midface hypoplasia and elliptocytosis chromosomal region gene 1 (AMMECR1), RMI2, RecQ mediated genome instability 2, homolog (*S. cerevisiae*) (RMI2), transmembrane 7 superfamily member 3 (TM7SF3), NHS-like 1 (NHSL1), histidine triad nucleotide binding protein 3 (HINT3), CD109 molecule (CD109), GTP binding protein 5 (putative) (GTPBPS), zinc finger protein 251 (ZNF251), chromosome 8 open reading frame 42 (C8orf42), ADAM metallopeptidase with thrombospondin type 1 motif, 9 (ADAMTS9), follistatin (FST), unc-5 homolog B (*C. elegans*) (UNCSB), leucine-rich repeats and immunoglobulin-like domains 3 (LRIG3), SRY (sex determining region Y)-box 8 (50X8), DEP domain containing 1B (DEPDC1B), notch 2 N-terminal like (NOTCH2NL), glycosyltransferase 8 domain containing 2 (GLT8D2), inhibin, beta A (INHBA), ELOVL fatty acid elongase 7 (ELOVL7), sushi domain containing 3 (SUSD3), KIAA1211 (KIAA1211), POCS centriolar protein homolog (*Chlamydomonas*) (POCS), chaperonin containing TCP1, subunit 6 (zeta) pseudogene 1 /// chaperonin containing TCP1, subunit 6 (zeta) pseudogene 3 (CCT6P1 /// CCT6P3), vestigial like 3 (*Drosophila*) (VGLL3), forkhead box Q1 (FOXQ1), uncharacterized protein MGC16121 /// microRNA 503 (MGC16121 ///MIR503), GDNF family receptor alpha 1 (GFRA1), tetraspanin 11 (TSPAN11), F-box and leucine-rich repeat protein 16 (FBXL16), transmembrane protein 63C (TMEM63C), RNA binding motif protein, X-linked-like 1 (RBMXL1), programmed cell death 5 (PDCD5), chromosome 16 open reading frame 74 (C16orf74), formin-like 3 (FMNL3), family with sequence similarity 115, member C pseudogene (LOC154761), uncharacterized LOC100506234 ///transmembrane protein 185A (LOC100506234 /// TMEM185A), FYVE, RhoGEF and PH domain containing 4 (FGD4), zymogen granule protein 16 homolog B (rat) (ZG16B), leucine-rich repeats and calponin homology (CH) domain containing 3 (LRCH3), cortexin 1 (CTXN1), ceruloplasmin (ferroxidase) (CP), sortilin-related VPS10 domain containing receptor 1 (SORCS1), zinc finger protein 252, pseudogene (ZNF252P), growth arrest-specific 5 (non-protein coding) /// small nucleolar RNA, C/D box 44 /// small nucleolar RNA, C/D box 47 ///small nucleolar RNA, C/D box 76 /// small nucleolar RNA, C/D box 77 /// small nucleolar RNA, C/D box 79 /// small nucleolar RNA, C/D box 80 /// small nucleolar RNA, C/D box 81 (GASS ///SNORD44 ///SNORD47 /// SNORD76 /// SNORD77 /// SNORD79 /// SNORD80 ///SNORD81), anterior gradient 3 homolog (*Xenopus laevis*) (AGR3), FSHD region gene 1 pseudogene (LOC283788), claudin 11 (CLDN11), nanos homolog 1 (*Drosophila*) (NANOS1), chromosome 1 open reading frame 162 (C1orf162), dipeptidyl-peptidase 6 (DPP6), outer dense fiber of sperm tails 2-like (ODF2L), small nucleolar RNA host gene 9 (non-protein coding) ///small nucleolar RNA, H/ACA box 78 (SNHG9 /// SNORA78), SRY (sex determining region Y)-box 7 (50X7), uncharacterized LOC378805 (F1143663), RAB27B, member RAS oncogene family (RAB27B), CD36 molecule (thrombospondin receptor) (CD36), prostaglandin reductase 1 (PTGR1), activating transcription factor 7 (ATF7), derlin 3 (DERL3), carboxylesterase 4A (CES4A), dachshund homolog 1 (*Drosophila*) (DACH1), chromosome 9 open reading frame 24 (C9orf24), SAP domain containing ribonucleoprotein (SARNP), chromosome 17 open reading frame 100 (C17orf100), protogenin (PRTG), prokineticin 1 (PROK1), protogenin (PRTG), autophagy related 9B (ATG9B), programmed cell death 6 pseudogene (LOC728613), ankyrin repeat domain 28 (ANKRD28), autophagy related 16-like 2 (*S. cerevisiae*) (ATG16L2), RNA binding motif protein 26 (RBM26), interferon-induced protein with tetratricopeptide repeats 3 (IFIT3), family with sequence similarity 46, member B (FAM46B), chromosome 14 open reading frame 118 (C14orf118), zinc finger protein 502 (ZNF502), chromosome 20 open reading frame 85 (C20orf85), dispatched homolog 2 (*Drosophila*) (DISP2), family with sequence similarity 132, member B (FAM132B), uncharacterized LOC728431 (LOC728431), smoothelin-like 2 (SMTNL2), zinc finger protein 207 (ZNF207), synaptosomal-associated protein, 23 kDa (SNAP23), family with sequence similarity 166, member B (FAM166B), peptidase inhibitor 15 (PI15), Ewing sarcoma breakpoint region 1 (EWSR1), ring finger protein 213 (RNF213), cell division cycle associated 7 (CDCA7), PITPNM family member 3 (PITPNM3), succinate dehydrogenase complex, subunit A, flavoprotein (Fp) pseudogene /// succinate dehydrogenase complex, subunit A, flavoprotein (Fp) /// succinate dehydrogenase complex, subunit A, flavoprotein pseudogene 1 /// succinate dehydrogenase complex, subunit A, flavoprotein pseudogene 2 (LOC220729 /// SDHA /// SDHAP1 /// SDHAP2), ubiquitin specific peptidase 53 (USP53), coagulation factor II (thrombin) receptor-like 2 (F2RL2), DEAD (Asp-Glu-Ala-Asp) box helicase 17 (DDX17), uncharacterized LOC100507100 (LOC100507100), chromosome 2 open reading frame 82 (C2orf82), lysophosphatidic acid receptor 5 (LPARS), BCL2-associated athanogene 5 (BAGS), uncharacterized LOC100507008 (LOC100507008), polycystic kidney and hepatic disease 1 (autosomal recessive)-like 1 (PKHD1L1), MIR210 host gene (non-protein coding) (MIR210HG), family with sequence similarity 210, member A (FAM210A), uncharacterized LOC100505875 (LOC100505875), acrosin binding protein (ACRBP), spastic paraplegia 7 (pure and complicated autosomal recessive) (SPG7), paralemmin 3 (PALM3), chromosome 1 open reading frame 194 (C1orf194), chromosome 1 open reading frame 192 (C1orf192), microRNA 30c-2(MIR30C2), inositol hexakisphosphate kinase 3 (IP6K3), WAS/WASL interacting protein family, member 1 (WIPF1), MGC44478 (FDPSL2A), guanylate binding protein 1, interferon-inducible (GBP1), gap junction protein, beta 6, 30 kDa (GJB6), eomesodermin (EOMES), noggin (NOG), uncharacterized LOC401149 /// uncharacterized LOC441124 /// uncharacterized LOC729021 /// uncharacterized LOC729218 (F1114186 ///LOC4411-24 ///LOC729021 /// LOC729218), keratin 80 (KRT80), NCK-associated protein 5-like (NCKAPSL), chromosome 16 open reading frame 53 (C16orf53), DDB1 and CUL4 associated factor 17(DCAF17), IKAROS family zinc finger 2 (Helios) (IKZF2), filamin A interacting protein 1 (FILIP1), bicaudal D homolog 1 (*Drosophila*) (BICD1), zinc finger protein 678 (ZNF678), epiplakin 1 (EPPK1), naked cuticle homolog 2 (*Drosophila*) (NKD2), unc-51-like kinase 4 (*C. elegans*) (ULK4), Src-like-adaptor 2 (SLA2), zinc finger protein 880 (ZNF880), zinc finger protein 274 (ZNF274), Collagen, type III, alpha 1 (COL3A1), tRNA methyltransferase 13 homolog (*S. cerevisiae*) (TRMT13), Ral GTPase activating protein, alpha subunit 2 (catalytic) (RALGAPA2), multiple EGF-like-domains 10 (MEGF10), Sp3 transcription factor (SP3), prokineticin 2 (PROK2), LOXL1 antisense RNA 1 (non-protein coding) (LOXL1-AS1), Annexin A1 (ANXA1), netrin G2 (NTNG2), coiled-coil domain containing 114 (CCDC114), KIAA1609 (KIAA1609), RAB12, member RAS oncogene family (RAB12), potassium channel, subfamily K, member 3 (KCNK3), guanine nucleotide binding protein (G protein), gamma transducing activity polypeptide 2 (GNGT2), GTPase, IMAP family member 8 (GIMAP8), chromosome 14 open reading frame 28 (C14orf28), uncharacterized LOC100507316 (LOC100507316), low density lipoprotein receptor-related protein associated protein 1 (LRPAP1), discs, large (*Drosophila*) homolog-associated protein 1 (DLGAP1), glycerol-3-phosphate acyltransferase 2, mitochondrial (GPAT2), mannan-binding lectin serine peptidase 1 (C4/C2 activating component of Ra-reactive factor) (MASP1), uncharacterized LOC100422737 (LOC100422737), mRNA turnover 4 homolog (*S. cerevisiae*) (MRTO4), scavenger receptor class A, member 5 (putative) (SCARAS), yippee-like 4 (*Drosophila*) (YPEL4), cyclin-dependent kinase 9 (CDK9), KIAA1609 (KIAA1609), calcyphosine-like (CAPSL), vacuolar protein sorting 13 homolog B (yeast) (VPS13B), retinol dehydrogenase 5 (11-cis/9-cis) (RDHS), family with sequence similarity 3, member C (FAM3C), protein tyrosine phosphatase, non-receptor type 5 (striatum-enriched) (PTPNS), transmembrane protein 132B (TMEM132B), G protein-coupled receptor 110 (GPR110), BCL2-like 10 (apoptosis facilitator) (BCL2L10), zinc finger protein 667 (ZNF667), GSG1-like (GSG1L), coiled-coil domain containing 78 (CCDC$_7$8), lipoma HMGIC fusion partner-like 3 (LHFPL3), HOXB cluster antisense RNA 3 (non-protein coding) (HOXB-AS3), homogentisate 1,2-dioxygenase (HGD), solute carrier family 6 (neurotransmitter transporter, GABA), member 13 (SLC6A13), protein kinase, interferon-inducible double stranded RNA dependent activator (PRKRA), PEST proteolytic signal containing nuclear protein (PCNP), SRY (sex determining region Y)-box 5 (50X5), pleckstrin homology domain containing, family A (phosphoinositide binding specific) member 2 (PLEKHA2), AT rich interactive domain 1B (SWI1-like) (ARID1B), huntingtin-associated protein 1 (HAP1), transmembrane protein 136 (TMEM136), chromosome 11 open reading frame 80 (C11orf80), chromosome 1 open reading frame 168 (C1orf168), methylenetetrahydrofolate dehydrogenase (NADP+dependent) 2-like (MTHFD2L), prohibitin pseudogene (LOC494150), arginine vasopressin receptor 1A (AVPR1A), NOP2/Sun domain family, member 7 (NSUN7), dedicator of cytokinesis 8 (DOCKS), methylenetetrahydrofolate reductase (NAD(P)H) (MTHFR), zinc finger protein 786 (ZNF786), uncharacterized LOC100505912 (LOC100505912), F-box and leucine-rich repeat protein 20 (FBXL20), phosphatidylinositol-specific phospholipase C, X domain containing 3 (PLCXD3), centrosomal protein 152 kDa (CEP152), retinol binding protein 1, cellular (RBP1), HOXA11 antisense RNA (non-protein coding) (HOXA11-AS), acyl-CoA oxidase-like (ACOXL), zinc finger, FYVE domain containing 16 (ZFYVE16), hairless homolog (mouse) (HR), coiled-coil domain containing 15 (CCDC15), nucleoporin like 1 (NUPL1), sodium channel, non-voltage-gated 1, gamma subunit (SCNN1G), chromosome 6 open reading frame 132 (C6orf132), carboxypeptidase M (CPM), nuclear factor of kappa light polypeptide gene enhancer in B-cells inhibitor, delta (NFKBID), xanthine dehydrogenase (XDH), ankyrin repeat domain 33 (ANKRD33), Clq and tumor necrosis factor related protein 6 (C1QTNF6), uncharacterized LOC100505648 (LOC100505648), zinc finger protein 420 (ZNF420), FSHD region gene 1 pseudogene (LOC642236), MAP6 domain containing 1 (MAP6D1), uncharacterized LOC100506303 /// uncharacterized LOC100653149 /// uncharacterized LOC400879 (LOC100506303 /// LOC100653149 /// LOC400879), phosphatidylinositol-4-phosphate 5-kinase-like 1 (PIP5KL1), DDB1 and CUL4 associated factor 8 (DCAF8), castor zinc finger 1 (CASZ1), KAT8 regulatory NSL complex subunit 1 (KANSL1), WD repeat domain 38 (WDR38), zinc finger protein 793 (ZNF793), zinc finger protein 300 pseudogene 1 (ZNF300P1), uncharacterized LOC100505679 (LOC100505679), cytochrome c, somatic (CYCS), methenyltetrahydrofolate synthetase domain containing (MTHFSD), phosphatase and actin regulator 2 (PHACTR2), sphingosine-1-phosphate phosphatase 2 (SGPP2), C-reactive protein, pentraxin-related (CRP), aquaporin 3 (Gill blood group) (AQP3), erythropoietin receptor (EPOR), cadherin, EGF LAG seven-pass G-type receptor 1 (flamingo homolog, Drosophila) (CELSR1), leucine zipper, putative tumor suppressor 1 (LZTS1), RAB15, member RAS oncogene family (RAB15), zinc finger protein 814 (ZNF814), Zinc finger protein 718 (ZNF718), dual specificity phosphatase 5 pseudogene (DUSPSP), major facilitator superfamily domain containing 2A (MFSD2A), histidine triad nucleotide binding protein 1 (HINT1), Vasohibin 1 (VASH1), uncharacterized LOC440993 (LOC440993), solute carrier family 38, member 10 (SLC38A10), ribosomal protein S16 pseudogene 5 (RPS16P5), small nucleolar RNA, C/D box 8 (SNORD8), defensin, beta 124 (DEFB124), uncharacterized LOC100505812 (LOC100505812), tripartite motif containing 13 (TRIM13), GC-rich promoter binding protein 1-like 1 (GPBP1L1), trans-2,3-enoyl-CoA reductase (TECR), MAX-like protein X (MLX), myelin protein zero-like 3 (MPZL3), LSM4 homolog, U6 small nuclear RNA associated (S. cerevisiae) (LSM4), poly(rC) binding protein 2 (PCBP2), myosin, light chain 6, alkali, smooth muscle and non-muscle (MYL6), Neudesin neurotrophic factor (NENF), SH3-domain binding protein 2 (SH3BP2), uncharacterized LOC100653010 (LOC100653010), endogenous retrovirus group 3, member 2 (ERV3-2), uncharacterized protein PRO2852 (PRO2852), LIM and cysteine-rich domains 1 (LMCD1), Nudix (nucleoside diphosphate linked moiety X)-type motif 4 (NUDT4), Cysteine rich transmembrane BMP regulator 1 (chordin-like) (CRIM1), SLIT-ROBO Rho GTPase activating protein 2 pseudogene 1 (SRGAP2P1), Discoidin, CUB and LCCL domain containing 2 (DCBLD2), ORAI calcium release-activated calcium modulator 2 (ORAI2), uncharacterized LOC100653336 /// PGMS antisense RNA 1 (non-protein coding) (LOC100653336 /// PGM5-AS1), Ras association (RalGDS/AF-6) and pleckstrin homology domains 1 (RAPH1), Congenital dyserythropoietic anemia, type I (CDAN1), uncharacterized LOC100506941 (LOC100506941), uncharacterized LOC100506165 (LOC100506165), B eta-2-microglobulin (B2M), KRR1, small subunit (SSU) processome component, homolog (yeast) (KRR1), breast cancer anti-estrogen resistance 1 (BCAR1), Early B-cell factor 1 (EBF1), ubiquitin-conjugating enzyme E2I (UBE2I), CDC14 cell division cycle 14 homolog B (S. cerevisiae) (CDC14B), small nucleolar RNA, C/D box 3B-1 /// small nucleolar RNA, C/D box 3B-2/// small nucleolar RNA, C/D box 3D (SNORD3B-1 /// SNORD3B-2/// SNORD3D), nuclear receptor binding SET domain protein 1 (NSD1), DDB1 and CUL4 associated factor 7 (DCAF7), Suppressor of zeste 12 homolog pseudogene (SUZ12P), Interferon (alpha, beta and omega) receptor 1 (IFNAR1), Nucleoporin 62 kDa (NUP62), uncharacterized LOC100134445 (LOC100134445), WW and C2 domain containing 1 (WWC1), insulin receptor substrate 1 (IRS1), uncharacterized LOC100653149 (LOC100653149), Ring finger protein 144B (RNF144B), DAPK1 intronic transcript 1 (non-protein coding) (DAPK1-IT1), Solute carrier family 2 (facilitated glucose transporter), member 8 (SLC2A8), uncharacterized LOC441179 (LOC441179), Zinc finger, AN1-type domain 6 (ZFAND6), uncharacterized LOC100507153 (LOC100507153), Proteasome (prosome, macropain) assembly chaperone 4 (PSMG4), Nicotinamide phosphoribosyltransferase (NAMPT), Zinc finger protein 652 (ZNF652), RAB18, member RAS oncogene family (RAB18), and mucin 20, cell surface associated (MUC20) in the tissue sample comprising endometrial cells from a subject;

where the determining comprises hybridizing RNA from the tissue samples to a microarray;

associating the expression level with the presence and—severity of endometriosis;

providing a diagnosis of the presence and severity of endometriosis based on the association and providing a course of treatment based on the diagnosis, where the treatment comprises administering an effective amount of hormone therapy, chemotherapy, pharmacotherapy, immunotherapy, targeted therapies, or surgical treatment to the subject.

2. The method of claim 1, further comprising determining a disease class by associating the expression level of at least one set of genes comprising the genes in sets (i), (ii), (iv), (v), (vii) or (viii) in claim 1 with the disease class.

3. The method of claim 1, further comprising classifying the severity of endometriosis into a severity class selected from minimal to mild endometriosis or moderate to severe endometriosis, where the severity of endometriosis is classified by associating the expression level of at least one set of genes comprising the genes in sets (iii), (vi), or (ix) in claim 1 with the severity class.

4. The method of claim 1, wherein the presence and severity of endometriosis is menstrual cycle phase-unrestricted, menstrual cycle phase-restricted, or menstrual cycle phase-specific.

5. The method of claim 1, wherein the tissue sample is from the proliferative phase (PE), early secretory phase (ESE), or mid-secretory phase (MSE) of the menstrual cycle.

6. The method of claim 1, wherein the tissue sample is obtained by surgery or biopsy.

7. The method of claim 1, further comprising:
  i) comparing the expression level with the expression level of the at least one set of genes comprising the genes in sets (i), (ii), (iii), (iv), (v), (vi), (vii), (viii) or (ix) in claim 1 in a tissue sample from a control subject not having endometriosis; and
  ii) providing a diagnosis of the presence and severity of endometriosis if the expression level of the set of genes in the tissue sample from the subject suffering from endometriosis is statistically different from the expression level in the tissue sample from the control subject.

8. The method of claim 1, wherein the diagnosis of the presence and severity of endometriosis provided is at least 90% accurate.

9. A method for detecting the expression of genes in a tissue sample comprising endometrial cells or tissue, comprising:
- obtaining a tissue sample comprising endometrial cells from a subject suspected of suffering from endometriosis;
- detecting the expression level of at least one set of genes, the set of genes comprising the genes in sets (i), (ii), (iii), (iv), (v), (vi), (vii), (viii) or (ix) in claim 1 in a tissue sample comprising endometrial cells from a subject,
- where the detecting comprises hybridizing RNA from the tissue samples to a microarray.

10. The method of claim 1, wherein the expression level of the genes in sets (i), (ii), (iii), (iv), (v), (vi), (vii), (viii) and (ix) is determined.

* * * * *